US011253645B2

(12) United States Patent
Avalos et al.

(10) Patent No.: US 11,253,645 B2
(45) Date of Patent: Feb. 22, 2022

(54) APPARATUSES, SYSTEMS AND METHODS FOR CONTROLLED DELIVERY OF THERAPEUTICS AND RELATED SUBSTANCES

(71) Applicant: Cedars-Sinai Medical Center, Los Angeles, CA (US)

(72) Inventors: Pablo Avalos, West Hollywood, CA (US); Doniel Drazin, Los Angeles, CA (US); Clive Svendsen, Pacific Palisades, CA (US); Michael John Baker, Portland, OR (US); Mark Sasha Drlik, Victoria (CA)

(73) Assignee: Cedars-Sinai Medical Center, Los Angeles, CA (US)

( * ) Notice: Subject to any disclaimer, the term of this patent is extended or adjusted under 35 U.S.C. 154(b) by 344 days.

(21) Appl. No.: 15/523,042

(22) PCT Filed: Oct. 29, 2015

(86) PCT No.: PCT/US2015/058134
§ 371 (c)(1),
(2) Date: Apr. 28, 2017

(87) PCT Pub. No.: WO2016/069936
PCT Pub. Date: May 6, 2016

(65) Prior Publication Data
US 2018/0280611 A1   Oct. 4, 2018

Related U.S. Application Data

(60) Provisional application No. 62/072,414, filed on Oct. 29, 2014, provisional application No. 62/072,373, (Continued)

(51) Int. Cl.
*A61M 5/158* (2006.01)
*A61B 90/11* (2016.01)
(Continued)

(52) U.S. Cl.
CPC ......... *A61M 5/158* (2013.01); *A61B 17/3401* (2013.01); *A61B 17/3403* (2013.01);
(Continued)

(58) Field of Classification Search
CPC .... A61M 5/145; A61M 5/1452; A61M 5/158; A61M 5/46; A61M 2005/1586;
(Continued)

(56) References Cited

U.S. PATENT DOCUMENTS 2,569,901 A * 10/1951 Ernest ................... A61M 5/178
604/117
3,530,785 A *  9/1970 Peters ..................... A47J 43/16
99/532

(Continued)

FOREIGN PATENT DOCUMENTS

CA       2239614 C      5/2005
CA       2910268 A1    11/2014
(Continued)

OTHER PUBLICATIONS

International Search Report and Written Opinion for PCT/US2014/036161 dated Aug. 27, 2014, 12 pages.
(Continued)

*Primary Examiner* — Kami A Bosworth
(74) *Attorney, Agent, or Firm* — Nixon Peabody LLP

(57) ABSTRACT

The present invention teaches apparatuses, systems and methods for performing a variety of medical procedures, including those involving introducing one or more substances into a subject's body. In some embodiments, the invention teaches automatically performing guided injections into a tissue site (e.g. spinal cord) of a subject by using one or more electronically operated components including a cannula, a syringe pump, and a stereotactic device.

10 Claims, 39 Drawing Sheets

Related U.S. Application Data filed on Oct. 29, 2014, provisional application No. 62/072,365, filed on Oct. 29, 2014.

(51) Int. Cl.
```
A61B 17/34      (2006.01)
A61K 9/00       (2006.01)
A61K 35/30      (2015.01)
A61M 5/145      (2006.01)
A61B 90/57      (2016.01)
A61B 17/00      (2006.01)
```

(52) U.S. Cl.
CPC ............ *A61B 90/11* (2016.02); *A61K 9/0019* (2013.01); *A61K 9/0085* (2013.01); *A61K 35/30* (2013.01); *A61M 5/1452* (2013.01); A61B 2017/00221 (2013.01); A61B 2017/3409 (2013.01); A61B 2090/571 (2016.02); A61M 2005/1585 (2013.01); A61M 2005/1586 (2013.01); A61M 2005/1587 (2013.01); A61M 2202/09 (2013.01); A61M 2209/082 (2013.01); A61M 2210/1003 (2013.01)

(58) Field of Classification Search
CPC .. A61M 2005/1587; A61M 2025/0004; A61M 2025/0006; A61M 2025/0293; A61M 2209/082; A61M 2210/0687; A61M 2210/0693; A61M 2210/1003; A61M 5/142; A61M 5/20; A61M 5/24; A61M 2005/1585; A61M 25/06; A61M 2202/09; A61B 17/3401; A61B 2017/3403; A61B 2017/3405; A61B 2017/3409; A61B 2017/3443; A61B 90/10; A61B 90/11; A61B 90/50; A61B 90/57; A61B 2090/571

See application file for complete search history.

(56) References Cited

U.S. PATENT DOCUMENTS

| | | | |
|---|---|---|---|
| 3,817,249 A | 6/1974 | Nicholson | |
| 4,467,791 A | 8/1984 | Cabrera et al. | |
| 5,647,373 A * | 7/1997 | Paltieli | A61B 8/00 600/461 |
| 5,769,086 A | 6/1998 | Ritchart et al. | |
| 5,830,188 A | 11/1998 | Abouleish | |
| 5,906,594 A * | 5/1999 | Scarfone | A61B 17/34 604/165.01 |
| 6,139,493 A | 10/2000 | Koros et al. | |
| 6,270,481 B1 | 8/2001 | Mason et al. | |
| 6,322,500 B1 | 11/2001 | Sikora et al. | |
| 7,833,217 B2 * | 11/2010 | Boulis | A61B 5/6848 604/240 |
| 2002/0133174 A1* | 9/2002 | Charles | A61B 34/37 606/130 |
| 2003/0125753 A1 | 7/2003 | Saracione | |
| 2003/0199822 A1 | 10/2003 | Alchas et al. | |
| 2003/0208187 A1 | 11/2003 | Layer | |
| 2004/0181273 A1* | 9/2004 | Brasington | A61M 29/02 623/1.15 |
| 2005/0152995 A1 | 7/2005 | Chen et al. | |
| 2005/0193451 A1 | 9/2005 | Quistgaard et al. | |
| 2006/0106416 A1 | 5/2006 | Douglas et al. | |
| 2006/0135945 A1 | 6/2006 | Bankiewicz et al. | |
| 2006/0224044 A1 | 10/2006 | Marchek et al. | |
| 2007/0123753 A1 | 5/2007 | Abdelgany et al. | |
| 2007/0233146 A1 | 10/2007 | Henniges et al. | |
| 2007/0260190 A1* | 11/2007 | Lin | A61M 25/0637 604/192 |
| 2008/0183046 A1 | 7/2008 | Boucher et al. | |
| 2008/0188718 A1 | 8/2008 | Spitler et al. | |
| 2009/0036746 A1 | 2/2009 | Blackwell et al. | |
| 2009/0163808 A1 | 6/2009 | Peyrard et al. | |
| 2009/0287043 A1 | 11/2009 | Naito et al. | |
| 2010/0240989 A1 | 9/2010 | Stoianovici et al. | |
| 2010/0241136 A1 | 9/2010 | Doyle et al. | |
| 2012/0053573 A1 | 3/2012 | Alksnis | |
| 2012/0209110 A1 | 8/2012 | Bankiewicz et al. | |
| 2012/0226145 A1 | 9/2012 | Chang et al. | |
| 2013/0066334 A1 | 3/2013 | Schoepp | |
| 2013/0079799 A1 | 3/2013 | Kim et al. | |
| 2014/0058210 A1 | 2/2014 | Raymond et al. | |
| 2014/0066718 A1 | 3/2014 | Fiechter et al. | |
| 2014/0142422 A1 | 5/2014 | Manzke et al. | |
| 2014/0180249 A1 | 6/2014 | Solar et al. | |
| 2014/0243809 A1 | 8/2014 | Gelfand et al. | |
| 2016/0100897 A1 | 4/2016 | Avalos et al. | |
| 2019/0059869 A1 | 2/2019 | Avalos et al. | |
| 2020/0253684 A1 | 8/2020 | Avalos et al. | |

FOREIGN PATENT DOCUMENTS

| | | |
|---|---|---|
| CA | 2966029 A1 | 5/2016 |
| CA | 3003454 A1 | 5/2017 |
| CN | 1899229 A | 1/2007 |
| CN | 101123919 A | 2/2008 |
| CN | 102300512 A | 12/2011 |
| CN | 102379742 A | 3/2012 |
| CN | 202238111 U | 5/2012 |
| CN | 103561796 A | 2/2014 |
| CN | 103690205 A | 4/2014 |
| CN | 105338910 A | 2/2016 |
| CN | 107106814 A | 8/2017 |
| CN | 108289602 A | 7/2018 |
| DE | 10-2007-054317 A1 | 5/2009 |
| DE | 202012101617 U1 | 5/2012 |
| EP | 2991560 A1 | 3/2016 |
| EP | 3212271 A1 | 9/2017 |
| EP | 3367877 A1 | 9/2018 |
| HK | 1221389 A1 | 6/2017 |
| IN | 3085/MUMNP/2015 A | 3/2016 |
| IN | 201727017050 A | 7/2017 |
| JP | 58-124456 A | 7/1983 |
| JP | 58-133246 A | 8/1983 |
| JP | 10-507938 A | 8/1998 |
| JP | 515372 | 9/2001 |
| JP | 2005-524442 A | 8/2005 |
| JP | 2007105392 A | 4/2007 |
| JP | 2008-515554 A | 5/2008 |
| JP | 2011-516205 A | 5/2011 |
| JP | 2014-386 A | 1/2014 |
| JP | 2016522710 A | 8/2016 |
| JP | 2017537679 A | 12/2017 |
| JP | 2018-535004 A | 11/2018 |
| JP | 6456924 B2 | 1/2019 |
| KR | 10-2016-0008209 A | 1/2016 |
| KR | 10-2017-0076705 A | 7/2017 |
| KR | 2018-0079346 A | 7/2018 |
| WO | 98/39039 A1 | 9/1998 |
| WO | 2007/052975 A1 | 5/2007 |
| WO | 2011/156331 A2 | 12/2011 |
| WO | 2011/159733 A1 | 12/2011 |
| WO | WO-2014047540 A1 * | 3/2014 |
| WO | 2014/179458 A1 | 11/2014 |
| WO | 2016/069936 A1 | 5/2016 |
| WO | 2017/075503 A1 | 5/2017 |

OTHER PUBLICATIONS

International Preliminary Report on Patentability for PCT/US2014/036161 dated Nov. 3, 2015, 11 pages.
EP 14791033.5 European Extended Search Report dated Aug. 25, 2016, 13 pages.
International Search Report and Written Opinion for PCT/US2015/58134 dated Feb. 26, 2016, 15 pages.
International Preliminary Report on Patentability for PCT/US2015/58134 dated May 2, 2017, 12 pages.
International Search Report and Written Opinion for PCT/US2016/059539 dated Mar. 3, 2017, 16 pages.

(56) References Cited

OTHER PUBLICATIONS

Cole et al., Design of a Robotic System for MRI-Guided Deep Brain Stimulation Electrode Placement, 2009 IEEE International Conference on Robotics and Automation, 2009, pp. 4450-4456.
European Extended Search Report for EP15855587 dated Jul. 19, 2018, 6 pages.
Extended European Search Report dated Mar. 26, 2019 for EP 16860979, 8 pages.
CN Office Action and Search Report for CN 2015800702505 dated Aug. 5, 2019, 13 pages.
CN Search Report for Appl. No. 2016800693500 dated Sep. 17, 2019, 13 pages.

* cited by examiner

APPARATUSES, SYSTEMS AND METHODS FOR CONTROLLED DELIVERY OF THERAPEUTICS AND RELATED SUBSTANCES

CROSS-REFERENCE TO RELATED APPLICATIONS

This application is a National Phase of International Application No. PCT/US2015/058134, filed Oct. 29, 2015, which designated the U.S. and that International Application was published under PCT Article 21(2) in English. This application claims the priority benefit of U.S. Provisional Application No. 62/072,365 filed on Oct. 29, 2014, U.S. Provisional Application No. 62/072,373 filed Oct. 29, 2014, and U.S. Provisional Application No. 62/072,414, filed on Oct. 29, 2014, the contents all of which are hereby incorporated herein by reference in their entirety.

FIELD OF THE INVENTION

The present invention generally relates to apparatuses, systems and methods for medical procedures, and especially those that require injecting a substance into a subject's body.

BACKGROUND

All publications herein are incorporated by reference to the same extent as if each individual publication or patent application was specifically and individually indicated to be incorporated by reference. The following description includes information that may be useful in understanding the present invention. It is not an admission that any of the information provided herein is prior art or relevant to the presently claimed invention, or that any publication specifically or implicitly referenced is prior art.

When physicians are performing procedures on or around certain areas of the body such as the spinal cord, brain, and joints, very precise, controlled, and stable manipulations are often required to avoid patient injury and to optimize outcome. There is a need in the art for apparatuses, systems and methods that will improve the safety, precision, accuracy and efficiency of performing certain medical procedures in those areas, including procedures requiring the injection of one or more medically useful substances.

SUMMARY OF THE INVENTION

In various embodiments, the invention teaches a floating cannula system for injecting a substance into a subject, the system including: a base cannula including a proximal end, a distal end, and a lumen; a floating cannula including a lumen, wherein (1) the floating cannula is configured to be at least partially contained inside the lumen of the base cannula, (2) the floating cannula includes a proximal end and a distal end that extend farther proximally and distally than the proximal end and distal end of the base cannula when engaged therein, and (3) the floating cannula is configured to move in a direction along a longitudinal axis of the base cannula when engaged therein; a distal stopper connected to the distal end of the floating cannula, wherein the distal stopper is configured and positioned to prevent movement of the distal stopper in the proximal direction past the distal end of the base cannula, when the floating cannula is engaged in the base cannula; a proximal stopper connected to the proximal end of the floating cannula, wherein the proximal stopper is configured and positioned to prevent movement of the proximal stopper in the distal direction past the proximal end of the base cannula, and wherein the distance from the proximal stopper to the distal stopper is greater than the distance between the proximal and distal ends of the base cannula; a hollow needle connected to the distal end of the floating cannula; and a delivery tube connected to the hollow needle, wherein at least part of the length of the delivery tube is contained inside and/or connected to the lumen of the floating cannula and/or the lumen of the base cannula. In some embodiments, one or more support tabs are connected to the base cannula. In certain embodiments, the system further includes a connector removably attached to the support tabs. In some embodiments, the system further includes a stereotactic device including a guiding arm configured to be lowered into a surgical field, and the connector is removably attached to the guiding arm of the stereotactic device. In some embodiments, the delivery tube is connected to an external pump and reservoir, and the reservoir contains the substance to inject into the subject. In certain embodiments, the needle includes a tissue stopper. In certain embodiments, the positions of the distal and/or proximal stoppers on the floating cannula may be changed. In some embodiments, the support tabs include finger grips. In certain embodiments, the connector includes one or more indentations configured to closely fit an end of one or more of the support tabs. In some embodiments, the connector includes a tab lock that locks one or more of the support tabs in place in the one or more indentations.

In various embodiments, the invention teaches a method for injecting a substance into a subject. In some embodiments, the method includes (1) providing a floating cannula system including a base cannula including a proximal end, a distal end, and a lumen; a floating cannula including a lumen, wherein (a) the floating cannula is configured to be at least partially contained inside the lumen of the base cannula, (b) the floating cannula includes a proximal end and a distal end that extend farther proximally and distally than the proximal end and distal end of the base cannula when engaged therein, and (c) the floating cannula is configured to move in a direction along a longitudinal axis of the base cannula when engaged therein; a distal stopper connected to the distal end of the floating cannula, wherein the distal stopper is configured and positioned to prevent movement of the distal stopper in the proximal direction past the distal end of the base cannula, when the floating cannula is engaged in the base cannula; a proximal stopper connected to the proximal end of the floating cannula, wherein the proximal stopper is configured and positioned to prevent movement of the proximal stopper in the distal direction past the proximal end of the base cannula, and wherein the distance from the proximal stopper to the distal stopper is greater than the distance between the proximal and distal ends of the base cannula; a hollow needle connected to the distal end of the floating cannula; and a delivery tube connected to the hollow needle, wherein at least part of the length of the delivery tube is contained inside the lumen of the floating cannula and/or the lumen of the base cannula; (2) providing the substance to inject into the subject; and (3) utilizing the floating cannula system to inject the substance into the subject. In some embodiments, the floating cannula system further includes one or more support tabs connected to the base cannula. In certain embodiments, the floating cannula system further includes a connector removably attached to the support tabs. In certain embodiments, the floating cannula system further includes a stereotactic device including a guiding arm configured to be lowered into a surgical field, and the connector is removably attached to the guiding arm of the stereotactic device. In some embodiments, the delivery tube of the floating cannula system is connected to an external pump and reservoir, and the reservoir contains the substance injected into the subject. In some embodiments, the needle of the floating cannula system includes a tissue stopper. In certain embodiments, the positions of the distal and/or proximal stoppers on the floating cannula may be changed. In certain embodiments, the support tabs of the floating cannula system include finger grips. In certain embodiments, the connector of the floating cannula system includes one or more indentations configured to closely fit an end of one or more of the support tabs. In certain embodiments, the substance injected into the subject includes cells. In certain embodiments, the cells are neural progenitor cells. In certain embodiments, the substance including neural progenitor cells is injected into the subject's spinal cord. In certain embodiments, the subject has been diagnosed with a neurologic disease, neurologic trauma, cancer, or combinations thereof. In certain embodiments, the subject has been diagnosed with amyotrophic lateral sclerosis (ALS). In some embodiments, the neural progenitor cells express glial cell line derived neurotrophic factor.

In various embodiments, the invention teaches a kit including: any of the floating cannula systems described above; and instructions for the use thereof to inject a substance into a subject.

In various embodiments, the invention teaches a syringe pump system. In some embodiments, the system includes a motor assembly including (a) a housing, including a first end and a second end, (b) a motor, and (c) a rotatable drive shaft, wherein the motor is configured to cause the rotatable drive shaft to rotate, and the motor and rotatable drive shaft are at least partly contained within the housing; a carpule assembly including (a) a first end including an elongated inlet port, (b) a second end including an elongated outlet port, and (c) a chamber disposed between and in fluid communication with the elongated inlet port and the elongated outlet port; an elongated plunger, including (a) a receiving end, (b) a body, and (c) a pushing end, wherein (1) the elongated plunger is configured to nest within the elongated inlet port, (2) the pushing end of the plunger is configured to form a substantially fluid-tight seal with the chamber, and (3) the rotatable drive shaft is configured to apply a drive force to the receiving end of the plunger, either directly, or indirectly through an intervening shaft, such that the plunger can be pushed in the direction of the outlet port. In some embodiments, the syringe pump system further includes a coupling collar including a first end and a second end, wherein the first end of the coupling collar is configured to connect to the second end of the housing, and wherein the second end of the coupling collar is configured to connect to the first end of the carpule. In some embodiments, the syringe pump system further includes a delivery tube including a first end and a second end, wherein the first end of the delivery tube is connected to and in fluid communication with the second end of the carpule. In some embodiments, the second end of the delivery tube is connected to and in fluid communication with a cannula including a hollow needle. In some embodiments, the second end of the delivery tube is connected to and in fluid communication with a floating cannula system configured to inject a substance into a subject, the floating cannula system including: a base cannula including a proximal end, a distal end, and a lumen; a floating cannula including a lumen, wherein (1) the floating cannula is configured to be at least partially contained inside the lumen of the base cannula, (2) the floating cannula includes a proximal end and a distal end that extend farther proximally and distally than the proximal end and distal end of the base cannula when engaged therein, and (3) the floating cannula is configured to move in a direction along a longitudinal axis of the base cannula when engaged therein; a distal stopper connected to the distal end of the floating cannula, wherein the distal stopper is configured and positioned to prevent movement of the distal stopper in the proximal direction past the distal end of the base cannula, when the floating cannula is engaged in the base cannula; a proximal stopper connected to the proximal end of the floating cannula, wherein the proximal stopper is configured and positioned to prevent movement of the proximal stopper in the distal direction past the proximal end of the base cannula, and wherein the distance from the proximal stopper to the distal stopper is greater than the distance between the proximal and distal ends of the base cannula; a hollow needle connected to the distal end of the floating cannula; and wherein the second end of the delivery tube is connected to the hollow needle, and at least part of the length of the delivery tube is contained inside the lumen of the floating cannula and/or the lumen of the base cannula. In certain embodiments, a pair of support tabs are connected to the base cannula. In some embodiments, the syringe pump system further includes a connector removably attached to the support tabs. In certain embodiments, the syringe pump system further includes a stereotactic device including a guiding arm configured to be lowered into a surgical field, wherein the connector is removably attached to the guiding arm of the stereotactic device. In certain embodiments, the hollow needle includes a tissue stopper. In certain embodiments, the positions of the distal and/or proximal stoppers on the floating cannula may be changed. In some embodiments, the support tabs include finger grips. In some embodiments, the connector includes one or more indentations configured to closely fit an end of one or more of the support tabs. In some embodiments, the connector includes a tab lock that locks one or more of the support tabs in place in the one or more indentations. In some embodiments, the carpule includes a medically useful fluid substance. In some embodiments, the medically useful fluid substance includes cells. In some embodiments, the cells are neural progenitor cells. In some embodiments, the neural progenitor cells express glial cell line derived neurotrophic factor.

In various embodiments, the invention teaches a method for injecting a fluid substance into a subject, including: providing (1) a syringe pump system, including a motor assembly including (a) a housing, including a first end and a second end, (b) a motor, and (c) a rotatable drive shaft, wherein the motor is configured to cause the rotatable drive shaft to rotate, and the motor and rotatable drive shaft are at least partly contained within the housing; a carpule assembly including (a) a first end including an elongated inlet port, (b) a second end including an elongated outlet port, and (c) a chamber disposed between and in fluid communication with the elongated inlet port and the elongated outlet port; an elongated plunger, including (a) a receiving end, (b) a body, and (c) a pushing end, wherein (1) the elongated plunger is configured to nest within the elongated inlet port, (2) the pushing end of the plunger is configured to form a substantially fluid-tight seal with the chamber, and (3) the rotatable drive shaft is configured to apply a drive force to the receiving end of the plunger, either directly, or indirectly through an intervening shaft, such that the plunger can be pushed in the direction of the outlet port, thereby expelling any fluid in the chamber; a cannula system, wherein the cannula system includes a delivery tube that includes a first delivery tube end and a second delivery tube end, and wherein (1) the first delivery tube end is connected to and in fluid communication with the second end of the carpule assembly, and (2) the second delivery tube end is connected to and in fluid communication with a hollow needle; and a medically useful fluid substance located within the chamber of the carpule; (2) inserting a portion of the hollow needle into the subject; and (3) pumping the medically useful fluid substance out of the chamber, through the delivery tube and hollow needle, and into the subject. In some embodiments, the hollow needle is inserted into the spinal cord of the subject. In certain embodiments, the cannula system includes a floating cannula system that includes a base cannula including a proximal end, a distal end, and a lumen; a floating cannula including a lumen, wherein (a) the floating cannula is configured to be at least partially contained inside the lumen of the base cannula, (b) the floating cannula includes a proximal end and a distal end that extend farther proximally and distally than the proximal end and distal end of the base cannula when engaged therein, and (c) the floating cannula is configured to move in a direction along a longitudinal axis of the base cannula when engaged therein; a distal stopper connected to the distal end of the floating cannula, wherein the distal stopper is configured and positioned to prevent movement of the distal stopper in the proximal direction past the distal end of the base cannula, when the floating cannula is engaged in the base cannula; and a proximal stopper connected to the proximal end of the floating cannula; wherein (1) the proximal stopper is configured and positioned to prevent movement of the proximal stopper in the distal direction past the proximal end of the base cannula; (2) the distance from the proximal stopper to the distal stopper is greater than the distance between the proximal and distal ends of the base cannula; (3) the hollow needle is connected to the distal end of the floating cannula; (4) the delivery tube is connected to the hollow needle, and (5) at least part of the length of the delivery tube is contained inside the lumen of the floating cannula and/or the lumen of the base cannula. In some embodiments, the floating cannula system further includes one or more support tabs connected to the base cannula. In certain embodiments, the floating cannula system further includes a connector removably attached to the support tabs. In certain embodiments, the floating cannula system further includes a stereotactic device including a guiding arm configured to be lowered into a surgical field, and wherein the connector is removably attached to the guiding arm of the stereotactic device. In some embodiments, the hollow needle of the floating cannula system includes a tissue stopper. In certain embodiments, the positions of the distal and/or proximal stoppers on the floating cannula may be changed. In certain embodiments, the support tabs of the floating cannula system include finger grips. In some embodiments, the connector of the floating cannula system includes one or more indentations configured to closely fit an end of one or more of the support tabs. In certain embodiments, the medically useful fluid substance injected into the subject's spinal cord includes cells. In certain embodiments, the cells are neural progenitor cells. In certain embodiments, the neural progenitor cells express glial cell line derived neurotrophic factor. In some embodiments, the subject has been diagnosed with a neurologic disease, neurologic trauma, cancer, or combinations thereof. In some embodiments, the subject is a human who has been diagnosed with amyotrophic lateral sclerosis (ALS).

In various embodiments, the invention teaches a kit that includes any of the syringe pump systems described above; and instructions for the use thereof to inject a substance into a subject.

In various embodiments, the invention teaches a system for injecting a therapeutic substance into a tissue site of a subject. In some embodiments, the system includes a stereotactic device including: a guiding arm configured to guide a medical instrument towards or away from the tissue site of the subject along a first axis; a positioning arm configured to position the guiding arm along a second axis perpendicular to the first axis; an attaching arm configured to attach the stereotactic device to an arm of a tissue retractor; and a connecting arm configured to connect the attaching arm to the positioning arm; wherein one or more of the guiding arm, positioning arm, and connecting arm are motorized and configured to be electronically controlled in order to adjust their relative positions. In certain embodiments, one or more of the guiding arm, positioning arm and connecting arm include sensors for sensing their positions relative to one another or a landmark on the subject. In some embodiment, the system further includes a computer configured to wirelessly receive input from one or more of the sensors and/or wirelessly control the position of one or more arms of the stereotactic device. In some embodiments, the system further includes a cannula system connected to the guiding arm of the stereotactic device, wherein the cannula system includes a hollow tube and a hollow needle connected thereto. In certain embodiments, the cannula system includes one or more sensors configured to sense the extent to which the hollow needle is inserted into the subject. In certain embodiments, the system further includes a syringe pump, wherein the syringe pump is attached to the stereotactic device, and wherein the syringe pump is connected to and in fluid communication with the hollow tube of the cannula system. In certain embodiments, the syringe pump includes one or more electronically controlled motors configured to pump the therapeutic substance through the hollow tube and hollow needle of the cannula system. In some embodiments, the syringe pump includes one or more sensors configured to sense the volume and/or flow rate of the therapeutic substance. In certain embodiments, the operation of the syringe pump motor is controlled by the computer system.

In various embodiments, the invention teaches a method for injecting a therapeutic substance into a tissue site of a subject, including: (1) providing a system for injecting the therapeutic substance into the tissue site of the subject, wherein the system includes (a) a stereotactic device including: (i) a guiding arm configured to guide a medical instrument towards or away from the tissue site of the subject along a first axis; (ii) a positioning arm configured to position the guiding arm along a second axis perpendicular to the first axis; (iii) an attaching arm configured to attach the stereotactic device to an arm of a tissue retractor; and (iv) a connecting arm configured to connect the attaching arm to the positioning arm; wherein one or more of the guiding arm, positioning arm and connecting arm are motorized, and configured to be electronically controlled to adjust their relative positions; (b) a cannula system including a hollow tube and a hollow needle connected thereto, wherein the cannula system is attached to the guiding arm of the stereotactic device; and (c) a syringe pump including a chamber which includes the therapeutic substance, wherein the syringe pump is connected to and in fluid communication with the hollow tube of the cannula; operating the stereotactic device to position the hollow needle of the cannula system into the tissue site of the subject; and (3) operating the syringe pump to pump the therapeutic substance through the hollow tube and hollow needle of the cannula system and into the tissue site of the subject. In some embodiments, one or more of the guiding arm, positioning arm and connecting arm of the stereotactic device further include sensors for sensing their positions relative to one another or a landmark on the subject. In some embodiments, the system further includes a computer configured to wirelessly receive input from one or more of the sensors of the stereotactic device and/or control the position of one or more arms of the stereotactic device. In some embodiments, the cannula system further includes one or more sensors configured to sense the extent to which the hollow needle is inserted into the subject. In some embodiments, the syringe pump further includes one or more electronically controlled motors configured to pump the therapeutic substance through the hollow tube and hollow needle of the cannula system. In some embodiments, the syringe pump further includes one or more sensors configured to sense the volume and/or flow rate of the therapeutic substance. In certain embodiments, the syringe pump and/or stereotactic device are operated electronically. In certain embodiments, the tissue site of the subject is the subject's spinal cord. In certain embodiments, the therapeutic substance includes neural progenitor cells. In various embodiments, the neural progenitor cells express glial cell line derived neurotrophic factor. In certain embodiments, the subject has been diagnosed with a neurologic disease, neurologic trauma, cancer, or combinations thereof. In some embodiments, the subject has been diagnosed with amyotrophic lateral sclerosis.

BRIEF DESCRIPTION OF THE DRAWINGS

Exemplary embodiments are illustrated in the referenced figures. It is intended that the embodiments and figures disclosed herein are to be considered illustrative rather than restrictive.

FIG. 10 also shows rotating dial 101 causes motion of instrument attachment component 107 along the z-axis.

DETAILED DESCRIPTION OF THE INVENTION

Figure 1A:
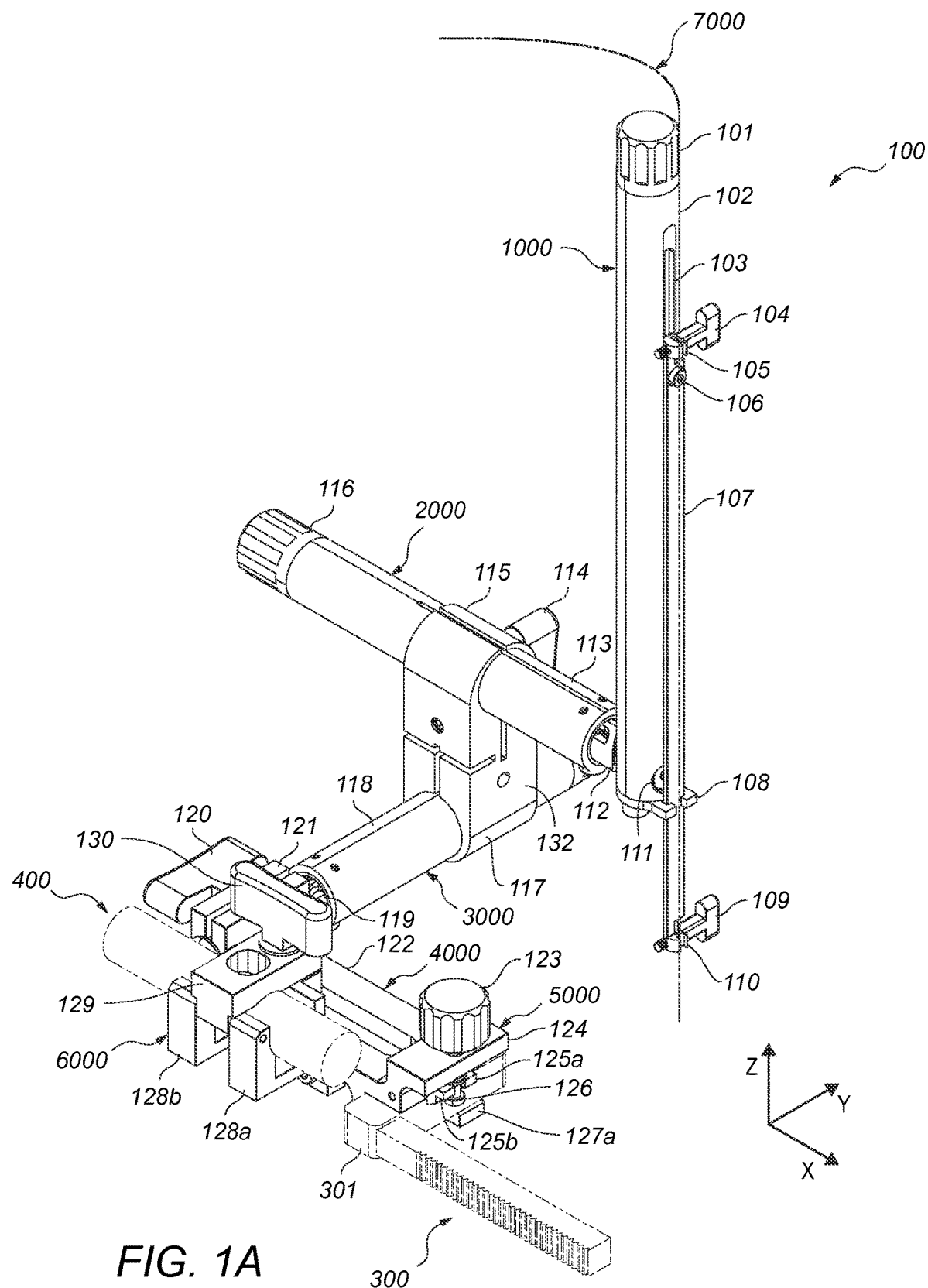
FIG. 1A depicts, in accordance with an embodiment of the invention, stereotactic apparatus 100. Stereotactic apparatus 100 is clamped to arm 301 of tissue retractor 300. Cylindrical object 400 is fastened to stereotactic apparatus 100 by side clamp 6000.
Figure 1B:
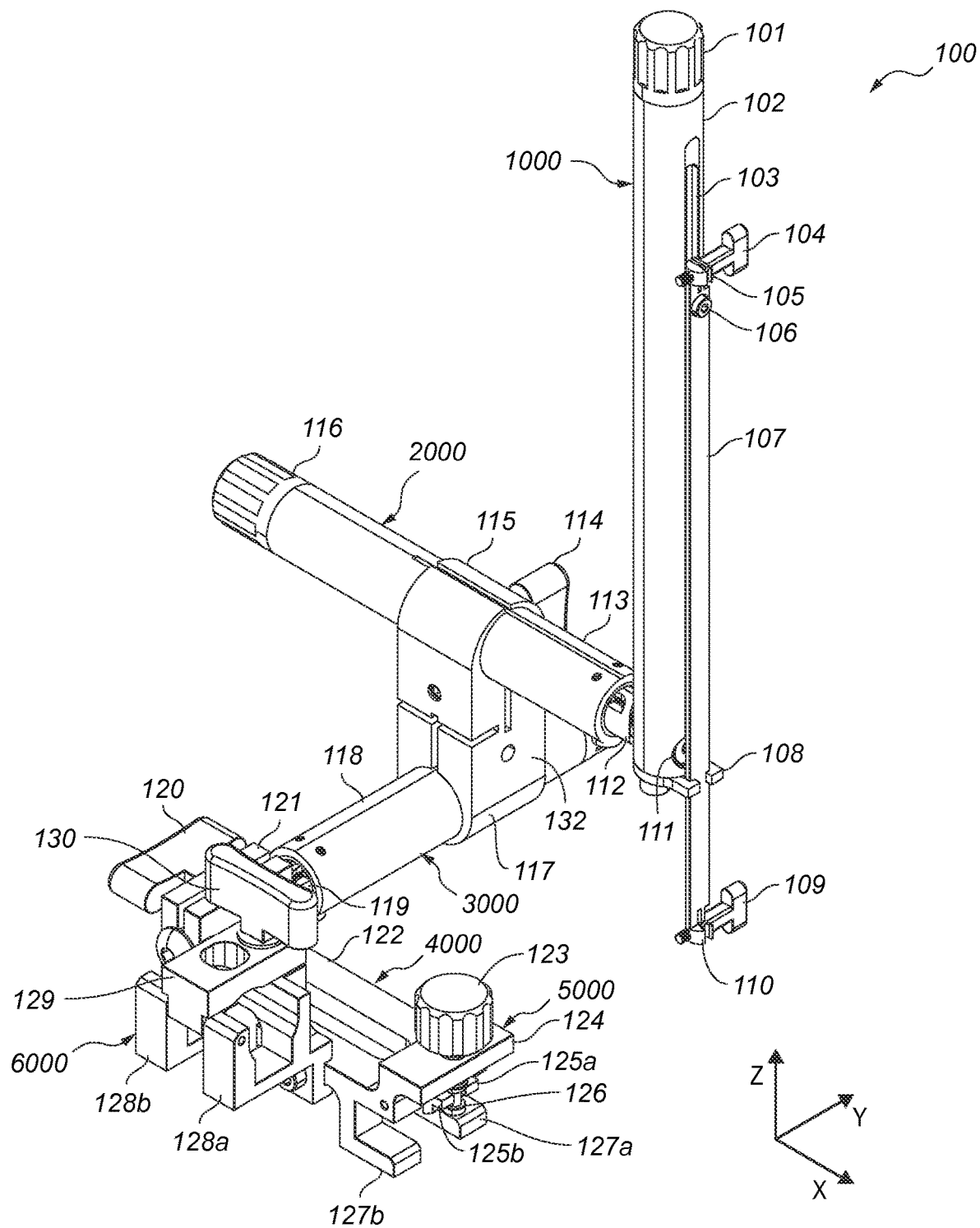
FIG. 1B depicts stereotactic apparatus 100 without attachment to a tissue retractor.

All references cited herein are incorporated by reference in their entirety as though fully set forth. Unless defined otherwise, technical and scientific terms used herein have the same meaning as commonly understood by one of ordinary skill in the art to which this invention belongs. *Szycher's Dictionary of Medical Devices* CRC Press, 1995, may provide useful guidance to many of the terms and phrases used herein. One skilled in the art will recognize many methods and materials similar or equivalent to those described herein, which could be used in the practice of the present invention. Indeed, the present invention is in no way limited to the methods and materials specifically described.

In some embodiments, properties such as dimensions, shapes, relative positions, and so forth, used to describe and claim certain embodiments of the invention are to be understood as being modified by the term "about."

The terms "patient" and "subject" are used interchangeably herein. These terms are intended to include all animal subjects, including mammals. Human patients/subjects are intended to be within the scope of the patients/subjects treated using the various embodiments of the inventive systems, apparatuses and methods described herein.

As used herein, the terms "anatomical feature" and "anatomical structure" include any tissue or collection of tissues found on or in a subject's body.

As used herein, the term "fluid," includes any fluid, including but in no way limited to a gas or a fluid.

As demonstrated herein, in some embodiments the invention discloses novel stabilizing apparatuses, cannula systems and apparatuses, syringe pump systems and apparatuses, and methods of use thereof. In some embodiments, the invention discloses imaging systems and methods that can be used alone or in conjunction with the aforementioned apparatuses, systems and methods. In some embodiments, the invention discloses automation of the aforementioned devices and systems through sensors, motors, receivers, transmitters and computers. While one of skill in the art would readily appreciate that there are many possible applications of the systems and apparatuses described herein, certain embodiments are especially useful for procedures performed on or around the spinal cord, including delivery of cutting edge cellular and molecular therapies thereto.

Although numerous embodiments of stereotactic apparatuses are described herein, there are certain features common to all of them. First, each stereotactic apparatus includes one or more components that make up a "securing section" capable of stably connecting to an arm of a tissue retracting device, or other support system (e.g. table, lamp, or any other solid object which can be clamped). The second feature common to each of the stereotactic apparatuses described herein is a "positioning section," which includes one or more components capable of positioning an instrument over a desired location in a subject's body. The third common feature is a "connecting section," which serves to operably connect the positioning section and the securing section. A fourth common feature is a "guiding section," which can be used to guide an instrument into or remove an instrument from a subject's body.

Provided below are descriptions of various components, combinations of components, and configurations of components relative to one another that can be used to arrive at each of the common sections described above. Additional features that can be added to the stereotactic apparatus are also described.

Securing Section

In some embodiments, the securing section of the stereotactic apparatus is configured to removably attach to an arm of a tissue retractor, or any device of similar dimensions. Removable attachment can be accomplished in any of a number of ways, using a wide range of components and combinations thereof. Merely by way of non-limiting examples, the securing section could attach to the arm of a tissue retractor by using one or more clasps, one or more clamps, one or more magnets, one or more screws, one or more pins, one or more slot and groove arrangements, one or more straps, combinations thereof and the like. Therefore, each of these components, and modified versions thereof, are within the scope of the invention. It is further contemplated that the attaching portion of the apparatus could be configured to attach to any of a variety of types of equipment that might be found in a setting in which a medical procedure is performed, including, but in no way limited to a table, a lamp, a brace, a tray, imaging equipment, and the like. It is also contemplated that the device could be configured for use in a non-surgical setting, in which it may be used to perform any objective that requires the use of precision guidance. It is further understood that the device could be scaled up or down in size appropriately for such objectives. Thus, the device could be configured to be an appropriate size for precision delivery of items on a microscopic scale (e.g., injecting a substance into a cell), or it could be configured to be an appropriate size to position or deliver much larger items.

Figure 3:
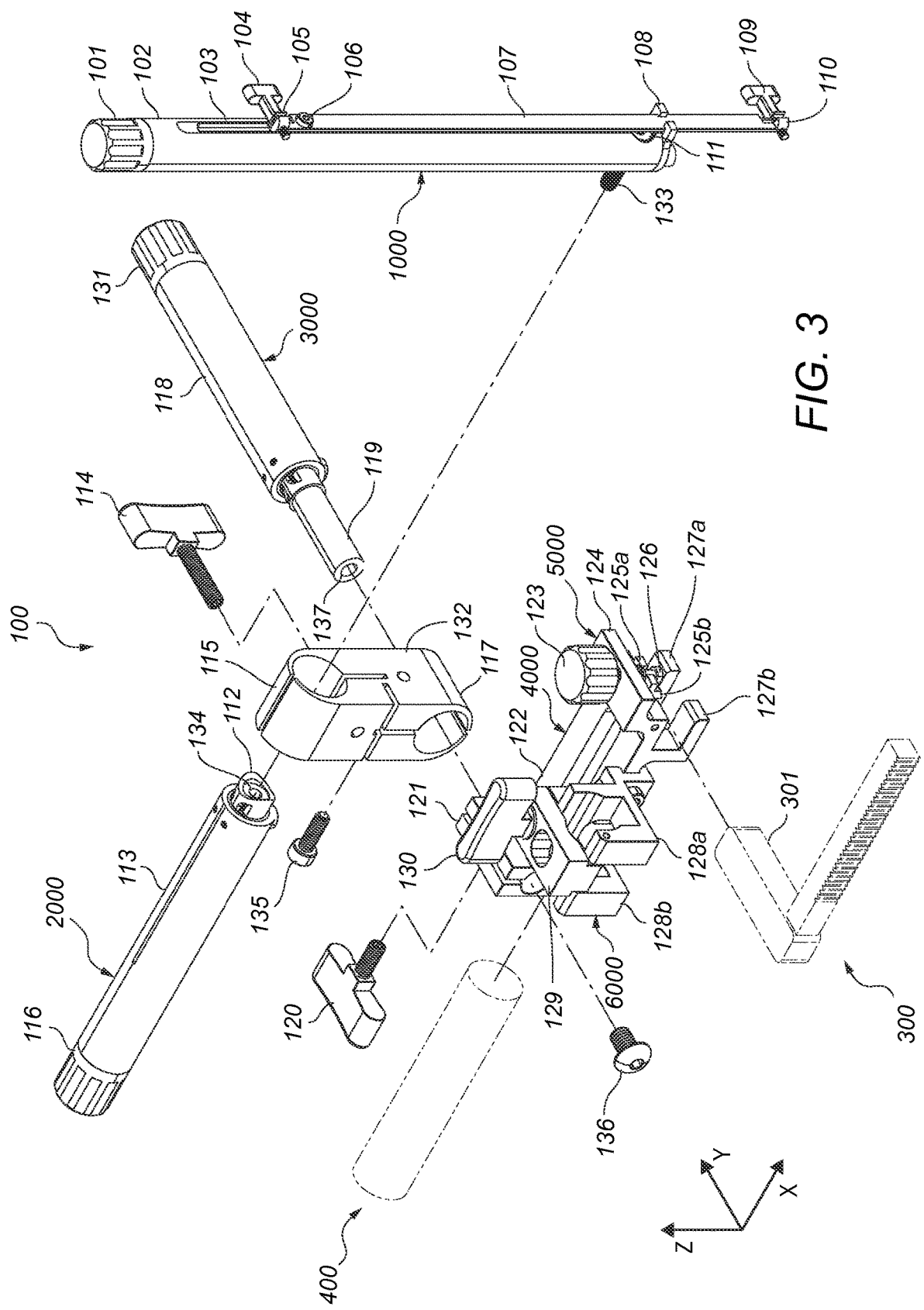
FIG. 3 depicts, in accordance with an embodiment of the invention, a partially exploded view of stereotactic apparatus 100.

In some embodiments, a clamping mechanism is incorporated on the securing arm, and used to attach the stereotactic apparatus to the arm of a tissue retractor. One of skill in the art would readily appreciate that numerous types of clamping mechanisms are suitable to accomplish this function. One non-limiting example is depicted in FIG. 3, which shows clamping mechanism 5000 of securing arm 4000 can be used to clamp arm 301 of tissue retractor 300 (partially shown). A more detailed view of the clamping components of this particular embodiment is shown in FIG. 21, and the individual components (and their functions) are thoroughly described in the examples section.

Figure 21:
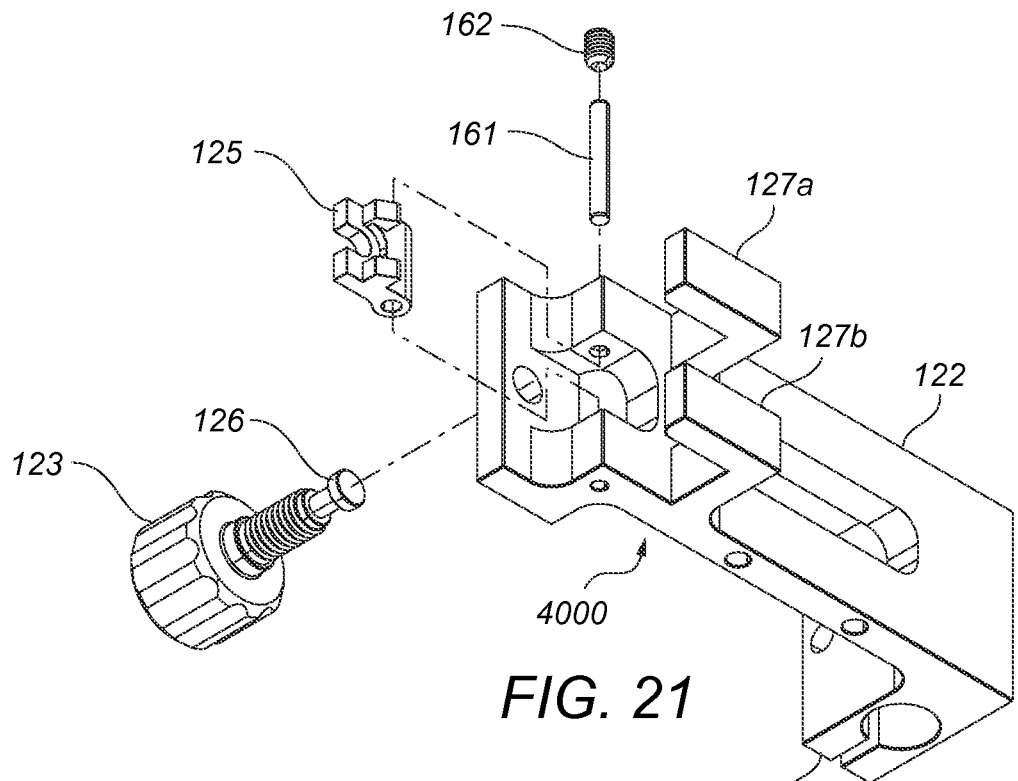
FIG. 21 depicts, in accordance with an embodiment of the invention, an alternate exploded view of securing arm 4000.

Importantly, the clamping mechanism shown in FIG. 21 can be used to securely and removably attach a stereotactic apparatus (including stereotactic apparatus 100) to the arm of a number of different types of tissue retractors. Non-limiting examples of retractors to which the clamping mechanism can attach include the Mast Quadrant Retractor System (Medtronic), the MARS Retractor System (Globus Medical), the Spyder Retractor System (Aesculap), the Ravine Refractor System (K2M), the Synframe Retractor System (DePuy Synthes), and the Luxor Retractor System (Stryker). One of skill in the art would readily appreciate that any retractor with one or more arms similar to those retractors described above could also be used in conjunction with the inventive stereotactic apparatuses described herein. One of skill in the art would further appreciate that the alternative attaching mechanisms (such as clamps, clasps, and similar mechanisms) described above would allow for the attachment of the securing section of an apparatus to one or more arms of alternative retractor devices that are not specifically listed above. Similarly, the securing section of the stereotactic apparatus can include an attaching mechanism of a suitable shape, size and orientation for attaching the stereotactic apparatus to a device other than a tissue retractor, without significantly affecting the function of the remainder of the device.

Positioning Section

Figure 15:
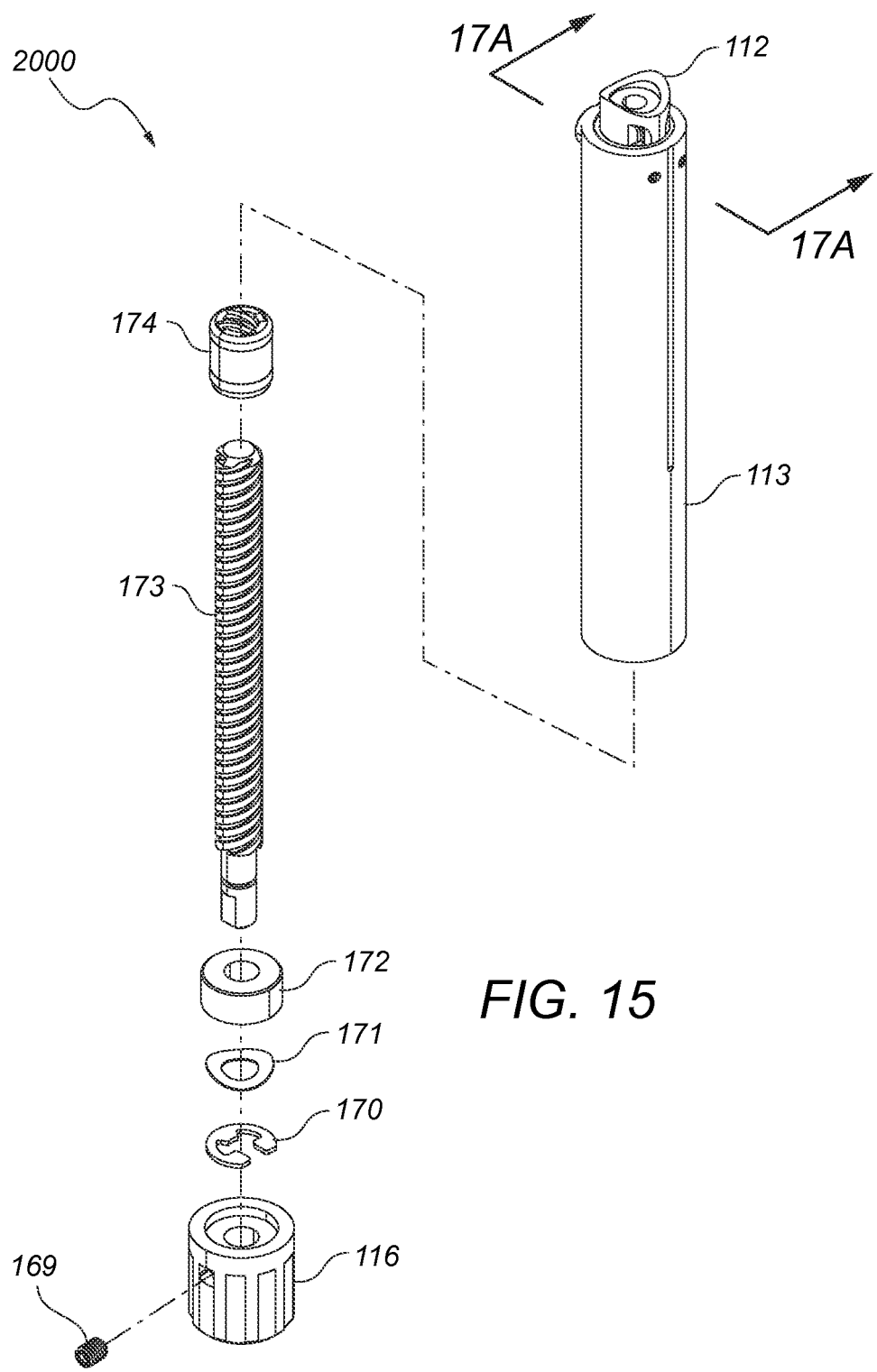
FIG. 15 depicts, in accordance with an embodiment of the invention, a partially exploded view of positioning arm 2000. Arrows labeled "17A" indicate the cross section represented in FIG. 17A.
Figure 16:
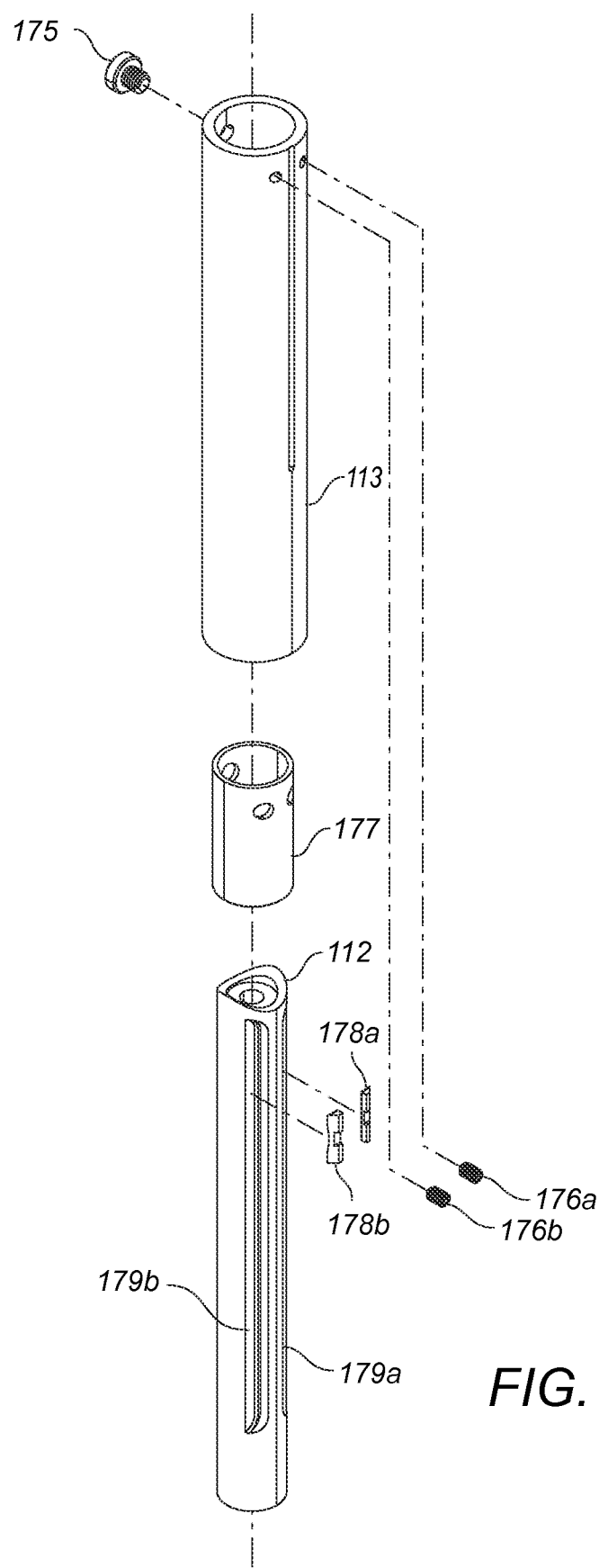
FIG. 16 depicts, in accordance with an embodiment of the invention, a partially exploded view of a portion of positioning arm 2000.

In the context of medical applications, the purpose of the positioning section is to allow for stable positioning of an instrument over a desired anatomical location, by positioning a guiding arm to which the instrument is attached. There are many possible components and configurations thereof that could make up a positioning section of the stereotactic apparatus. In certain embodiments the positioning section includes components that allow for telescoping motion, which permits fine adjustment of the position of the instrument attached to the guiding arm. In some embodiments, a positioning arm is used. In various embodiments, the positioning arm includes two or more nested elements that are operably connected to one another as well as an input component (e.g., a dial) in a manner that allows for telescoping motion. In a non-limiting example, the telescoping motion is accomplished by the components depicted in FIGS. 15-17. The interaction between and operation of the specific components of FIGS. 15-17 are thoroughly described in the examples section.

There are numerous possible ways of stabilizing and controlling the telescoping motion of the positioning arm. Merely by way of non-limiting example, if a mechanism with a threaded shaft is used, as depicted in FIGS. 15-17, the number of threadings on the shaft and the pitch of the threadings can be used to dictate the degree to which the positioning arm telescopes in response to associated input (e.g. rotation of a dial). In certain embodiments, the positioning arm is stabilized through the use of components that limit its range of motion in all but the axis along which it is advanced or retracted. Merely by way of non-limiting example, FIG. 16 shows the configuration of guiding set screws 176a and 176b and supporting elements 178a and 178b is used to apply pressure on L-shaped tracks 179a and 179b of inner nested element 112 of positioning arm 2000. FIG. 16 also shows that screw 175 is positioned on the opposite side of set screws 176a and 176b, in order to add to the stability of inner nested component 112, especially while it is being extended or retracted. All of these components can help to improve precision while utilizing the device, which can be particularly important in a medical setting.

There are many possible ways of attaching the positioning arm to the guiding arm. As shown in FIG. 3, one way positioning arm 2000 can be connected to guiding arm 1000 is through the use of screw 133 that traverses the short axis of guiding arm 1000 and connects to grooved receiving socket 134.

Connecting Section

Figure 12:
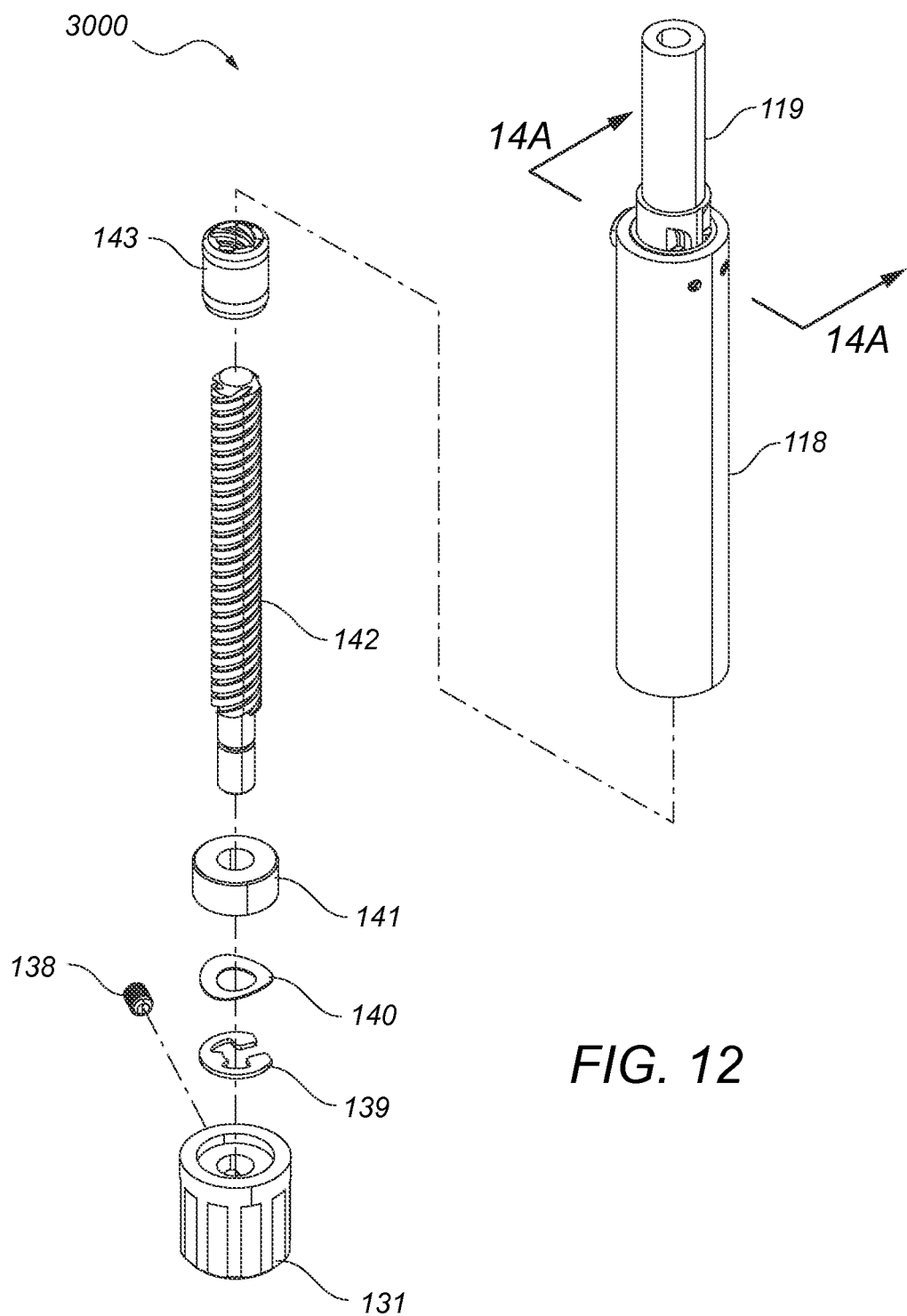
FIG. 12 depicts, in accordance with an embodiment of the invention, a partially exploded view of connecting arm 3000. Arrows labeled "14A" indicate the cross section represented in FIG. 14A.

The long axis of the connecting section of the stereotactic apparatus can be configured to be perpendicular to the long axis of the securing section and the positioning section. In some embodiments, the connecting section, like the positioning section, is a telescoping arm ("connecting arm"). In some embodiments, the telescoping connecting arm can be stabilized and controlled by any of the aforementioned components that can be associated with the positioning section, as described above. Merely by way of non-limiting example, telescoping of the connecting arm can be accomplished through the use of the components shown in FIGS. 12-14, the interaction between which and function of which are thoroughly described in the examples section.

Guiding Section

The guiding section can be configured to allow for the attachment of one or more instruments that can be extended into and retracted from a subject's body. In other embodiments, the guiding section can be useful for extending towards or retracting from another target, including in non-medical settings, as indicated above. In some embodiments, the guiding section includes a guiding arm. There are many possible ways by which an instrument can be attached to a guiding arm. One of skill in the art would readily appreciate that the possible components that could be used to attach an instrument to a guiding arm would vary depending upon the dimensions and nature of the instrument to be attached. Merely by way of non-limiting examples, attachment of various instruments to the guiding arm can be accomplished by using one or more straps, clamps, clasps, magnets, and combinations thereof.

Examples of instruments that could be attached to the guiding arm include, but are in no way limited to a cannula (including the floating cannula system described herein), a biopsy needle, a needle, a tube, a cauterization device, a laser, a drill, an endoscope, a guidewire, a fiberoptic device, an electrode, a saw, an ultrasonic device, a spectroscopic device, a camera, an electrical sensor, a thermal sensor, a catheter, a draining tube, an imaging device (such as any of those listed and/or described herein) and the like. In certain embodiments, the instrument guided by the inventive apparatuses described herein includes a guide needle and an injection needle configured to be concentrically housed therein. In some embodiments, the concentric arrangement of the guide needle and the injection needle allows the injection needle to be advanced through the guide needle, once the guide needle is properly positioned in a subject during a medical procedure, so that the injection needle can deliver a payload of biological or chemical material to an appropriate site in the subject. In some embodiments, the instrument guided and/or stabilized by the inventive apparatus is a spinal multisegmental cell and drug delivery device, such as the device described in U.S. patent application Ser. No. 12/598,667, which is incorporated by reference herein in its entirety as though fully set forth.

Figure 18:
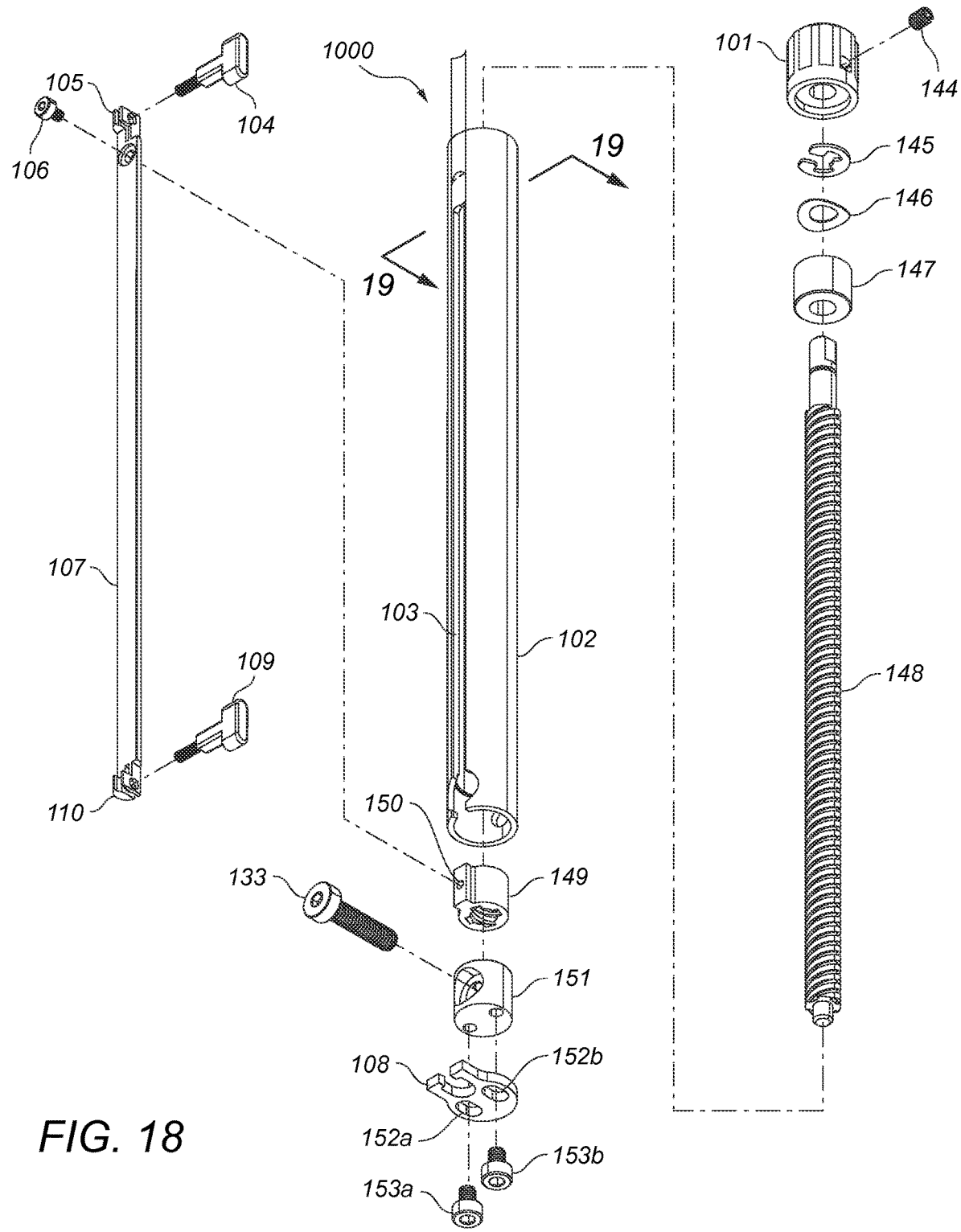
FIG. 18 depicts, in accordance with an embodiment of the invention, an exploded view of guiding arm 1000. Arrows labeled "19" indicate the cross section represented in FIG. 19.
Figure 19:
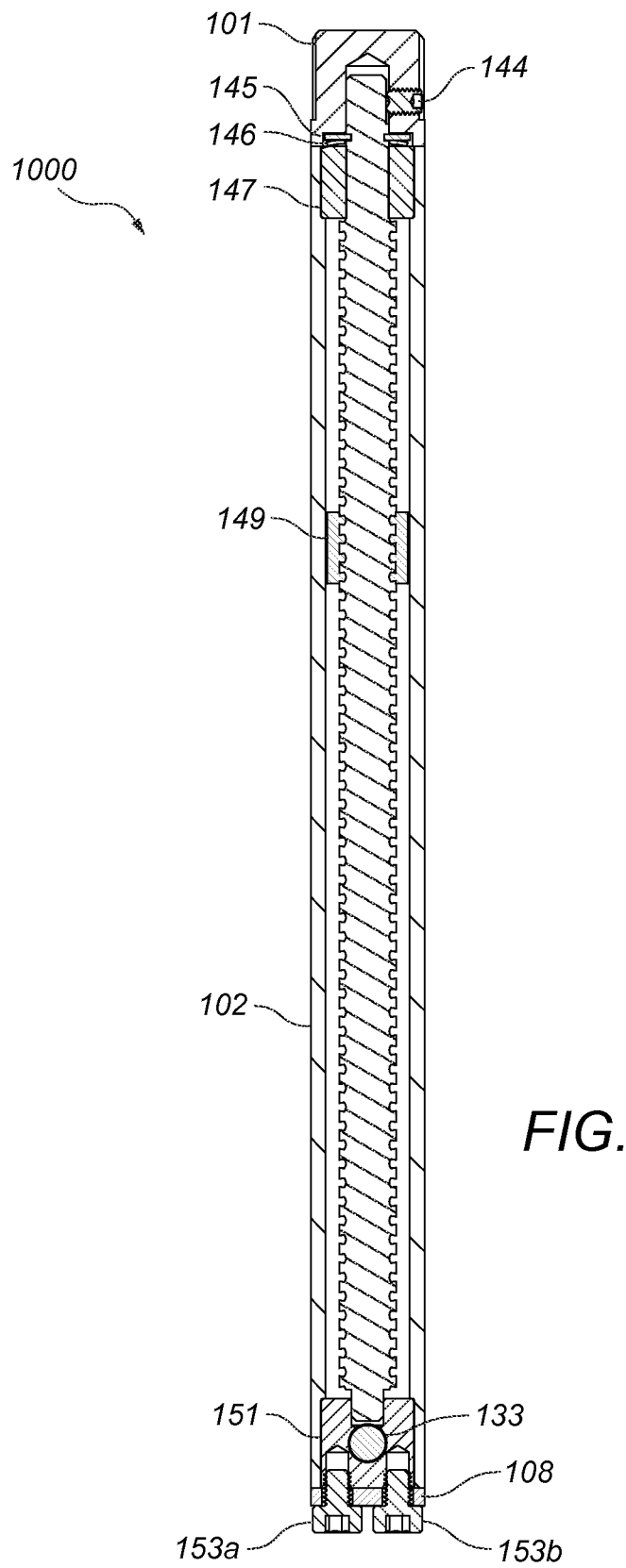
FIG. 19 depicts, in accordance with an embodiment of the invention, a cross-sectional view of the long axis of guiding arm 1000.
Figure 20:
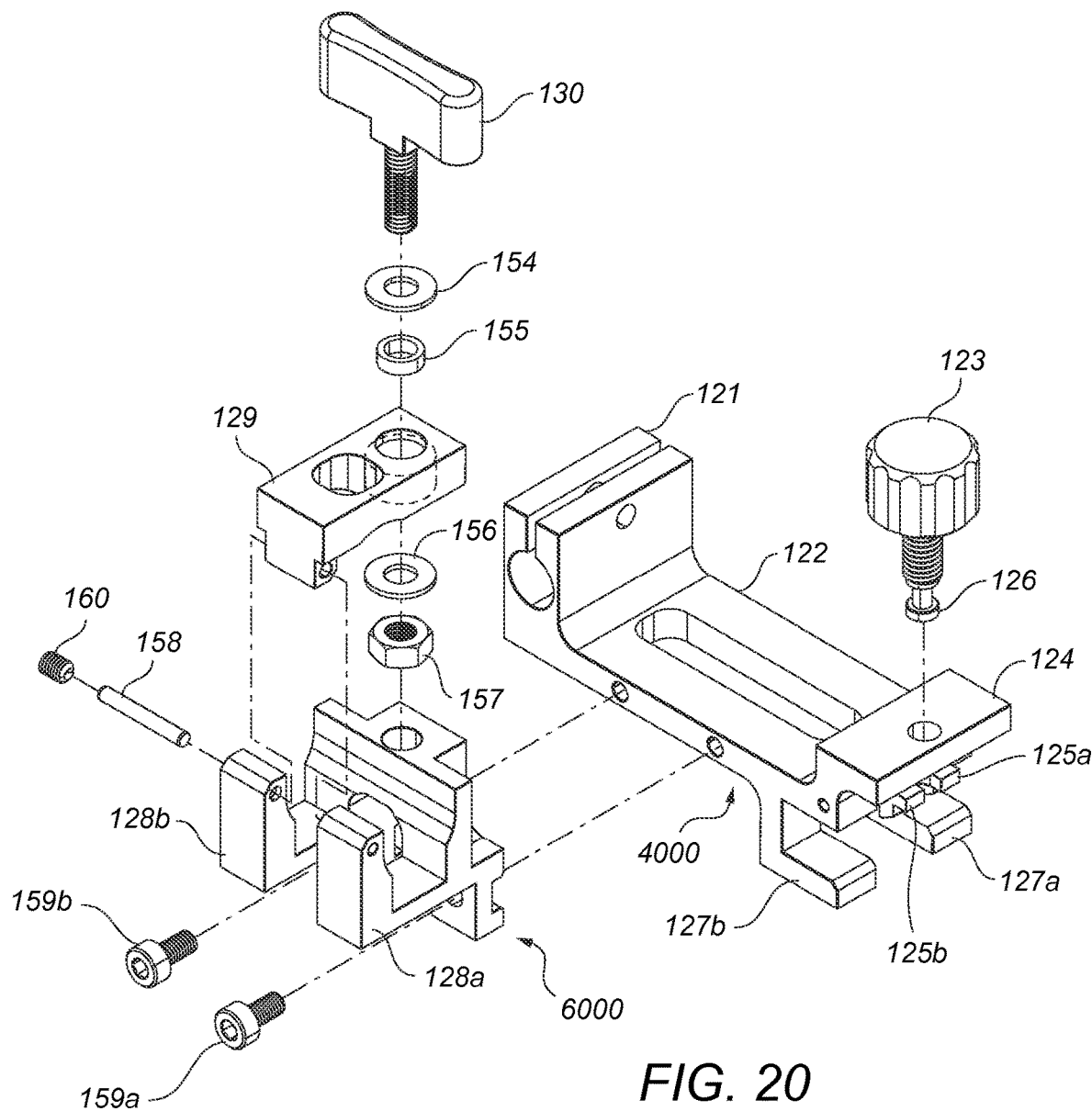
FIG. 20 depicts, in accordance with an embodiment of the invention, an exploded view of side clamp 6000, and it's attachment to securing arm 4000.

One of skill the art would also readily appreciate that there are numerous possible ways by which the apparatus can be configured to allow for an instrument to be extended into and retract from a subject, or other target, while connected to the guiding arm. FIG. 18 depicts one non-limiting example of a mechanism that can be used for that purpose. The association between the components shown in FIG. 18 and the function of those components are thoroughly described in the examples section.

Orientation of Individual Sections

Figure 5:
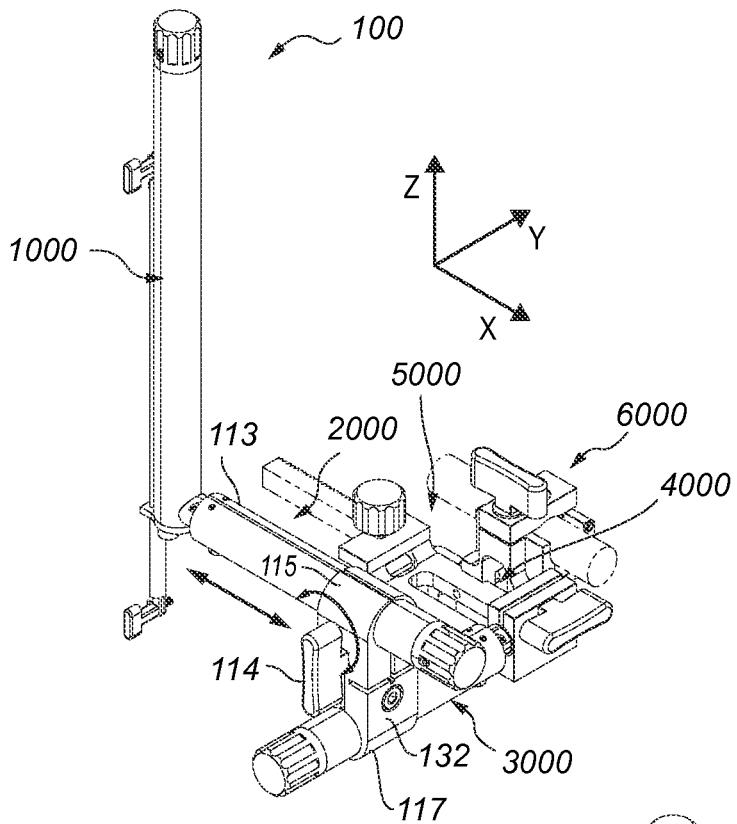
FIG. 5 depicts, in accordance with an embodiment of the invention, loosening knob 114 allows for adjustment of the position of positioning arm 2000 along the x-axis.
Figure 8:
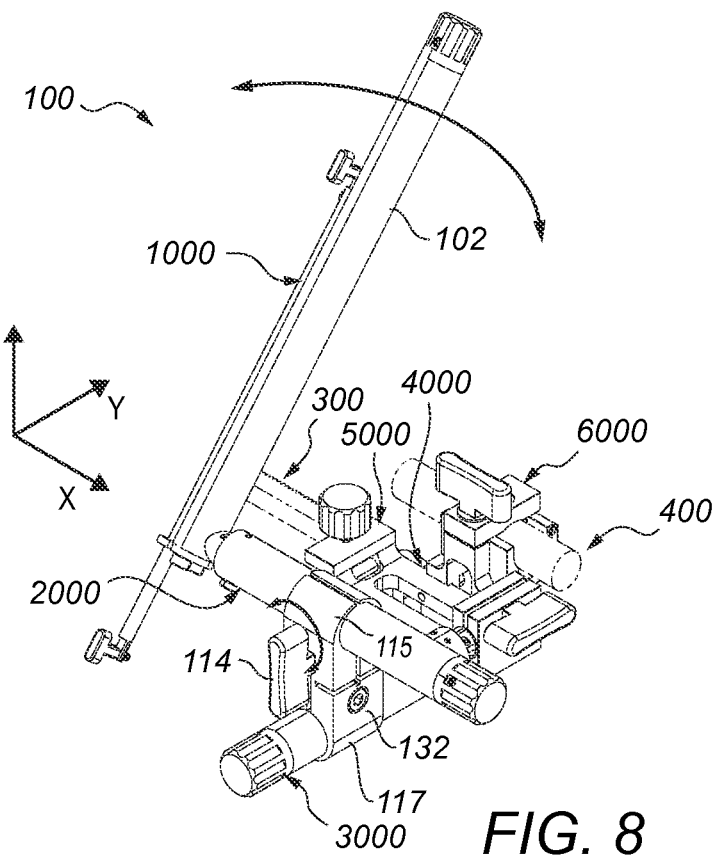
FIG. 8 depicts, in accordance with an embodiment of the invention, loosening of knob 114 allows for rotation of positioning arm 2000 around the x-axis and associated motion of guiding arm 1000 along the y-z plane.

The securing section, connecting section, positioning section and guiding section can be connected to one another by any of a variety of ways depending upon the desired range of motion of each section. In some embodiments, a perpendicular orientation of the positioning arm and connecting arm, relative to one another, is established through the use of a component with perpendicularly situated clamping collars. In an embodiment, cross clamp 132 (depicted in FIG. 1A) can be used. As shown in FIG. 5, when cross clamp 132 is used to secure positioning arm 2000, knob 114 can be rotated to loosen collar 115, thereby allowing for adjustment of the position of positioning arm 2000 along the x-axis. As shown in FIG. 8, loosening of collar 115 by rotating knob 114 also allows for rotation of positioning arm 2000 along the x-axis, which translates into motion of guiding arm 1000 along the y-z plane.

Figure 6:
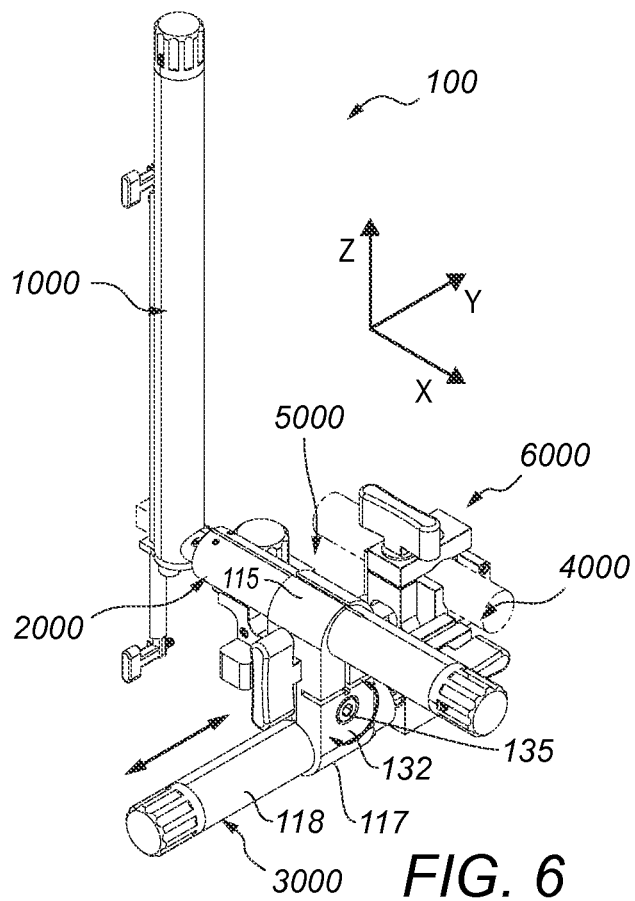
FIG. 6 depicts, in accordance with an embodiment of the invention, loosening screw 135 allows for adjustment of the position of positioning arm 2000 along the y-axis.
Figure 9:
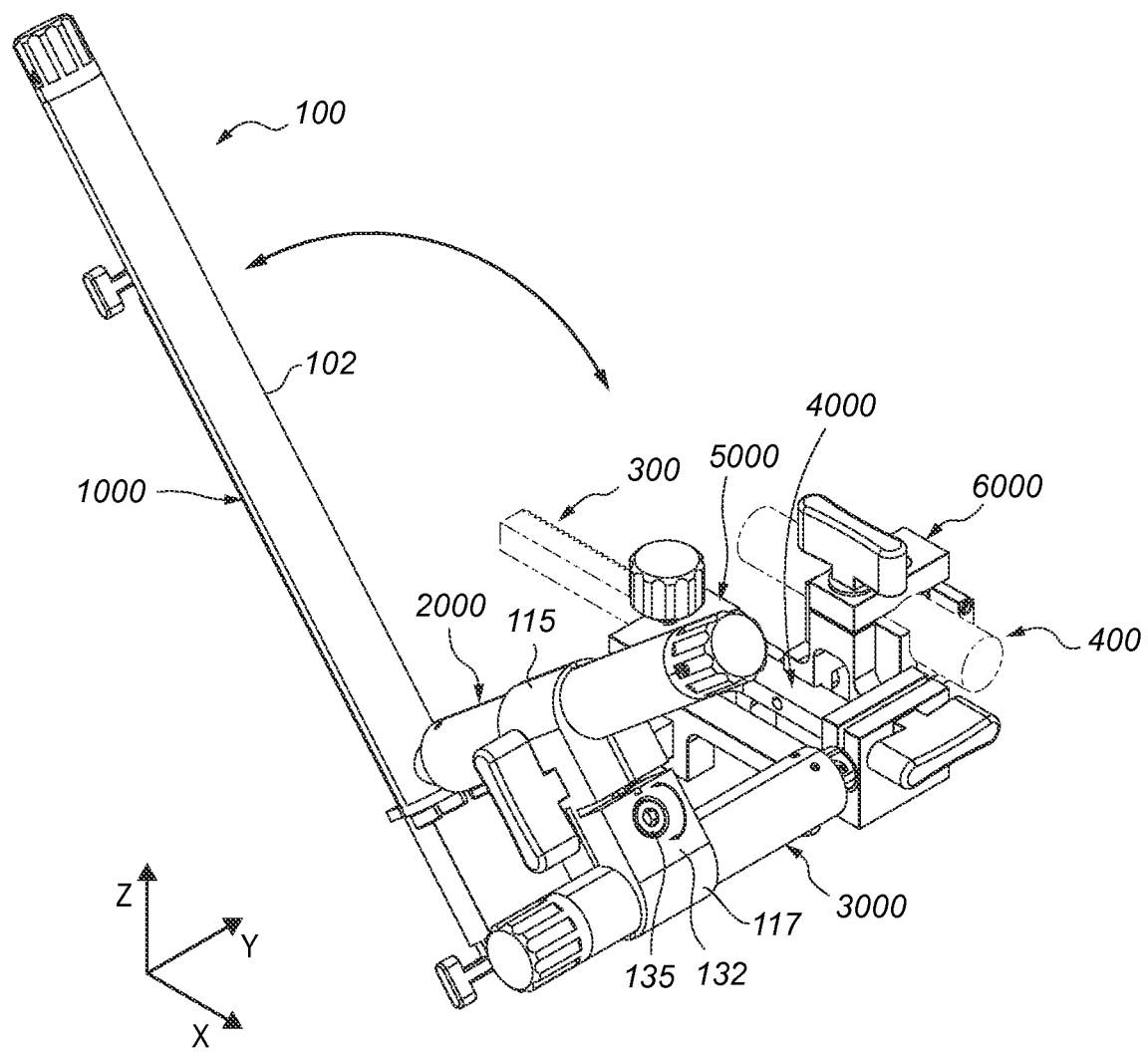
FIG. 9 depicts, in accordance with an embodiment of the invention, loosening screw 135 allows for rotation of cross clamp 132 around the y-axis, and associated motion of guiding arm 1000 along the x-z plane.

As shown in FIG. 6, when cross clamp 132 is used to secure connecting arm 3000, rotation of screw 135 loosens lower collar 117, which allows for adjustment of the position of positioning arm 2000 along the y-axis. As shown in FIG. 9, loosening collar 117 also allows for rotation of cross clamp 132 along the y-axis, which in turn translates into motion of guiding arm 1000 along the x-z plane.

Additional Features

The main sections of the stereotactic apparatuses described above can be configured to allow for incorporating additional features on the apparatuses. For example, the stereotactic apparatus can include clamps (or any other mechanism(s) of attachment described herein) situated on one or more of the main sections of the apparatus (i.e. guiding section, positioning section, connecting section, and attaching section) for attaching additional instruments or devices that are useful for a particular application.

Figure 22:
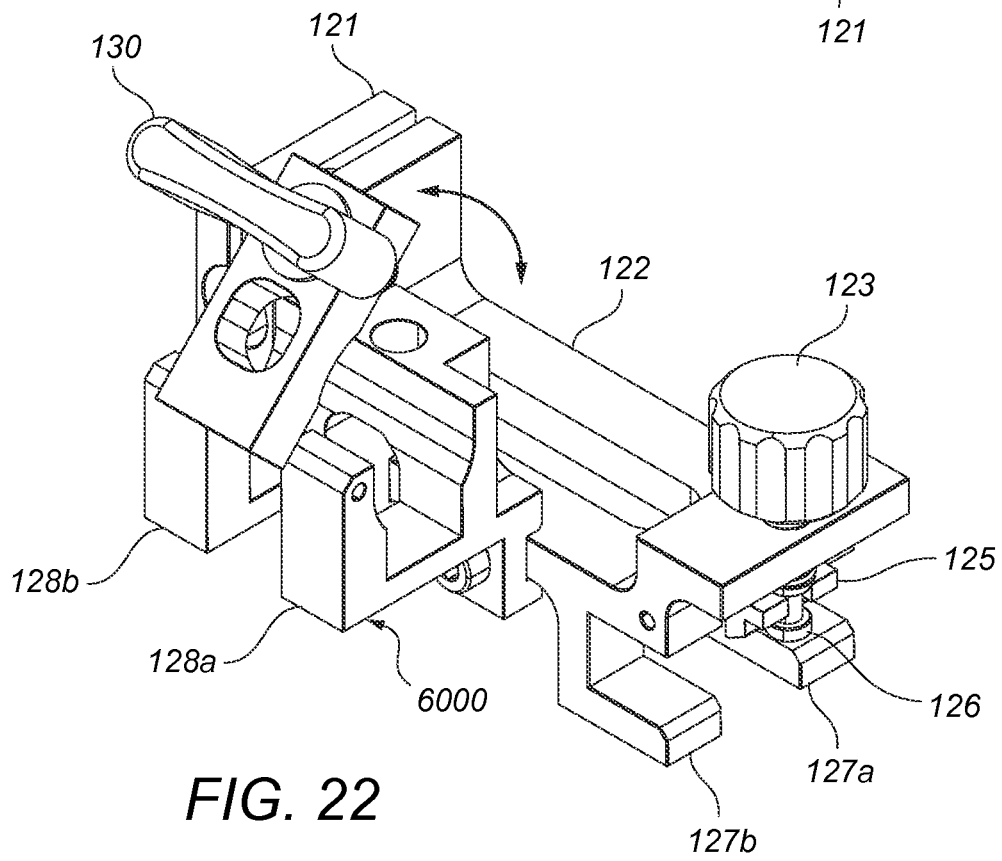
FIG. 22 depicts, in accordance with an embodiment of the invention, side clamp 6000.

In certain embodiments, the stereotactic apparatus includes a side clamp attached to the securing section, which allows for attaching a useful instrument or device. For example, as demonstrated in FIG. 3, side clamp 6000 can be used to hold cylindrical device 400. The components of a particular non-limiting embodiment (side clamp 6000) are clearly shown in FIG. 22, and thoroughly described in the examples section. One of skill in the art would readily appreciate that a side clamp such as side clamp 6000 can be used to attach any of a number of devices with appropriate dimensions to the stereotactic apparatus. Although the particular device 400 shown in FIG. 3 is cylindrical, a device of practically virtually any shape could be attached by appropriately modifying the shape and dimensions of the clamp (e.g. side clamp).

Devices that can be attached to the stereotactic apparatuses described herein can include, but are in no way limited to, a pump (such as the pump of the syringe pump system described herein), a reservoir for receiving a substance removed from a subject's body, a small motor, a control panel, an imaging device or portion thereof (including any appropriately sized imaging device described herein) and the like. In some embodiments, the device attached is a fiber optic camera, or portion thereof, that can be positioned to view an opening in a patient's body in which a tissue refractor is engaged. In some embodiments, a reservoir attached to the apparatus can be configured to hold any of a variety of useful substances, including but in no way limited to cells (including stem cells for various therapeutic treatments), fluids, medications, contrast agents, radioactive materials, combinations thereof, and the like.

An additional category of devices that could be attached to one or more sections of the inventive apparatuses described herein is a light source. In various embodiments, the inventive apparatuses may include one or more light sources configured to project light onto a region of interest on or in a subject's body during a medical procedure. In some embodiments, one or more of the light sources is attached to the guiding arm. In some embodiments, the light source is a laser. In some embodiments, the light source is a relatively high energy laser that can be used for cauterizing or cutting. In some embodiments, the light source is a relatively low energy laser that can be used for visually targeting a region on or in a subject's body for incision or other medical intervention. In other embodiments, the light source provides relatively low energy light for aiding in visualizing a region of interest. In still other embodiments, the light source provides light of a wavelength that causes fluorescence of a fluorophore. In various embodiments, the fluorophore is introduced into a subject's body directly, present in cells residing in a subject's body, or naturally occurring. Merely by way of non-limiting examples, the wavelength of the light projected by the light source can be in the visible, IR, or UV range.

Another category of devices that can be incorporated onto the stereotactic apparatuses described herein is an imaging modality. In some embodiments, the imaging modality is attached to the guiding arm. However, one of skill in the art would recognize that all or a portion of an imaging modality (or any other device described herein, or similar thereto) of an appropriate size could be attached to any arm of the apparatuses described herein, by any form of attachment described herein. In some embodiments, the imaging modality includes a device used to perform MRI, CT, or ultrasound imaging. In some embodiments, an endoscope is attached to the guiding arm. In some embodiments, one or more components of a microscope or other magnifying instrument are attached to the guiding arm. One of skill in the art would readily appreciate that any of a number of other useful instruments of a size suitable for attaching to the guiding arm could be used in conjunction with the inventive apparatuses described herein, and attached thereto by any means for attachment described herein.

As indicated above, in some embodiments, the apparatus is configured so that the positions of the various sections described above can be manipulated manually. However, one of skill in the art would readily appreciate that the apparatus could also be configured with one or more motors, gears, pulleys, and electronic controls, so that one or more sections of the apparatus could be electronically controlled.

In some embodiments, the apparatuses described herein, or one or more portions thereof, are made of stainless steel. In some embodiments, the apparatuses are made of titanium, austenitic steel, martensitic steel, brass, carbon fiber, plastic, composites, combinations thereof, and the like. In preferred embodiments, the material or materials used are biocompatible.

In some embodiments, the invention teaches a method that includes using any of the stereotactic apparatuses described herein for the purposes of facilitating one or more of the processes of (1) introducing a substance into a subject, (2) removing a substance from a subject, and (3) manipulating a portion of a subject's body. One of skill in the art would readily appreciate that the device could be used to introduce a substance into and/or remove a substance from any portion of subject's body, including, but in no way limited to an organ, joint (shoulder, hip, knee, etc.), ligament, tendon, muscle, eye, cavity, or any other tissue. In some embodiments, the apparatus can be used to introduce a substance into or remove a substance from a subject's brain. In some embodiments, the substances introduced into the subject's body can include but are in no way limited to biological and/or synthetic substances. Biological substances can include, but are in no way limited to stem cells, neural progenitor cells, tissues, blood, hormones, clotting factors, vectors (including but not limited to viral vectors, plasmids and the like), DNA, RNA, proteins, growth factors, inhibitory substances, matrices, combinations thereof, and the like. Synthetic substances that can be introduced into a subject's body can include but are in no way limited to pharmaceutical agents, markers (including but not limited to biomarkers or any other type of marker that could be visualized with or without the use of imaging equipment), implantable medical devices, electrical sensors, electrical stimulators (including devices for stimulating one or more portions of a subject's brain), glue, sutures, chemotherapeutics, radioactive substances, hyperpolarized substances, combinations thereof, and the like.

Substances that can be removed from a subject's body utilizing the inventive stereotactic apparatuses and methods include, but are in no way limited to, any of the above-named substances that can be introduced into a subject, in addition to tissues, organs, cancer cells and pre-cancer cells, bone marrow, fluid, foreign bodies, combinations thereof, and the like.

In some embodiments, the inventive method includes using any of the inventive apparatuses described herein to position any of the instruments described herein such that they can be introduced between the spreading elements of a refractor device described herein and then the adjacent sections of tissue associated therewith. In an embodiment, the inventive method includes using guiding arm 1000 of inventive apparatus 100 to introduce a needle associated with a cannula into any portion of a subject's spinal cord (including the section specifically described in the non-limiting examples herein). A payload of neural progenitor cells is then advanced through the cannula and needle and into the subject's spinal cord. In some embodiments, the neural progenitor cells express glial cell line derived neurotrophic factor (GDNF). In some embodiments, the subject has been diagnosed with a neural degenerative disease. In some embodiments, the neural degenerative disease is amyotrophic lateral sclerosis (ALS). In some embodiments, the subject has a neurologic injury. In some embodiments, one or more sections of the subject's spinal cord is damaged, severed, or partly severed.

In some embodiments, the invention teaches a method that includes (1) attaching any apparatus described herein to the arm of a retractor, (2) attaching any instrument described herein to the guiding arm of the apparatus (by any means described above), and (3) advancing the instrument through the separating elements of the retractor and into a subject's body through an incision in the subject's body. FIG. 1D shows a non-limiting example of how the components of an apparatus can be situated to perform this method.

Floating Cannula Instruments & Systems

In some embodiments, a guiding arm of any of the stereotactic devices described herein may be attached to any of the floating cannula systems described herein. The floating cannula system (or one or more components thereof) attached to a guiding arm may be utilized to perform precision injections (including injecting any medically useful substance, whether described herein or otherwise). Merely by way of non-limiting example, the cannula system and stereotactic device may be used when injecting a substance into the spinal cord, thus allowing a caregiver to accurately position the cannula and needle in the correct location.

Typically, once a needle is inserted into a subject's tissue, any movement of the subject with respect to the needle may damage the subject's tissue. This is particularly problematic for injections into sensitive areas, such as the spinal cord or brain, as damage to a spinal cord or brain could have severe consequences. For instance, if a stereotactic device lowered a needle into the spine, and the needle did not provide a stopping mechanism, or allow for movement along the longitudinal axis of the needle, a reflex (including but not limited to a cardiac or pulmonary reflex), twitch, or bucking of the patient could cause the needle to penetrate too far, or otherwise change directions and damage or sever spinal cord tissue (e.g. by shearing). This could have catastrophic consequences to a patient.

Therefore, in some embodiments the invention teaches a floating cannula system, with one or more components that can be used separately from or in conjunction with any of the stereotactic systems described herein. In some embodiments, the floating cannula can be attached to the guiding arm of a stereotactic device, thereby allowing for movement of the cannula in response to patient movement, once the needle has been inserted into the patient. In some embodiments, the system includes a floating cannula interacting with a base cannula, where the floating cannula may move up and down with respect to the base cannula to accommodate movement of the patient. The base cannula may be attached to a connector, which is in turn attached to a stereotactic device. This configuration can provide stability and support derived from the connector's attachment to the stereotactic device. In other embodiments, the base cannula may be attached directly to the stereotactic device. The base cannula may include two or more support tabs, such as the support tabs 402a and 402b depicted in FIG. 23, with holes that receive pins attached to the connector, such as the holes 417a and 417b depicted in FIG. 23. Additionally, the tabs may include finger pads for easy manipulation and handling of the cannula by a caregiver.

In some embodiments, the support tabs may include sockets (e.g. elements 417a and 417b of FIG. 23) for removably connecting to or mounting the support tabs onto pins that are supported by the connector. This will allow the tabs to hold the base cannula in place while allowing rotation about the pins. In some embodiments, the connector may include a locking member. Merely by way of non-limiting example, the connector 420 may include a locking member 418, as depicted in FIG. 24. In some embodiments, the support tabs may be rotated into recesses or spaces in the connector, and then the locking member may be moved to block the support tabs from rotating back out. Merely by way of example, FIG. 24 demonstrates recessed portions of connector 420 in which support tabs 402a and 402b are engaged and secured in place by locking member 418. In some embodiments, more than one locking member may be utilized to block the support tabs.

In some embodiments, the locking member is a physical restraint that creates an interference fit by rotating a handle that blocks the support tabs from rotating out of place. The locking handle may be rotated into place once the tabs are mounted on the pins, and then rotated into one or more slots on the connector. Accordingly, the base cannula, in some embodiments, may be rigidly attached to the stereotactic device through the connector. In other embodiments, the base cannula may attach directly to the guiding arm or other positioning section of a stereotactic device through tabs. In other embodiments, the stereotactic device may include pressure cuffs that attach directly to the round tube of the cannula. Ultimately, a variety of methods/devices may be utilized for attaching a base cannula to a stereotactic device, including one or more of any suitable type of attachment mechanism described and/or depicted herein.

A floating cannula may extend down from the base cannula that is supported by the stereotactic device. In some embodiments, the floating cannula will fit inside the lumen of the base cannula. In other embodiments, the base cannula will fit inside the lumen of the floating cannula. In both embodiments, the concentric fit allows the base cannula to contact the floating cannula while allowing the floating cannula to slide along a longitudinal axis of the base cannula and with respect to the base cannula. In some embodiments, the fit between the floating cannula and the base cannula will prevent the floating cannula from moving substantially in other directions, aside from along the longitudinal axis. In some embodiments, the floating cannula and base cannula may be connected to the stereotactic device through a hinged mechanism that allows for motion in a direction perpendicular to the longitudinal axis of the cannulas, in order to accommodate patient movement after the needle is placed.

In some embodiments, the floating cannula will run along the inside lumen of the base cannula and the floating cannula will be of a sufficient length to protrude on both sides of the base cannula. Additionally, the floating cannula may include stoppers situated such that they are positioned beyond each of the ends of the base cannula when the floating cannula is engaged therein. Merely by way of example, the stoppers may be configured according to the arrangement demonstrated in FIG. 26, in which stoppers 410a and 410b are located near the ends of floating cannula 404, such that they limit the range of motion of base cannula 406 when floating cannula 404 is engaged therein. In the configuration demonstrated in FIG. 27, the top (proximal) stopper 410a is shown fixed to the top (proximal) end of the floating cannula, and it prevents the floating cannula from falling down and out of the base cannula 406. FIG. 27 shows that by positioning lower stopper 410b at the distal end of the floating cannula, a needle 416 located at the bottom of the floating cannula can be inserted into tissue due to resistance from the base cannula 406 pushing on the lower stopper 410b, when a downward force is applied to the base cannula 406. Without the bottom stopper, or comparable element, the floating cannula could not provide sufficient pressure for inserting the needle into the anatomical target (e.g. spinal cord) of a subject, when the base cannula is lowered toward the subject.

In some embodiments, the floating cannula will contain a tissue stopper that is attached to a needle. The tissue stopper may be any suitably shaped material secured to the needle that will limit the depth of an injection when the tissue stopper makes contact with the tissue at the injections site. The tissue stopper may be positioned at any point along the needle, depending on the depth of injection required for a particular procedure. The tissue stopper may be any of a number of shapes, including but in no way limited to flat, wedge-shaped, ball-shaped, and cup-shaped. Any suitable shape which provides a mechanical means to limit how far a needle injects into a tissue site (e.g. the spinal cord) is within the scope of the invention. Merely by way of example, the tissue stopper may be configured according to the embodiment of FIG. 27, which shows tissue stopper 412 positioned between needle 416 (positioned at the end of the floating cannula) and lower stopper 410b.

In some embodiments, the floating cannula will fit inside the base cannula, and thus the stoppers may be positioned on the floating cannula, so that they contact the proximal and distal rims of the base cannula and prevent the floating cannula from moving past certain points with respect to the base cannula. In other embodiments, the floating cannula may fit on the outside of the base cannula (the base cannula would run at least partially inside the lumen of the floating cannula) and may have internal and/or external stoppers. In some embodiments, there will also be space for attaching the base cannula to the stereotactic device through the floating cannula. In some embodiments, the floating cannula will fit inside the base cannula and protrude on both sides of the base cannula. In other embodiments, the base cannula will fit inside the lumen of the floating cannula, and the floating cannula will only cover a distal portion of the base cannula. In this embodiment, other stoppers or movement restriction systems may be utilized to limit the travel of the floating cannula with respect to the base cannula. For example, the base cannula may include a slot, along which a tab connected to the inside lumen of the floating cannula, would ride. The tab may contact another tab on the inside of the lumen of the base cannula that is configured to contact the tab from the floating cannula.

In some embodiments, a delivery tube connected to a fluid reservoir will run the entire length of the cannula system and terminate at a hollow needle. In some embodiments a section of the delivery tube is located outside of the floating and base cannulas, and a section of the delivery tube is contained within the lumen of the floating cannula (a portion of which is contained within the base cannula). In some embodiments, the delivery tube is in fluid communication with a hollow needle located at the end thereof. Thus, in some embodiments, a fluid can be introduced through a first end of the delivery tube located outside of the cannula. The fluid could then be advanced through the entire delivery tube (including a portion contained within the floating cannula) until it exits a hollow needle at the end thereof. In some embodiments, the delivery tube is in fluid communication with a fluid reservoir. In some embodiments, the fluid reservoir is connected to a fluid pump (including any suitably sized fluid pump, such as the fluid pumps described herein). In some embodiments there may be an external (or internal) pump and reservoir that contain a therapeutic or other injectable substance for injecting into a tissue site (or other location in a subject). The non-limiting example of FIG. 27 depicts a delivery tube 408 nested within the floating and base cannulas, and terminating in hollow needle 416.

In some embodiments, the invention includes a procedure for injecting a substance into a subject using a floating cannula system and stereotactic device described herein. This procedure may include attaching the floating cannula system to the guiding arm of a stereotactic device (through any mechanism/means described herein). Then, the cannula will be advanced towards an injection site by advancing the guiding arm of the stereotactic device. In some embodiments, the hollow needle associated with the cannula will contact the injection site (e.g. the spinal cord) and pressure will push the floating cannula proximally into the lumen of the base cannula. The floating cannula will continue to move proximally until the stopper on the bottom portion of the floating cannula contacts the distal end of the base cannula. Then, the distal end of the base cannula will apply pressure to the stopper, which will be transferred to the floating cannula. Thereafter, the pressure will push the needle into the injection site. In some embodiments, the needle will be inserted until the tissue stopper makes contact with the tissue at the injection site (e.g. the spinal cord). Once the needle is inserted into the tissue, the friction from the tissue on the needle and potentially the negative pressure from the injection site on the needle will hold the needle in place such that it is situated in the direction of the longitudinal axis of the cannulas.

In some embodiments, once the needle is fully inserted into the injection site (as limited by the tissue stopper), the guiding arm of the stereotactic device may be retracted from the injection site, so that the base cannula also moves away from the injection site, and upward with respect to the floating cannula and the needle. This will create space between the distal stopper of the floating cannula and the distal end of the base cannula, which will allow movement of the floating cannula along the longitudinal axis of the cannulas. This freedom of movement will accommodate movement of the subject in whom the needle is inserted (e.g. movement from respiration, heartbeat, bucking, and the like). Accommodation of movement is particularly important in procedures requiring injecting into delicate areas (e.g. the spinal cord), as a sudden force along the longitudinal axis of the needle has the potential to cause the needle to puncture further into the subject and cause considerable damage, depending on the local organs or other anatomical structures in the needle's path.

One of skill in the art would readily appreciate that one or more components of the floating cannula systems described herein could be utilized independently from the stereotactic device described herein. Thus, various combinations of the individual components of the cannula systems described herein are within the scope of the present invention.

Syringe Pump

In various embodiments, the invention teaches a syringe pump system that can be used to facilitate the precision injections described herein above, as well as for other purposes. In certain embodiments, the syringe pump system may be configured to attach to a stereotactic device, including any of the stereotactic devices described herein. In some embodiments, the syringe pump system is configured to be secured by the side clamp of a stereotactic device described herein. Although the figures (for example FIG. 37) depict a syringe pump system oriented in one direction relative to the stereotactic device, the syringe pump systems described herein can also be oriented in the opposite direction relative to the stereotactic device. In addition, the syringe pump systems described herein may be configured to interact with and attach to (permanently or removably) any of the cannulas and cannula systems described herein, including the floating cannula systems described herein, whether for the purpose of facilitating the injection of a therapeutic substance into a subject (as described herein), or otherwise. Further, the syringe pump systems described herein may be utilized as stand-alone devices, or they may be coupled with an appropriately sized fluid inlet of practically any fluid delivery system, especially those used in medical applications.

The syringe pump systems described herein all include the following central components: (a) a carpule with an interior chamber configured to hold a quantity of a therapeutic substance or other medically useful substance, (b) a plunger configured to interact with the interior chamber of the carpule and advance therein in order to expel a therapeutic substance (or other medically useful substance) therefrom, and (c) a motor for imparting a drive force (either directly, or indirectly through one or more drive shafts, or other components useful for translating mechanical force) to the plunger. In some embodiments, the syringe pump systems described herein may be utilized to deliver therapeutic agents, such as stem cells (including but not limited to any type of stem cell described herein), pain medications, chemotherapeutic agents and/or other medications (along with any other medically useful substance or combination of substances described elsewhere herein), safely, by regulating fluid dynamics and monitoring flow pressure during injection. In preferred embodiments, the size of the syringe pump system may be such that it does not significantly encumber the surgical space for the procedure in which it is utilized. As such, the syringe pump system may be configured to be a small hand-held device and/or a stand-alone pump that may be utilized in surgical procedures that do not require a stereotactic system.

Figure 31:
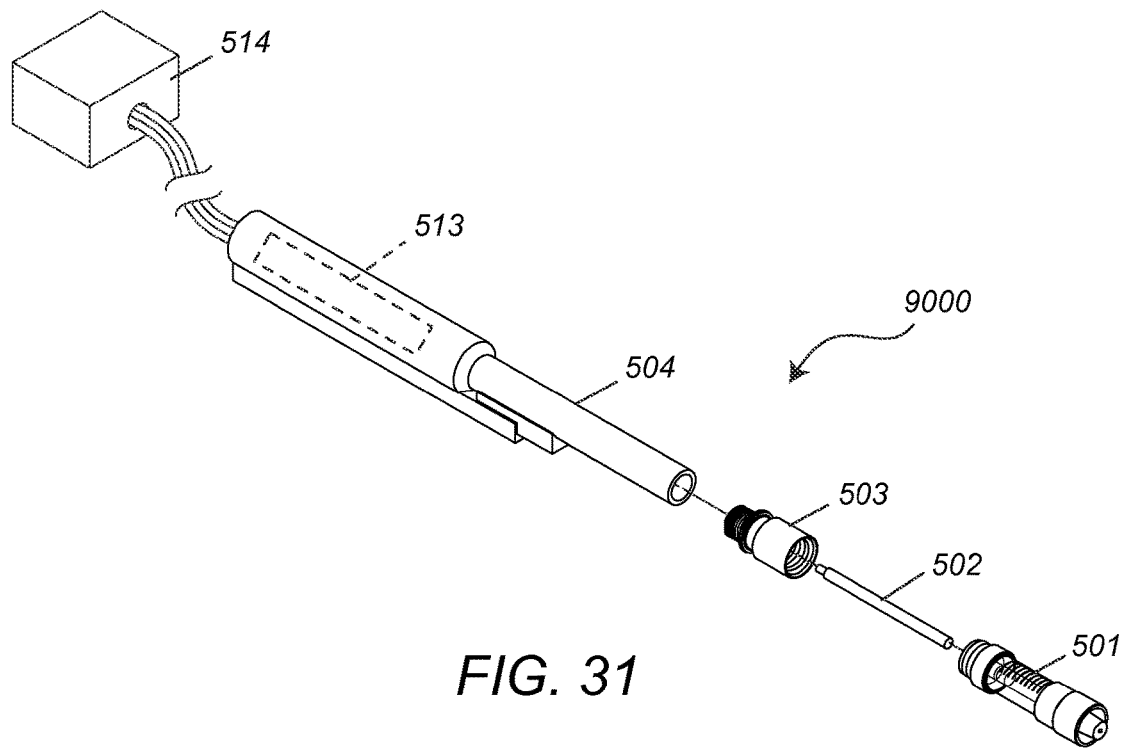
FIG. 31 depicts, in accordance with an embodiment of the invention, a partially exploded view of syringe pump 9000.

With regard to the carpule component, in certain embodiments the carpule may be configured as a disposable component that is removably coupled to the syringe pump. In some embodiments, the carpule component may contain a therapeutic agent (or other medically useful substance) with a predetermined amount and/or dosage to be injected into a specific anatomical location and/or tissue (e.g. spinal cord, brain, tumor tissue, etc.). A non-limiting example of a syringe pump system 9000 including a carpule 501 is shown in FIG. 31.

In certain embodiments, the carpule is made of one or more sterilizable materials (e.g. glass, plastic, metal, etc). In some embodiments, the carpule has an interior chamber with a volume of 50 ul. In some embodiments, the carpule may have an interior chamber with a volume of 100 ul, 250 ul, 500 ul, or more. In various embodiments, the volume of the chamber may be from 20 ul to 10 ml or more. The size of the carpule and volume of its interior chamber may be configured to be appropriate to accommodate a volume and dosage of a therapeutic agent (or other medically useful substance) needed for a particular application/procedure. In certain embodiments, the interior chamber is cylindrical, but other shapes are possible and within the scope of the present invention. In certain embodiments, the carpule is removably coupled (directly or indirectly) to a component including a motor and drive shaft and/or plunger. In some embodiments, the carpule is configured to be prefilled with a therapeutic agent (such as any type of cellular therapeutic composition or other therapeutic composition described herein) prior to use. In some embodiments, the carpule may be removably coupled to the syringe pump, so that it may be sterilized before and/or after use in a medical procedure (e.g. by gamma radiation, EtO, etc.). In some embodiments, the syringe pump system may also include a mechanism to rotate and/or vibrate the carpule component, in order to reduce or avoid settling, clogging and/or clumping of the therapeutic agent (e.g. cells). In some embodiments, the interior of the carpule may be coated with a substance known to prevent cells from adhering or sticking to the interior surface. In some embodiments, the interior of the carpule may be coated with heparin and/or hydrophobic coatings. In some embodiments a plasma treatment may be used on the interior of the carpule. In some embodiments, the interior geometry of the carpule is configured in such a way as to prevent agglomeration of the cells, such as large aspect ratio pathways, tortuous pathways and/or a series of parallel passageways. In some embodiments, the syringe pump system is configured to deliver a therapeutic agent via a microfluidic flow process.

Merely by way of non-limiting examples, the interior chamber of the carpule may be smooth, rigid, and/or contain grooves. In certain embodiments, the carpule may be designed such that it has a cone-shaped interior, in order to facilitate fluid flow out of the carpule. By way of non-limiting examples, the cone-shaped interior may be smooth, rigid, and/or contain grooves. In some embodiments, the carpule may contain markings on the interior or exterior surface. The markings may allow the user to determine how much volume of a substance has been loaded in and/or expelled from the carpule. In some embodiments, the carpule includes a window made of glass, plastic, or another transparent or semi-transparent material that allows the substance in the chamber to be viewed.

In certain embodiments, the carpule includes (a) a first end including an elongated inlet port, (b) a second end including an elongated outlet port, and (c) a chamber disposed between and in fluid communication with the elongated inlet port and the elongated outlet port. In some embodiments, the chamber, elongated inlet port and elongated outlet port are approximately the same size (i.e. diameter). In other embodiments, these sections of the carpule are different sizes. In some embodiments, the inlet port and/or outlet port are not elongated, and are instead of another shape useful for a specific fluid delivery application.

Turning now to the plunger component, in some embodiments the plunger is elongated and it includes a receiving plunger end, a pushing plunger end, and an elongated plunger body. In some embodiments, the plunger is configured to nest within the first elongated inlet port of the carpule. In certain embodiments, the pushing end of the plunger is configured to form a fluid-tight seal with the interior chamber of the carpule. In some embodiments, the receiving plunger end is configured to receive pressure from a drive shaft attached to the motor, such that the plunger is advanced along the interior chamber of the carpule, thereby expelling fluid contained in the chamber. In other embodiments, the plunger is otherwise directly or indirectly attached to the motor, and configured to advance along the chamber of the carpule in response to input from the motor.

With regard to the motor of the syringe pump system, in certain embodiments the motor (e.g. element 513 in FIG. 31) is contained within a housing (e.g. element 504 in FIG. 31). In some embodiments, the syringe pump is connected to a control box (e.g. element 514 in FIG. 31), which electronically controls the flow of fluid pumped by the syringe pump (rate, duration, volume, etc.). As indicated above, the motor of the syringe pump may be connected to a drive shaft for imparting a drive force on the plunger, thereby causing the plunger to advance along the interior chamber of the carpule and expel a therapeutic or other medically useful substance contained therein.

Although the syringe pump can be connected to a control box (or other controller) via wires (as shown in FIG. 31), a wireless connection to the control box/controller is also within the scope of the present invention, and can be accomplished utilizing any appropriate wireless transmitters and receivers known in the art.

With respect to its power supply, in some embodiments the syringe pump may be battery operated, while in other embodiments the syringe pump may include a power cord to connect to a power source.

Figure 35:
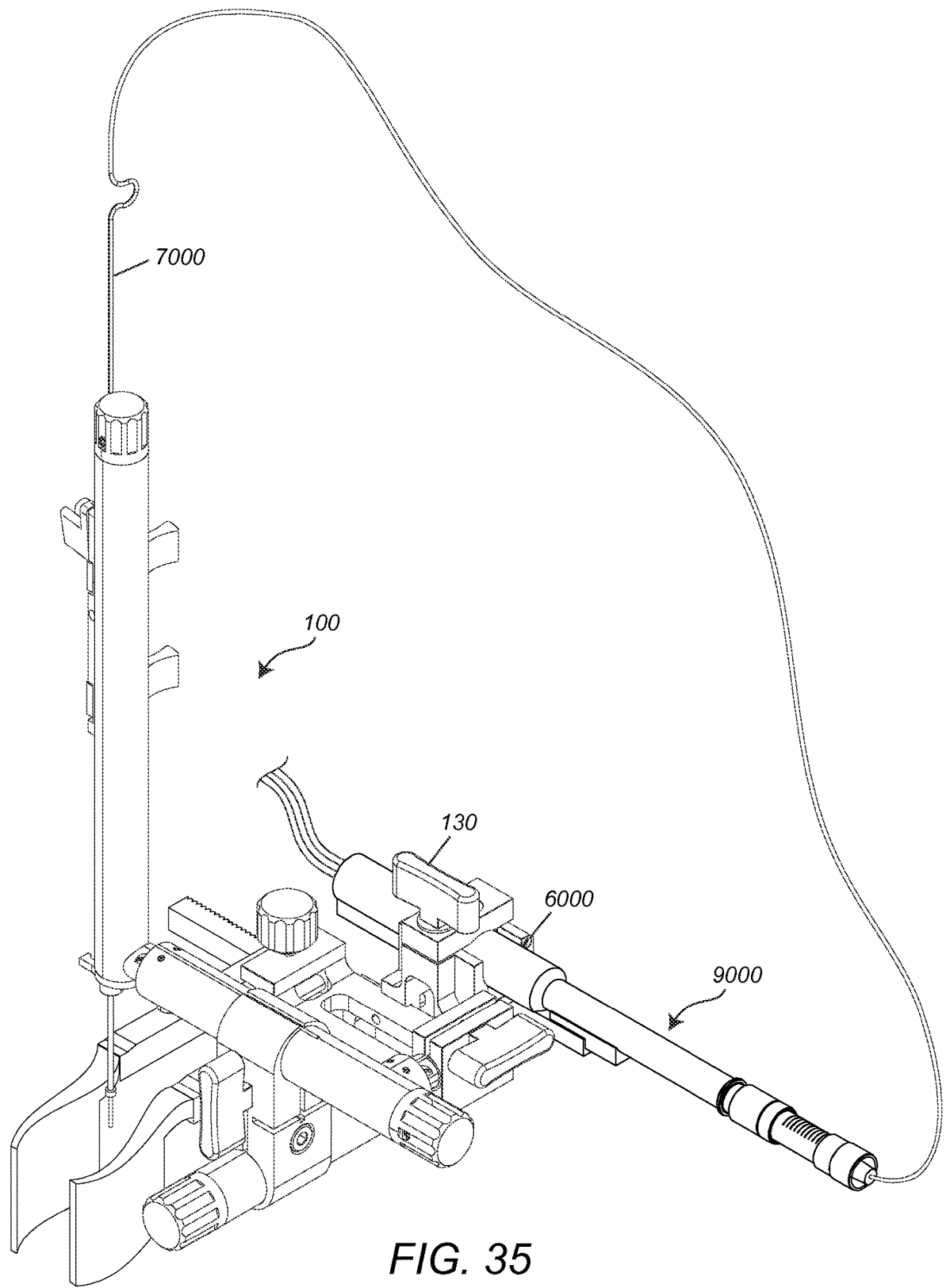
FIG. 35 depicts, in accordance with an embodiment of the invention, syringe pump 9000 engaged in side clamp 6000 of stereotactic device 100.

With respect to its shape, in certain embodiments the syringe pump may be substantially cylindrical, such that it may be held in a side clamp of a stereotactic device (as described herein and shown in FIG. 35) and/or easily held by a user. In other embodiments, the syringe pump may be configured to be a different shape, which is useful for a particular application/procedure.

In certain embodiments, the syringe pump system may also include a connector/coupler component. In some embodiments, the connector/coupler contains threading on one end to allow for its attachment to the housing that contains the motor of the syringe pump. For example connector 503 in FIG. 31 has threading that mates with grooves on the inside of housing 504. Although threading can be used to attach the connector/coupler to the housing of the syringe pump, the connector/coupler may also be attached by any mechanism for attachment described herein that is suitable for that purpose. In some embodiments, the connector/coupler is configured (with threading or otherwise) to attach to a syringe pump motor housing with its first end, and a carpule with its second end, thereby facilitating the connection between the syringe pump motor and drive shaft and the carpule and plunger components. A non-limiting example of a useful configuration is shown in FIG. 31.

In certain embodiments, the syringe pump system may also include a blockage detection device that monitors variations in flow pressure in the interior of the carpule component (e.g through a flow sensor). In some embodiments, the flow rate may be controlled by the speed of the motor and the force exerted (directly or indirectly) onto the plunger.

In various embodiments, the syringe pump system further includes a delivery tube connecting the carpule to a cannula. In certain embodiments, the syringe pump system further includes a cannula described herein. In some embodiments, the cannula connected by the delivery tube to the syringe pump is a floating cannula described herein. In some embodiments, the delivery tube is made of a substance that may include, but is in no way limited to, PTFE Teflon, Tygon, silicone, PVC, FEP, PVDF, rubber, polyethylene and combinations thereof. In some embodiments, the delivery tube is made of polyethylene.

Figure 37:
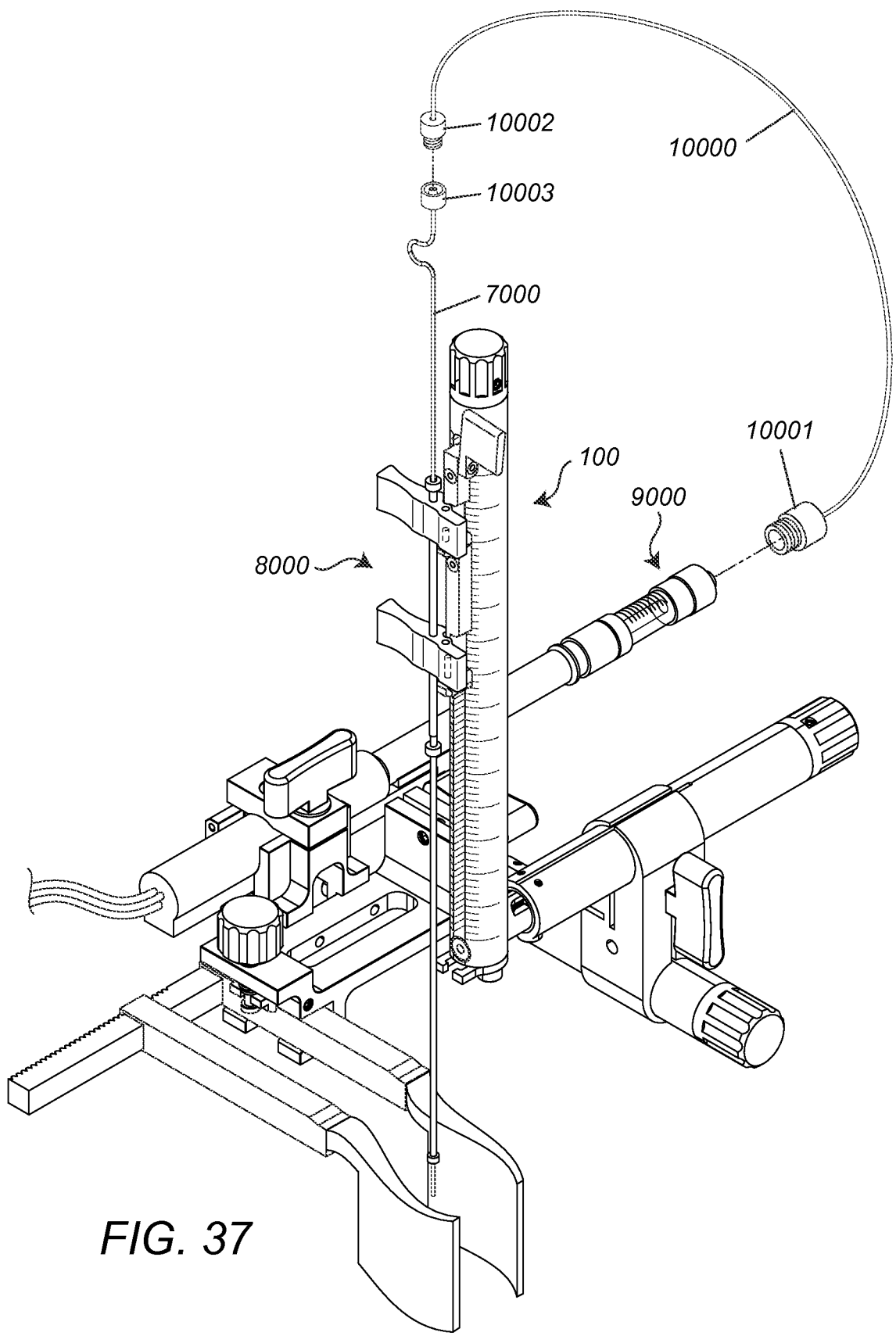
FIG. 37 depicts, in accordance with an embodiment of the invention, syringe pump 9000 can be connected to floating cannula 8000 through tube 10000. Tube 10000 terminates in coupler/connector 10001 on one end, which couples tube 10000 to syringe pump 9000. On the other end, tube 10000 is connected to delivery tube 7000 through male Luer lock fitting 10002 and female Luer lock fitting 10003. The floating cannula 8000 is shown connected to the guiding arm of stereotactic device 100.

In some embodiments, the syringe pump system includes a flexible and sealable carpule delivery tube. This component may be used in conjunction with the carpule component described above, and can be configured in the manner of the flexible and sealable delivery tube 10000 shown in FIG. 37. In some embodiments, the flexible and sealable carpule delivery tube may attach to the carpule through a coupling component situated on its first end. This attachment may be accomplished, for example, through a threaded coupling component 10001, as shown in FIG. 37. One of skill in the art would readily appreciate that any useful coupling component could be substituted for the threaded coupling component 10001 shown in FIG. 37. The carpule delivery tube may also be configured to simultaneously attach to a cannula system described herein. Merely by way of example, this can be accomplished by incorporating complimentary Luer lock fittings, such as those shown as elements 10002 and 10003 in FIG. 37. In some embodiments, the carpule delivery tube may include a valve at one or both ends that serves to allow fluid to flow only in the direction of the cannula, and not towards the carpule. In some embodiments, the carpule of the syringe pump system may be pre-loaded with a sterile saline solution (or any other physiologically tolerable inert solution), and the carpule delivery tube may be pre-loaded with a solution that includes a theraperuitc. In some embodiments, the therapeutic includes cells (including any type of cell described herein). Thus, when the syringe pump is activated, the plunger of the syringe pump pushes the saline solution through the end of the carpule, which in turn advances the therapeutic (e.g. cells) through the carpule delivery tube, then through the cannula system, and finally both the therapeutic (e.g. cells) and saline flow through a hollow needle at the tip of the cannula and into a target site in a patient into whom the needle has been introduced. In some embodiments, the carpule delivery tube may prevent settling, clogging, or clumping of the therapeutic agent being expelled therefrom (e.g. cells).

In some embodiments, the carpule itself is pre-loaded with a therapeutic fluid substance (e.g. cells), and the therapeutic fluid substance is pumped from the carpule, through a delivery tube, then through a cannula, and finally into a target site in a subject. The delivery tube used for these embodiments can be any delivery tube described herein, and the cannula can likewise be any cannula described herein.

Automation of Systems and Apparatuses

Various components of the stereotactic devices, cannula devices, and syringe pump devices may be fitted with sensors and/or motors and/or receivers and/or transmitters in order to "automate" the components and to facilitate the procedures described herein.

Stereotactic Device Automation

Figure 38:
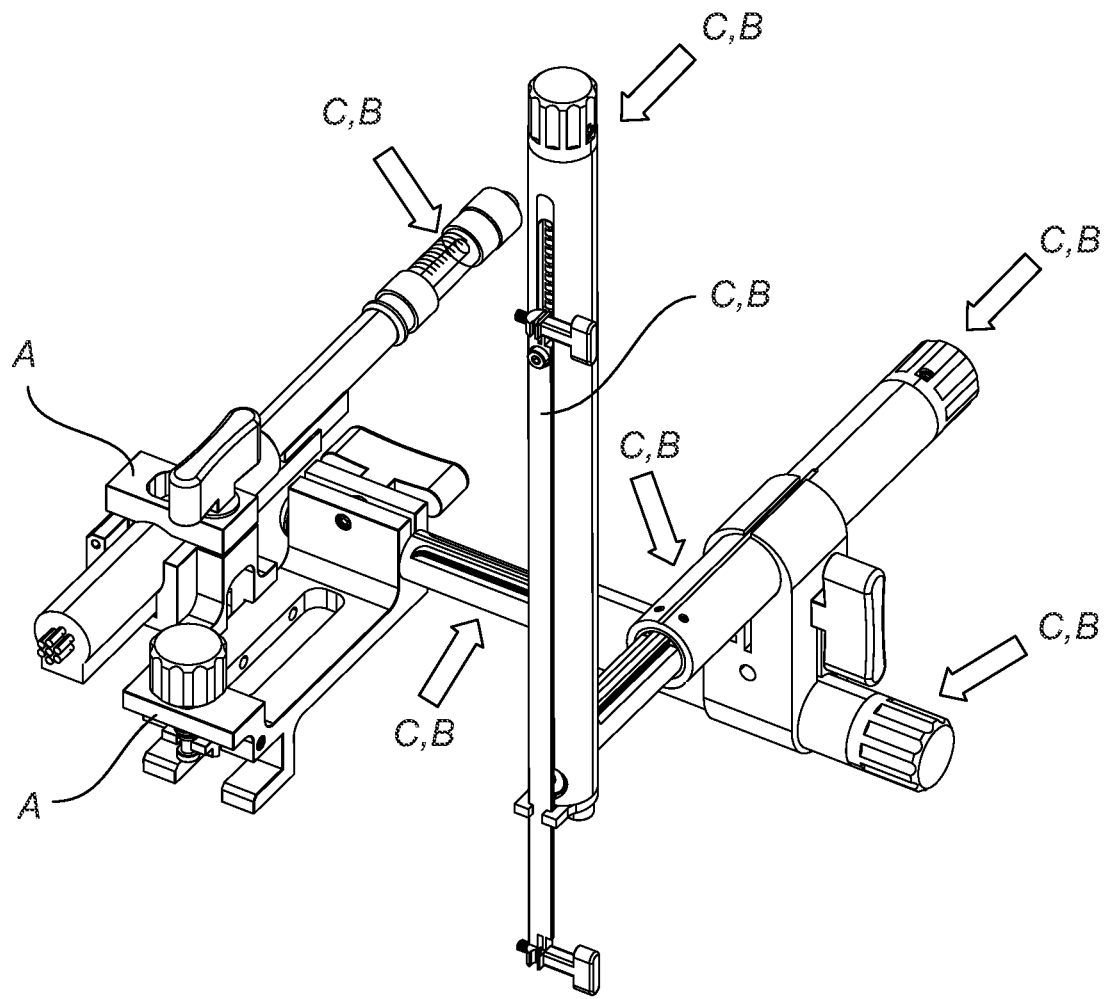
FIG. 38 depicts, in accordance with an embodiment of the invention, arrows and lines indicate locations at which various components or categories of components (labeled "A", "B", and "C") can be positioned on a stereotactic device and a syringe pump attached thereto. "A" indicates one or more components such as an electromechanical switch, an optical sensor, an electromagnetic sensor, and a capacitive sensor, as described in greater detail herein. "B" indicates one or more components such as a strain gauge-based sensor, piezo-based sensor, electromagnetic sensor, optical sensor, capacitive sensor, and potentiometric sensor. "C" indicates one or more components such as a video-based motion capture system, a potentiometer (linear distance sensor), a linear variable differential transformer (LVDT), an inductive proximity sensor, a rotary encoder, an incremental encoder, an absolute position encoder, a Gill sensor, and an ultrasonic sensor.

Sensors may be placed at a number of locations on the stereotactic devices described herein, including but in no way limited to the locations indicated by arrows and wavy lines in FIG. 38. The sensors may allow for determining the positions of each of the arms of the stereotactic device, relative to one another and/or relative to one or more landmark on a patient and/or relative to an instrument attached to the stereotactic device. The sensors used for this aspect of the invention may be motion sensors, heat sensors, infrared sensors, and the like. Further, any component or category of component listed in the figure description for FIG. 38 may be included as indicated by the arrows and wavy lines. When motion sensors are positioned on the device, they may be positioned to provide feedback to a central control unit, which is configured for controlling one or more component of the device, so that the relative position of each arm can be determined and properly adjusted during a procedure. One or more heat sensors may be positioned on the device such that proximity to tissue can be determined. Thus, merely by way of non-limiting example, one or more heat sensors may be positioned near the tip of the guiding arm.

The stereotactic device may alternatively or additionally include motors configured to adjust the position of one or more arms of the device described herein (e.g. guiding arm, positioning arm, etc.). In certain preferred embodiments, one or more arms of the device may be configured with a motor. In some embodiments, the motor may be housed within or partially within the dial. In some embodiments, the motor is operably connected to the dial through a drive shaft, or an alternative connection. In some embodiments, the motor is configured to cause the dial of one or more of the stereotactic arms (e.g. as depicted in the examples) to rotate, thereby causing the arm with which it is associated to advance or retract in a telescoping fashion, depending upon the direction of rotation. In some embodiments, the motors are brushless DC motors. In some embodiments, the motors and any associated cabling are completely contained within the arms of the stereotactic device, and may be held in an appropriate position by channels, clips, conduits or other mechanisms known in the art. In some embodiments, the stereotactic device is configured such that it can be autoclaved. In some embodiments, the motors of the stereotactic device will be powered by batteries completely contained within the device. The batteries associated with the device can be any of a number of types which would be readily appreciated by one of ordinary skill in the art. Merely by way of non-limiting example, the batteries may be lithium polymer, ribbon batteries, silver oxide, lithium, zinc-air, combinations thereof or the like.

In some embodiments, one or more motors of the stereotactic device is configured to communicate with a wireless receiver capable of receiving wireless input from a computing device (e.g. a handheld computer, desktop computer, handheld computing device, or the like). Any sensors located on the stereotactic device (as described herein) may be configured to send and/or receive wireless signals (directly or indirectly) to a computing device (e.g as described above) in order to communicate information about relative position, motion, or other data they capture. Any camera located on or associated with the device (as described herein) may also be configured to communicate with a computing device wirelessly, such that it can transmit information (images, etc.) or receive information (e.g. instructions to zoom in, focus, change modes etc.). Non-limiting examples of wireless transmitters and receivers that can be used in accordance with the description above include WiFi, RF, Bluetooth, and the like.

Cannula Device Automation

Figure 39:
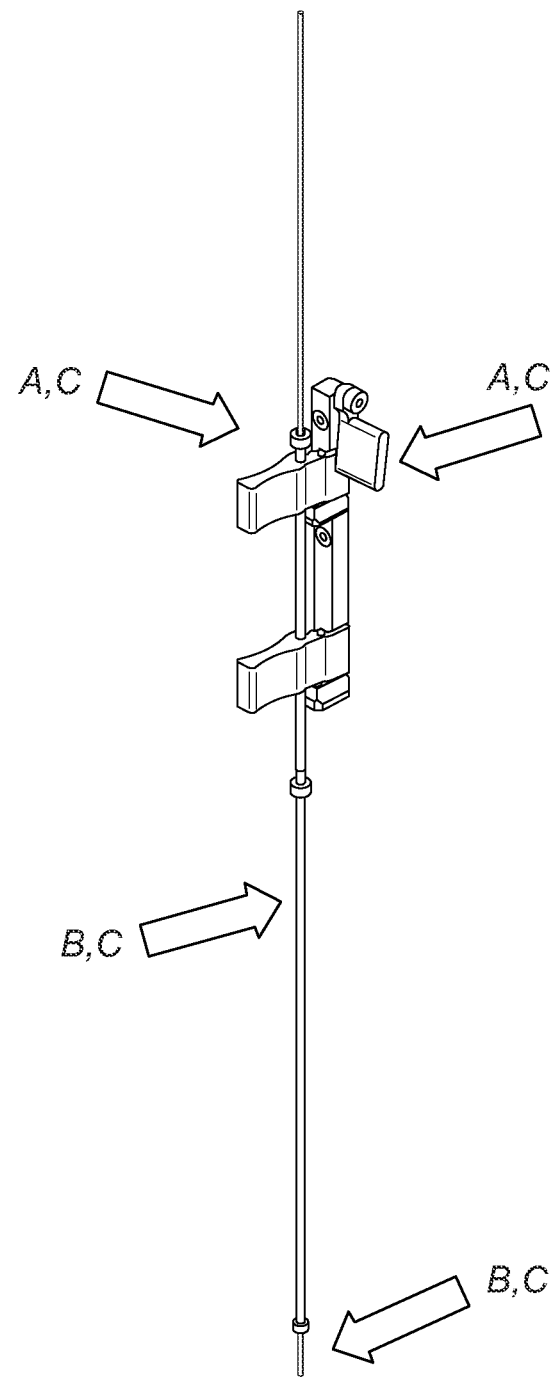
FIG. 39 depicts, in accordance with an embodiment of the invention, arrows and lines indicate locations at which various components or categories of components (labeled "A", "B", and "C") can be positioned on a floating cannula system. "A" indicates one or more components such as an electromechanical switch, an optical sensor, an electromagnetic sensor, and a capacitive sensor, as described in greater detail herein. "B" indicates one or more components such as a strain gauge-based sensor, piezo-based sensor, electromagnetic sensor, optical sensor, capacitive sensor, and potentiometric sensor. "C" indicates one or more components such as a video-based motion capture system, a potentiometer (linear distance sensor), a linear variable differential transformer (LVDT), an inductive proximity sensor, a rotary encoder, an incremental encoder, an absolute position encoder, a Gill sensor, and an ultrasonic sensor.

In certain embodiments, the cannulas and cannula systems described herein are fitted with one or more sensors that allow for tracking motion of the cannulas or portions thereof. The motion sensors can be configured to track relative motion between cannula parts (e.g. the floating and base cannulas of the cannula system) and/or between one or more cannula parts and the stereotactic device, and to track the depth of injection of the cannula needle when inserted into an anatomical target (e.g. the spinal cord). Non-limiting examples of motion sensors that can be used in this context include a video based motion capture system, potentiometer (linear distance sensor), a linear variable differential transformer (LVDT), an inductive proximity sensor, a rotary encoder, an incremental encoder, an absolute position encoder, a Gill sensor, and an ultrasonic sensor. Each of these types of components could be useful in any of numerous positions on the device, including but not limited to the positions labeled "C" in FIG. 39.

In some embodiments, a pressure sensor is used in conjunction with the cannula needle, in order to measure resistance encountered by the needle (e.g. spinal cord or other tissue during injection). Non-limiting examples of sensors that could be configured on or associated with the device include strain gauge based, piezo bases, electromagnetic, optical, capacitive, potentiometric, or combinations thereof. Each of these types of sensors could be useful in any of numerous positions on the device, including but not limited to the positions labeled "B" in FIG. 39. The attachment component of the cannula system may further be fitted with a sensor to detect proper closure around the connecting tabs as described herein. Non-limiting examples of sensors that could be used in this setting include one or more electromechanical switch, one or more optical sensor, one or more electromagnetic sensor, and one or more capacitive sensor. In some embodiments, the cannula can be fitted with one or more sensors in the positions labeled "A" in FIG. 39.

In some embodiments, the cannula may be fitted with a sensor on or near the tissue stopper in order to sense the depth of injection (e.g. optically, for an optical sensor, or by pressure with a pressure sensor as described above).

Syringe Pump Device Automation

In some embodiments, the syringe pump is configured with one or more sensors to allow for tracking fluid flow (e.g. rate, duration, clogging) of a therapeutic or other medically useful substance (e.g. cells) within the syringe pump. In some embodiments, a flow meter is configured to interact with one or more components of the syringe pump. The flow meter can be used to regulate and track the flow of fluid into a patient (e.g. during an injection). In some embodiments, the flow meter is positioned between the syringe pump and cannula. In some embodiments, the flow meter is positioned between the syringe pump and delivery tube. In some embodiments, one or more portion of the flow meter is positioned within the cannula. In some embodiments, one or more portion of the flow meter is configured within the syringe pump. In some embodiments, a syringe pump described herein is configured with a receiver and or transmitter connected to its motor that allows the motor to wirelessly communicate with a computing device (as described above) configured to control it. In this way, the syringe pump may be controlled (e.g. speed and duration of pumping) by a computing device in response to user input (or automatically) throughout the course of a medical procedure described herein.

Coordination of Devices

In some embodiments, two or more of the stereotactic device, syringe pump, cannula, or imaging components described herein are controlled and coordinated by a single computing system (as described above). In other embodiments, each device (and the components connected thereto as described herein) is controlled by a separate computing system (as described above).

Non-limiting examples of device coordination and automated function in the context of medical procedures are provided herein below.

Automation of the stereotactic device can include automation relating to placement of a cannula needle described herein for delivery of therapeutic agents into a subject by means of a preloaded syringe pump of any configuration described herein. Placement of the cannula needle depends on localization of vasculature on the surface of the spinal cord. Currently, a physician places the cannula into the spinal cord by choosing stereotactic coordinates that will prevent the cannula from being inserted into the spinal cord vasculature. Automation of the stereotactic device can include the use of various imaging techniques, imaging software and sensors placed on the device to determine localization of the cannula within the spinal cord and assist the physician in the positioning of the cannula. In some embodiments, automation includes the use of preoperative imaging and/or intraoperative imaging combined with visual, optical, spatial recognition and/or surface tracing software (including any appropriate software known in the art). Further, the stereotactic device can be configured to have a plurality of sensors placed at various locations on the device (e.g. at the locations shown by arrows in FIG. 38), in order to ensure the accuracy of the placement of the cannula. Types of sensors that may be incorporated into the device include optical, digital, and heat sensors that can be used for localization. Non-limiting examples of sensors/components that can be used in conjunction with the devices described herein include: a potentiometer (linear distance sensor), a linear variable differential transformer (LVDT), an inductive proximity sensor, a rotary encoder, an incremental encoder, an absolute position encoder, a Gill sensor, and an ultrasonic sensor.

In some embodiments, the stereotactic device coordinates may be based on and/or determined by preoperative imaging (e.g. MRI and/or CT, and/or ultrasound, and the like) and/or intraoperative imaging (e.g. MRI and/or CT, and/or ultrasound, and the like). For example, a user may input or select coordinates and/or a region of interest on a computing device (configured in any manner indicated above) to determine the number and/or placement and/or timing of the injections. In one example, the coordinates may be based on landmarks determined from a pre-operative image such as an MRI and/or intraoperative imaging. In some embodiments, sensors and/or cameras communicate with a computer that is used to register and optionally re-register relative coordinates of the device and/or vasculature (determined by IR or visible range imaging). In some embodiments, the coordinates are registered continuously in order to account for any patient motion before or during the injection process. In some embodiments, one or more camera is mounted on or near the device during the automated injection process (as described herein), so that the surgeon can visualize the target, but still benefit from the steadiness of an automated injection. In some embodiments, the stereotactic device, one or more camera and a computing system are configured to allow a surgeon to visually select and virtually mark an anatomical target (e.g. spinal cord injection site) based on information received from the one or more camera (as described above) and/or additional intraoperative imaging. A computing device could then automatically adjust the position of one or more arms of the stereotactic device (as described above), in order to place an injection at an intended target, regardless of patient motion. Based on the coordinates and/or region of interest, the user may select the number of injections need for the procedure and/or the time needed between injections and/or the volume of fluid introduced by each injection.

In some embodiments, the stereotactic device may be associated with a computing system and monitor configured to display a range of possible injection site coordinates based on the surface localization of the spinal cord vasculature or other region of interest. As such, the computer system may prompt a user to select a range of possible coordinates for injection, or give an option to input exact coordinates. In some embodiments, the user may manually input the coordinates. In some embodiments, once the coordinates have been selected (manually or automatically) a physician may be required to confirm the coordinates before the procedure continues. In some embodiments, once the coordinates are confirmed, they are recorded into a surgical procedure record, (electronic medical record (EMR)). In some embodiments, the stereotactic device (and cannula and needle attached thereto) will be automatically positioned to the location of interest based on the confirmed coordinates. Once the arms of the stereotactic device are located in the correct position, the cannula needle may be positioned/inserted to an appropriate depth in the spinal cord (or other anatomical location in other embodiments), as determined by a pre-operative MRI or intraoperative imaging (as described herein). The depth of needle position may be limited by a fixed or adjustable tissue stopper, as described herein. The cannula may also include a sensor (e.g. resistance, optical, and/or digital sensor), as described above. In some embodiments, the sensor may be located on the flange of the needle hub (i.e. tissue stopper), in order to locate the dorsal surface of the spinal cord. In some embodiments, the cannula is configured such that the sensor will provide pressure feedback to the system and ensure the cannula needle is positioned at the predetermined depth. Once the cannula is positioned at the predetermined depth, the depth of the cannula will be recorded into a surgical procedure record, EMR, and/or patient health record. In some embodiments, a user will confirm the finalized position of the cannula in order for the procedure to continue (e.g. injection of a therapeutic agent described herein). In some embodiments, one or more sensor positioned on the cannula may be used to sense "bucking" motion of a patient during the surgical procedure. In some embodiments, the device is configured such that when significant patient motion is detected, the injection is stopped and/or the cannula is retracted out of the surgical space to prevent damage and/or injury to the patient.

In some embodiments, a syringe pump attached to the stereotactic device is utilized to inject a therapeutic agent and/or other agents (e.g. pain medication, contrast agents, etc.) via the cannula needle to the spinal cord (as described herein). Accordingly, confirmation of the position of the cannula may result in an associated computing system (as described herein) sending a signal to an associated syringe pump to deliver a therapeutic and/or other agent through the cannula needle. In some embodiments, the syringe pump may be a syringe pump described herein. In some embodiments, the syringe pump includes one or more sensors (e.g. pressure sensor) configured to detect flow, volume and rate of the fluid being delivered/injected (as described above). In addition, or in alternative embodiments, a sensor in the syringe pump and/or syringe pump carpule is configured to detect the volume of a therapeutic agent or other substance contained therein. In some embodiments, once the syringe pump has dispensed the entire volume of the therapeutic agent intended to be injected, the pump will stop and/or turn off. In one example, a series of injections may be required for the surgical procedure (e.g. 2-10 or more injections). As such, the pump may stop dispensing therapeutic agent once the contents of the pump have expelled a predetermined amount of therapeutic agent (e.g. 100 microliters).

In some embodiments, a cannula may receive a signal directly from a syringe pump (through a wire or wirelessly) once the syringe pump has finished expelling a therapeutic agent. In some embodiments, the cannula will retract from the spinal cord once a predetermined amount of the therapeutic agent has been injected. The cannula may retract to a predetermined height, such that when moved, the cannula may not cause injury to a patient. The cannula may be retracted by appropriate positioning of an arm of the stereotactic device (manually or automatically) and/or by appropriate retraction of the cannula itself (manually or automatically). For example, the cannula may be retracted to a specific height in order to prepare to perform another injection, if the procedure calls for a series of injections. In another example, the cannula may be retracted to a height significantly above the surgical space if the procedure has been completed.

In various embodiments, the invention teaches a kit which comprises, consists of, or consists essentially of one or more systems or devices disclosed or referenced herein, or combinations thereof. In some embodiments, the kit may include, but is in no way limited to, one or more stereotactic device or system and/or cannula device and/or system and/or syringe pump device and/or system and/or carpule and/or delivery tube and/or therapeutic agent (including but not limited to any therapeutic agent or combination of therapeutic agents described herein) and/or therapeutic stem cells (including any type of or particular stem cells described herein). In some embodiments, the kit includes a combination of two or more items described above.

In some embodiments, the components of the kit are configured to facilitate the treatment of a neural degenerative disease or neurologic injury, as described herein. In some embodiments, the components of the kit are configured to facilitate treatment of ALS, as described herein. In some embodiments, the components of the kit are configured to treat a spinal cord injury.

In one embodiment, the kit is configured particularly for the purpose of treating mammalian subjects. In another embodiment, the kit is configured for the purpose of treating human subjects. In another embodiment, the kit is configured for treating adolescent, child, or infant human subjects. In further embodiments, the kit is configured for veterinary applications, treating subjects such as, but not limited to, farm animals, domestic animals, and laboratory animals.

Instructions for use may be included in any of the kits described herein. "Instructions for use" typically include a tangible expression describing the technique to be employed in using the components of the kit to effect a desired outcome, such as, but in no way limited to, introducing a substance into a target region of a subject's body in any manner described or referenced herein. Optionally, the kit also contains other useful components, such as materials used for surgical preparation appropriate for the particular procedure for which the kit is intended to be used.

The materials or components assembled in the kit are typically contained in suitable packaging material(s). As employed herein, the phrase "packaging material" refers to one or more physical structures used to house the contents of the kit, which can include one or more of the devices, systems, therapeutics, or combinations thereof described herein, depending upon the particular desired application. The packaging material is constructed by well-known methods, preferably to provide a sterile, contaminant-free environment. As used herein, the term "package" can refer to plastic, paper, foil, and the like, or similar materials capable of holding the individual kit components. With regard to the therapeutic material, any type of suitable container (e.g. glass, plastic, composite, or the like) typically used to house the therapeutic material may be used as packaging within the kit. The packaging material generally has an external label which indicates the contents and/or purpose of the kit and/or its components.

EXAMPLES

Example 1

Stereotactic Apparatus with Side Clamp

Figure 10:
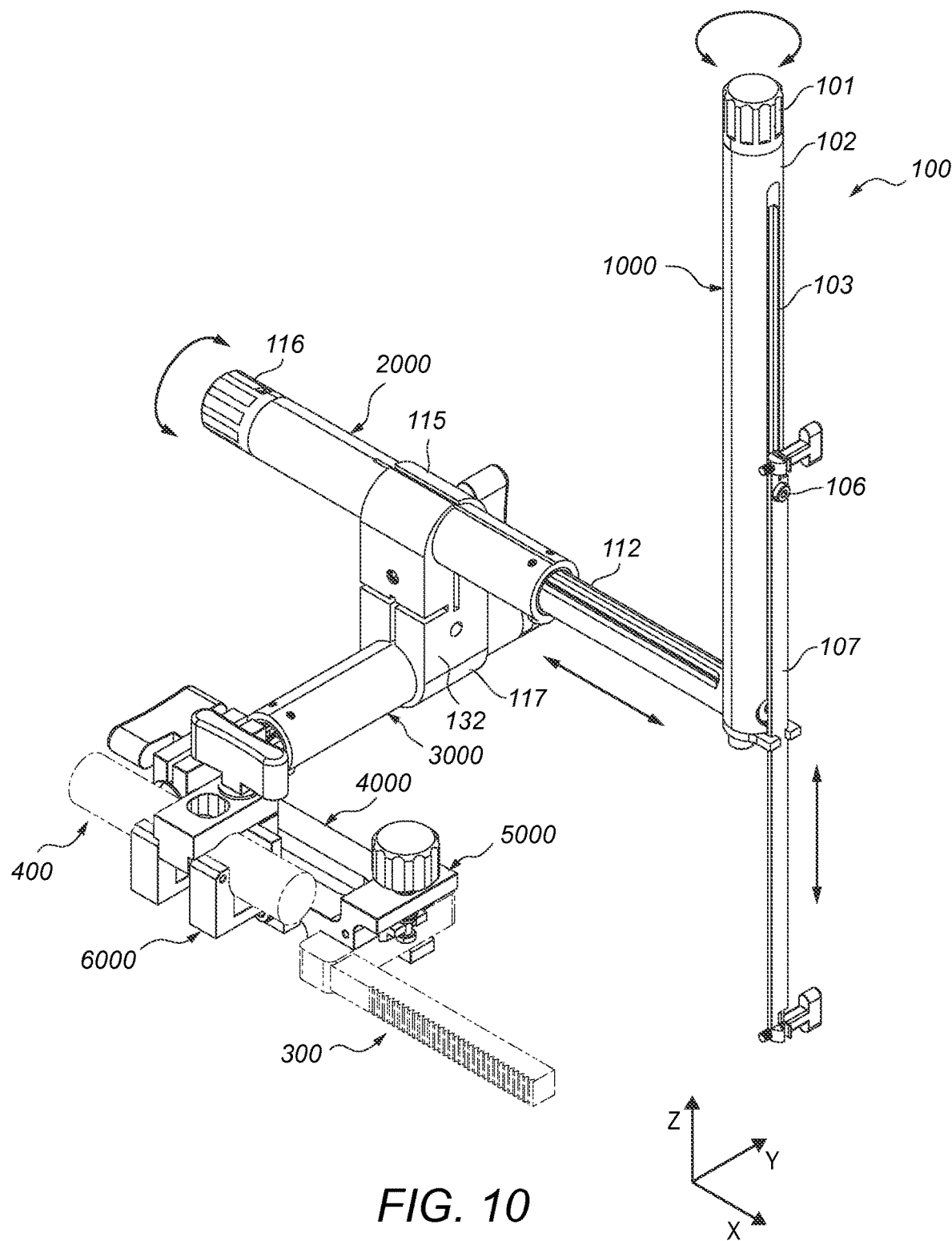
FIG. 10 depicts, in accordance with an embodiment of the invention, rotating dial 116 causes telescoping of inner nesting element 112 of positioning arm 2000.

FIG. 1A depicts exemplary stereotactic apparatus 100. Stereotactic apparatus 100 includes guiding arm 1000, which includes an elongated channel 103 situated along its long axis (FIG. 1A). Guiding arm 1000 includes a dial 101 and an elongated cylindrical body 102 (FIG. 1A). Guiding arm 1000 also includes instrument attachment component 107, and clamps 105 and 110 which are tightened and loosened by screws 104 and 109, respectively (FIG. 1A). The guiding arm 1000 further includes instrument attachment component guide 108. FIG. 18 depicts an exploded view of guiding arm 1000, in which the assembly of threaded shaft 148, bushing 147, curved spring washer 146, radial ring 145, set screw 144, and dial 101 is shown. FIG. 18 also depicts the assembly of screws 153a and 153b, instrument attachment component guide 108 (with screw receiving holes 152a and 152b), cylindrical receiving stopper 151, and screw 133. FIG. 18 shows instrument attachment component 107 is attached to sliding carriage 149 through hole 150. FIGS. 10 and 18 show that as dial 101 is turned, intermediate components 145-148 (shown in FIG. 18) cause carriage component 149 to glide along elongated channel 103 (along the z-axis), together with instrument attachment component 107. It follows that any instrument attached to instrument attachment component 107 would also travel along the z-axis when the position of instrument attachment component 107 is adjusted by rotating dial 101.

Figures 17A, 17B:
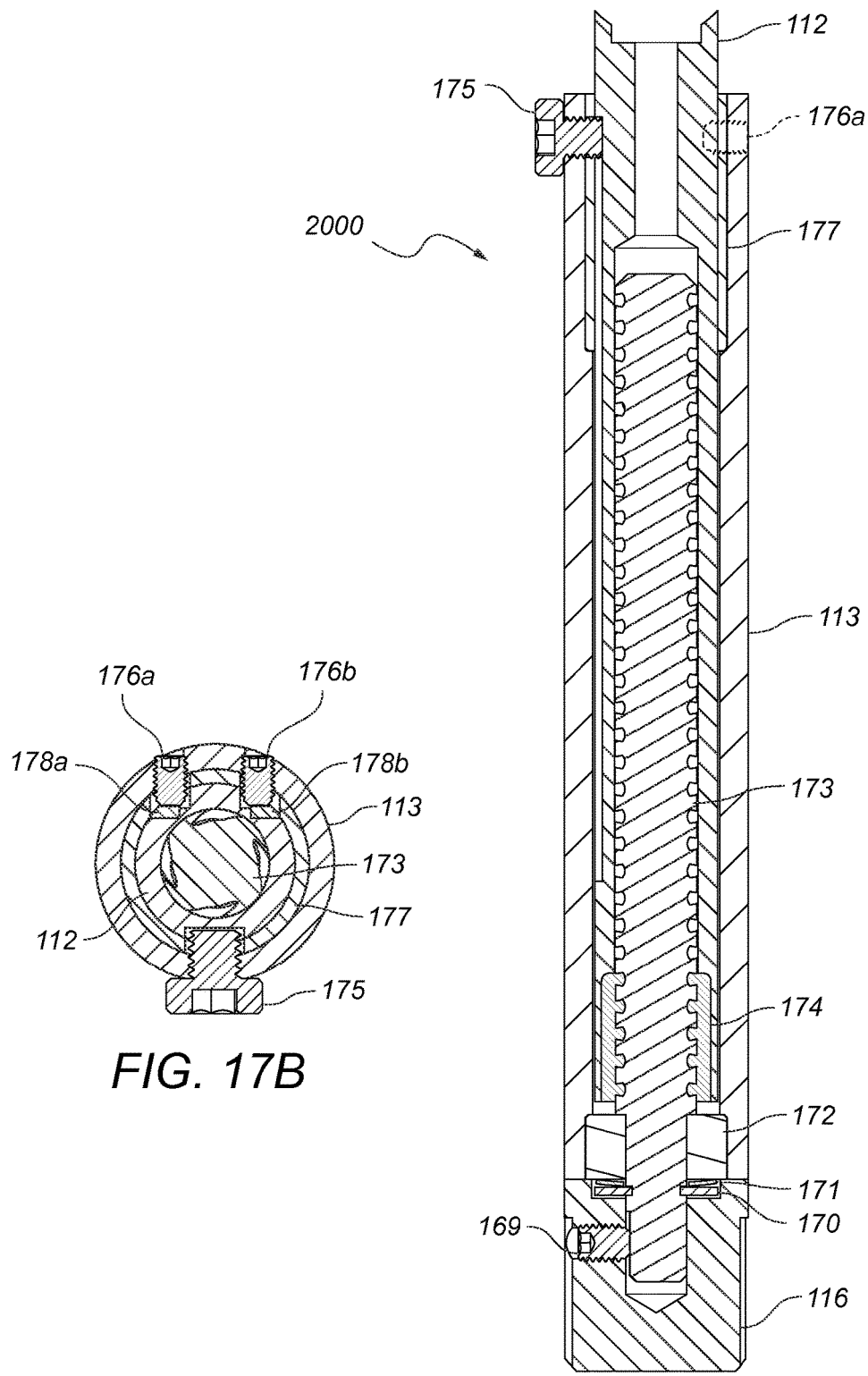
FIG. 17A depicts, in accordance with an embodiment of the invention, a cross-sectional view of the long axis of positioning arm 2000.
FIG. 17B depicts, in accordance with an embodiment of the invention, a cross sectional view of the short axis of positioning arm 2000.

FIG. 3 shows an exploded view of stereotactic apparatus 100, in which the attachment of guiding arm 1000 to positioning arm 2000 is shown to be accomplished by securing screw 133 of guiding arm 1000 to receiving socket 134 of positioning arm 2000. FIG. 3 also shows that positioning arm 2000 traverses a cylindrical opening through upper collar 115 of cross clamp 132. FIG. 15 shows a partially exploded view of positioning arm 2000, in which the assembly of collar 174, threaded shaft 173, bushing 172, curved spring washer 171, radial ring 170, set screw 169, and dial 116 is shown. FIG. 15 also shows outer nested component 113 and inner nested component 112 of positioning arm 2000. FIG. 16 shows the assembly of inner 112 and outer 113 nesting components of positioning arm 2000. Specifically, screw 175 and set screws 176a and 176b traverse outer nested component 113 and inner stabilizing collar 177. The set screws 176a and 176b then contact supporting elements 178a and 178b, respectively, which in turn rest on the flat portions of elongated L-shaped grooves 179a and 179b, respectively. This arrangement allows supporting elements 178a and 178b (and screw 175) to constrain motion of inner nesting component 112 of positioning arm 2000, and adds to the stability and control of its telescoping motion. Cross-sectional views of positioning arm 2000 are depicted in FIGS. 17A and B.

Figure 4:
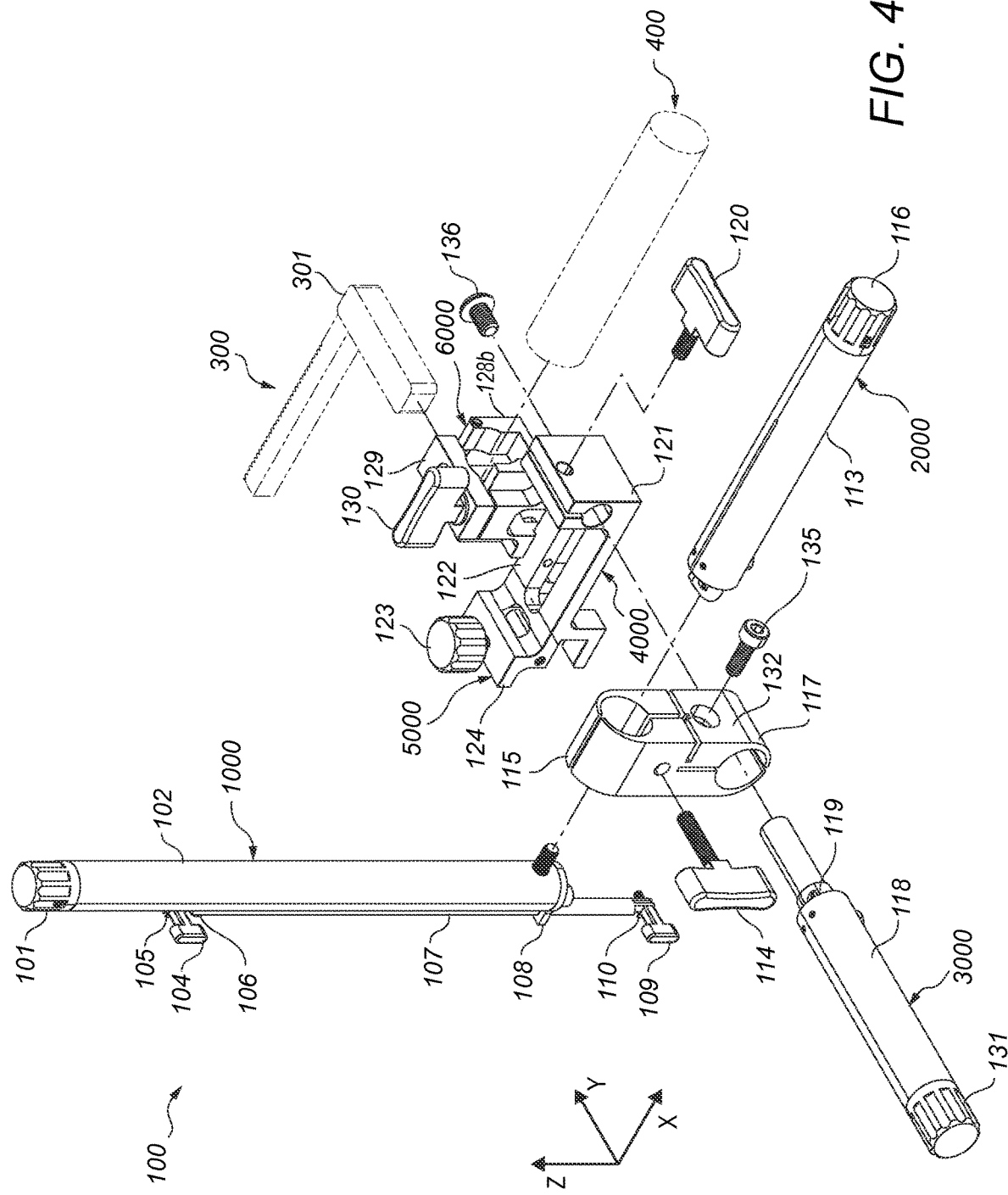
FIG. 4 depicts, in accordance with an embodiment of the invention, a partially exploded view of stereotactic apparatus 100.
Figure 13:
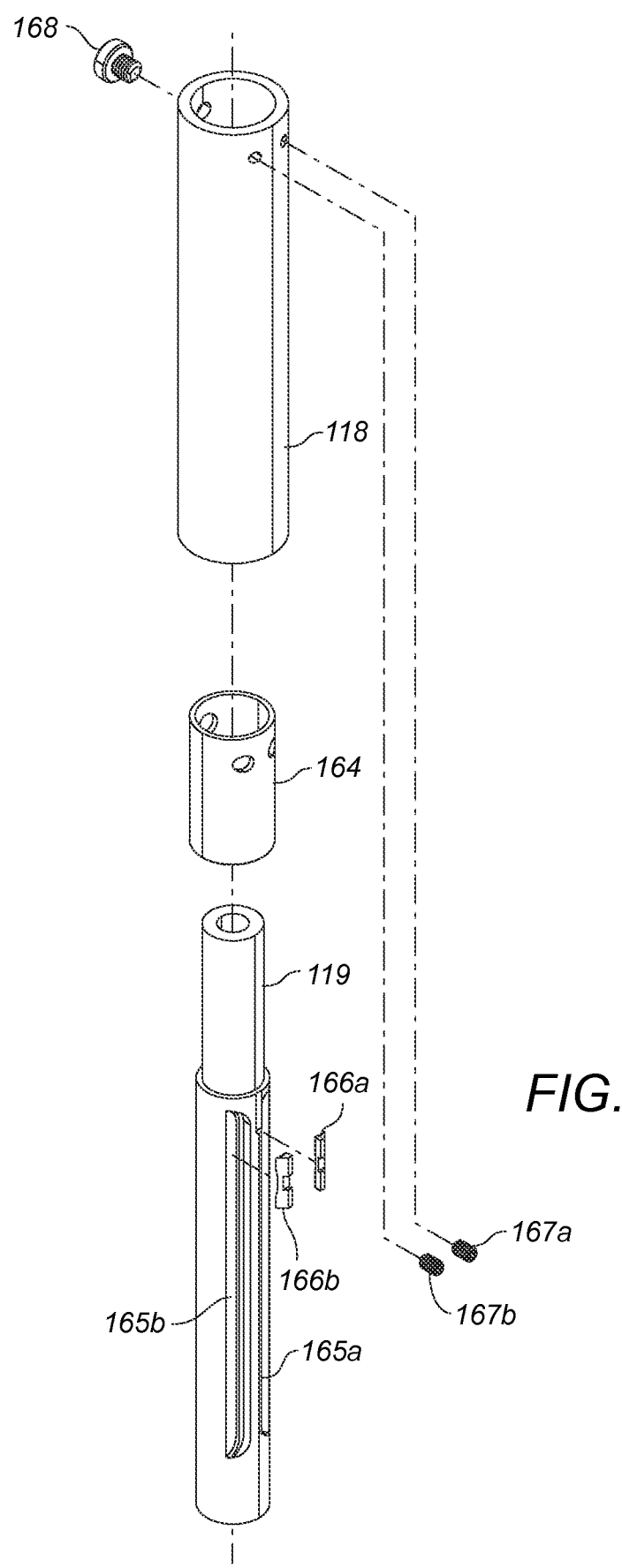
FIG. 13 depicts, in accordance with an embodiment of the invention, an exploded view of a portion of connecting arm 3000.
Figures 14A, 14B:
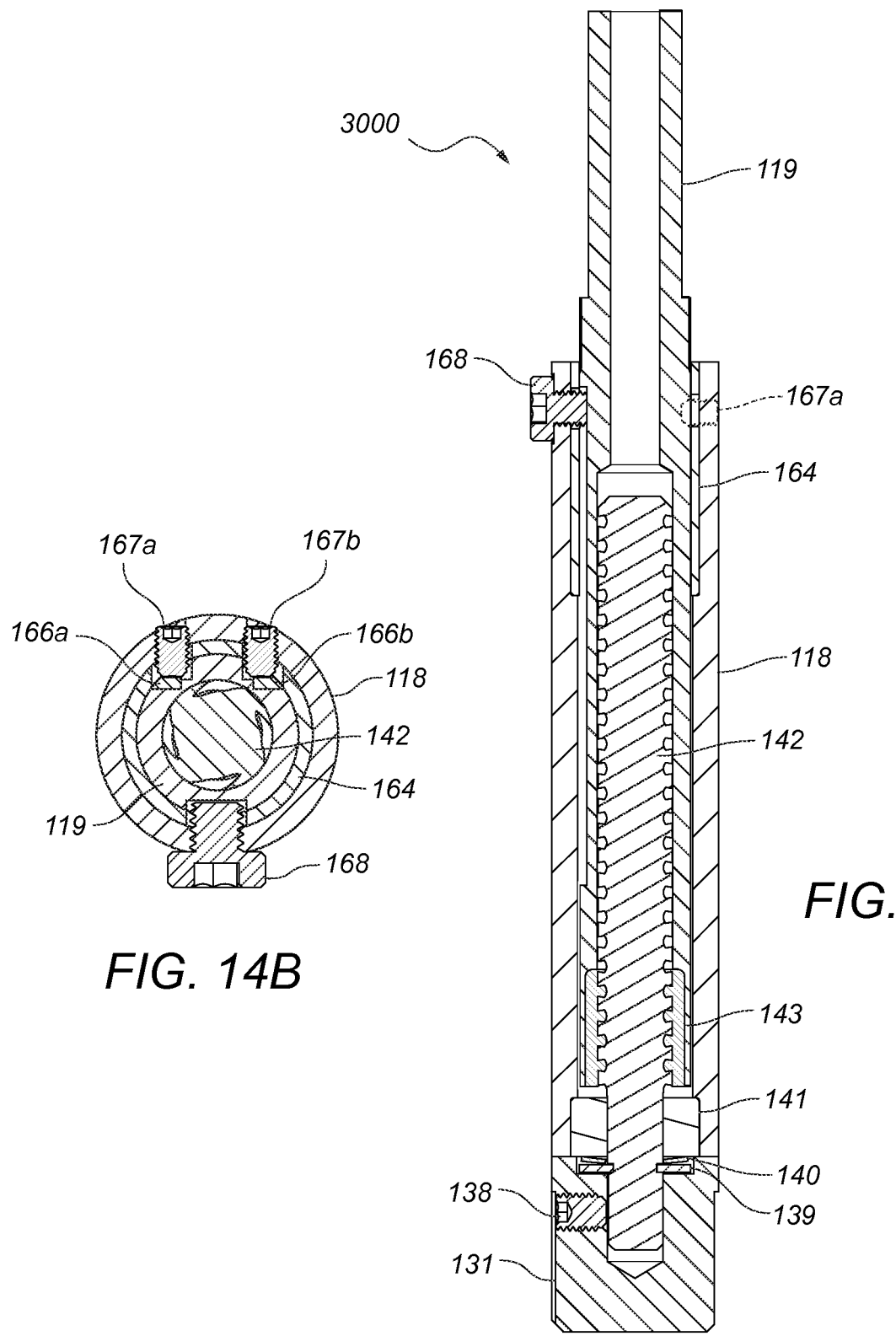
FIG. 14A depicts, in accordance with an embodiment of the invention, a cross-sectional view of the long axis of connecting arm 3000.
FIG. 14B depicts a cross-sectional view of the short axis of connecting arm 3000.

In addition to guiding arm 1000 and positioning arm 2000, FIG. 3 also shows connecting arm 3000 of stereotactic apparatus 100 with outer nested element 118 and inner nested element 119. FIG. 3 shows connecting arm 3000 traverses the cylindrical opening of lower collar 117 of cross clamp 132. FIG. 3 also shows that connecting arm 3000 traverses a cylindrical opening in clamp 121, and is fastened to end screw 136. An alternate view of these components is demonstrated in FIG. 4. FIG. 4 also depicts knob 120 and screw 135, which can each be tightened to secure connecting arm 3000 in clamp 121 and lower collar 117 (of cross clamp 132), respectively. FIG. 13 shows the assembly of inner 119 and outer 118 nesting components of connecting arm 3000. Screw 168 and set screws 167a and 167b traverse outer nested component 118 and inner stabilizing collar 164. Set screws 167a and 167b then contact supporting elements 166a and 166b, respectively, which in turn rest on the flat portion of elongated L-shaped grooves 165a and 165b, respectively. This arrangement allows supporting elements 166a and 166b (and screw 168) to constrain motion of inner nesting element 119, and adds to the stability and control of its telescoping motion. Cross-sectional views of attaching arm 3000 are depicted in FIGS. 14A and B.

FIG. 3 also shows a view of securing arm 4000, which includes clamp 121, body 122, and retractor attaching clamp 5000. Retractor attaching clamp 5000 is formed by knob 123, stabilizing screw 126 (which passes through upper lip 124 of clamp 5000), upper stabilizing arms 125a and 125b, and lower stabilizing arms 127a and 127b. An exploded view of securing arm 4000 is shown in FIG. 21. In this view, incorporation of set screw 162 and rod 161 in the context of the other components of the clamp can be seen.

FIG. 3 further shows side clamp 6000 of stereotactic apparatus 100. Side clamp 6000 includes tray arms 128a and 128b, and hinged top 129. Hinged top 129 includes an opening through which a portion of an object clamped by side clamp 6000 (such as elongated object 400 shown in FIG. 1) can be viewed.

Figure 7:
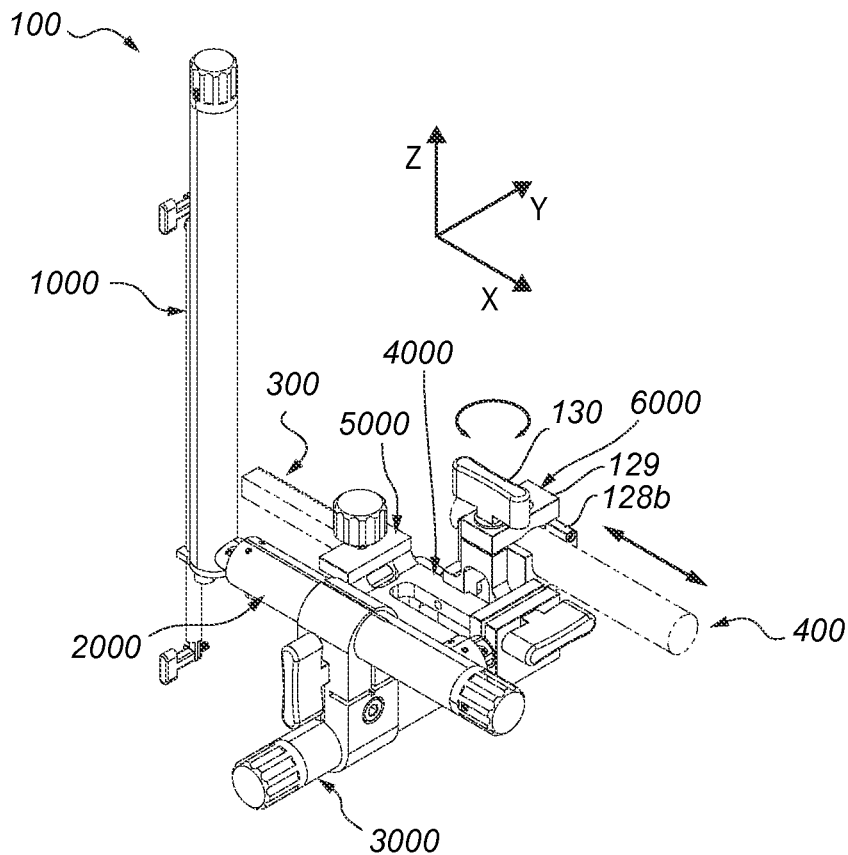
FIG. 7 depicts, in accordance with an embodiment of the invention, loosening knob 130 allows for adjustment of the position of cylindrical object 400 along the x-axis.
Figure 11:
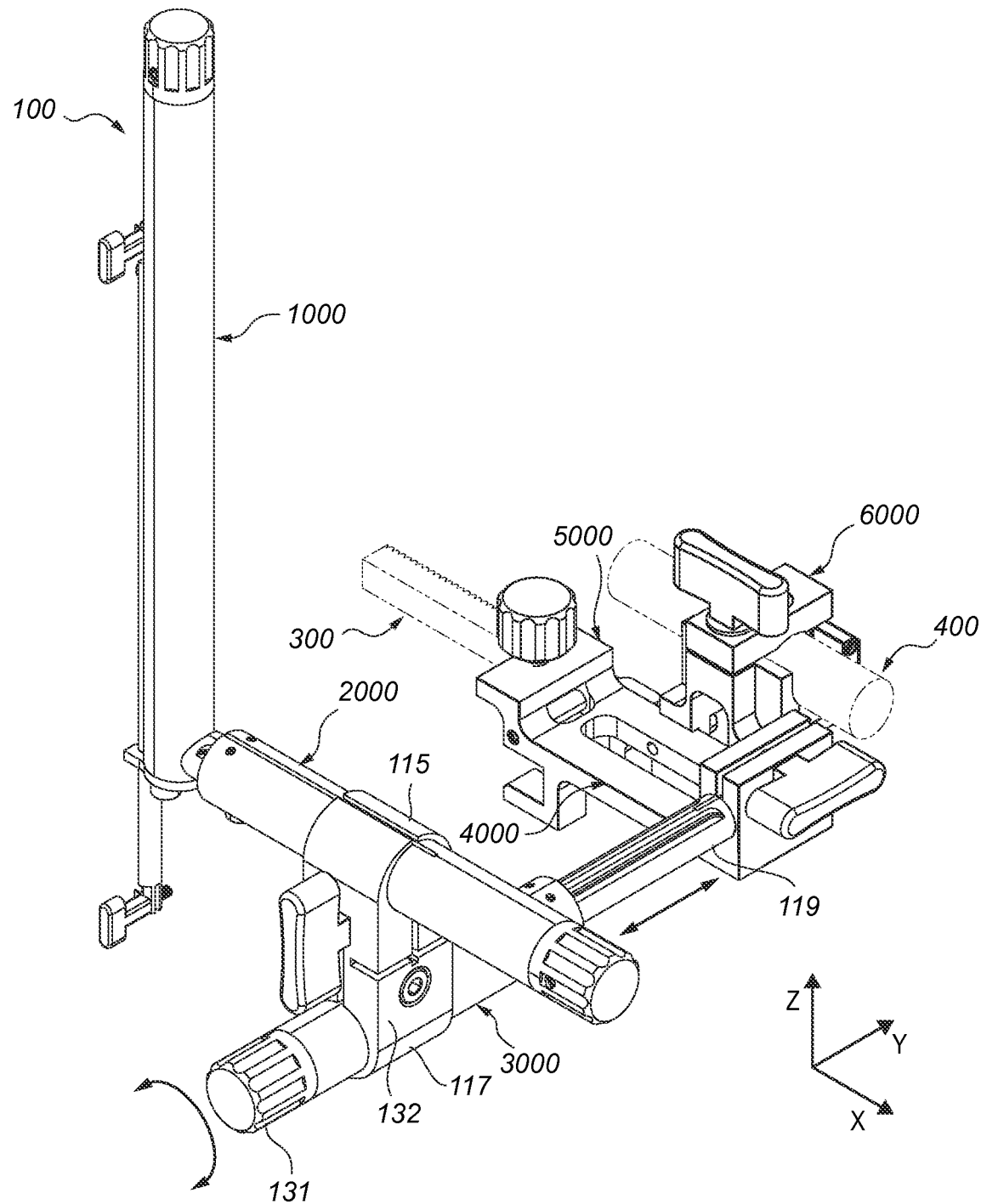
FIG. 11 depicts, in accordance with an embodiment of the invention, rotating dial 131 causes telescoping motion of inner nesting element 119 of connecting arm 3000.

Turning now to the various possible adjustments and orientations of the arms (and components thereof) of stereotactic apparatus 100 shown in FIGS. 5-11. FIG. 5 shows rotation of knob 114 loosens upper collar 115 of cross clamp 132, thereby allowing adjustment of the position of positioning arm 2000 along the x-axis. FIG. 8 shows that rotation of knob 114 (and associated loosing of upper collar 115 of cross clamp 132) allows for rotation of positioning arm 2000 along the x-axis, which translates into motion of guiding arm 1000 along the y-z plane. FIG. 6 shows that rotation of screw 135 results in loosening lower collar 117 of cross clamp 132, which allows for adjustment of the position of positioning arm 2000 along the y-axis. FIG. 9 shows that rotation of screw 135 (and associated loosening of lower collar 117 of cross clamp 132) allows for rotation of cross clamp 132 along the y-axis, which translates into motion of guiding arm 1000 along the x-z plane. FIG. 7 demonstrates that rotation of knob 130 (and associated loosening of side clamp component 129) allows for adjustment of the position of cylindrical object 400 along the x-axis. FIG. 10 shows that rotation of dial 116 is associated with telescoping of positioning arm 2000 along the x-axis. FIG. 10 also shows that rotation of dial 101 is associated with motion of instrument attachment component 107 of guiding arm 1000 along the z-axis. FIG. 11 shows that rotation of dial 131 is associated with telescoping of connecting arm 3000 along the y-axis.

Example 2

Stereotactic Apparatus without Side Clamp

Figure 1C:
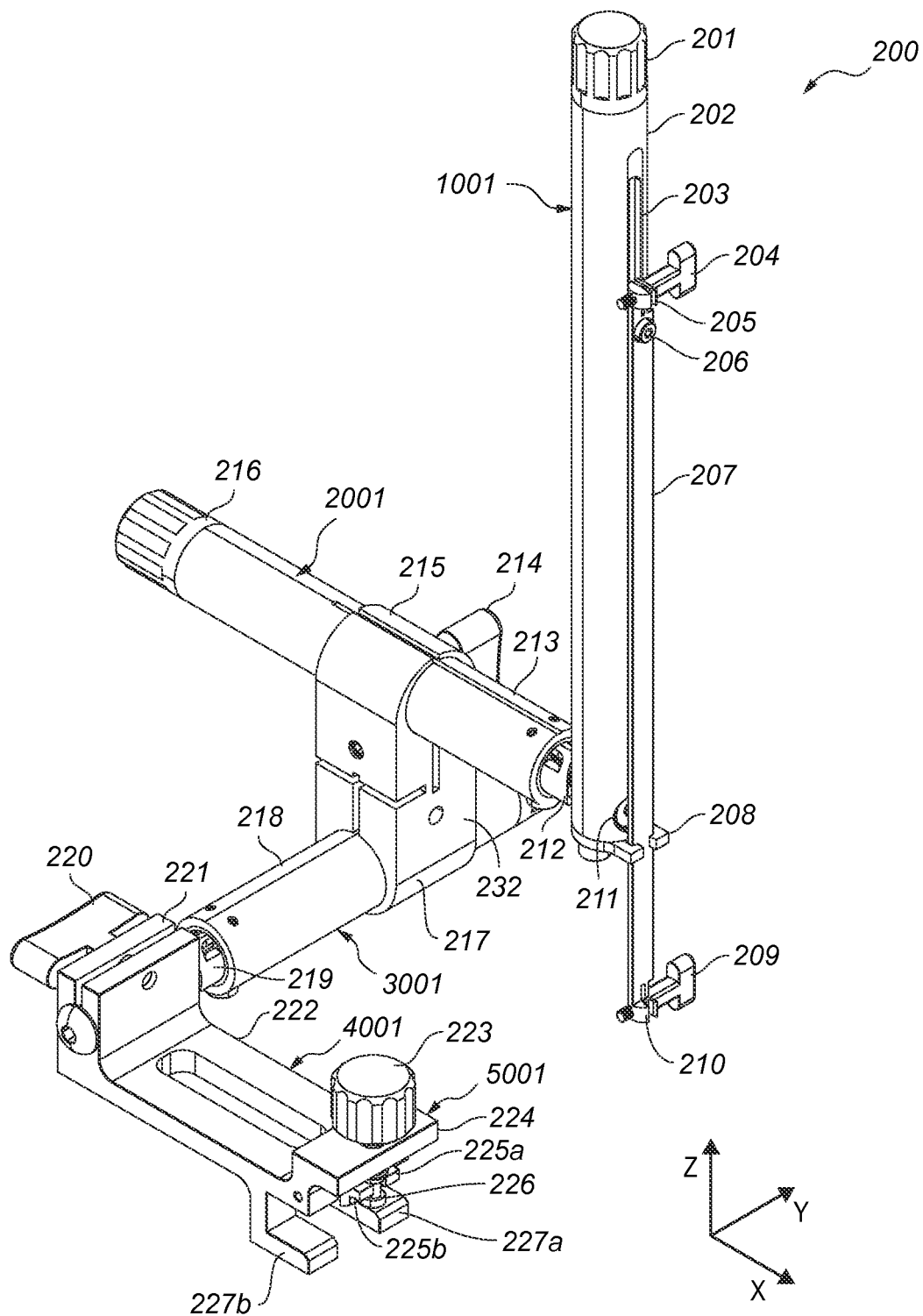
FIG. 1C depicts stereotactic apparatus 200.
Figure 1D:
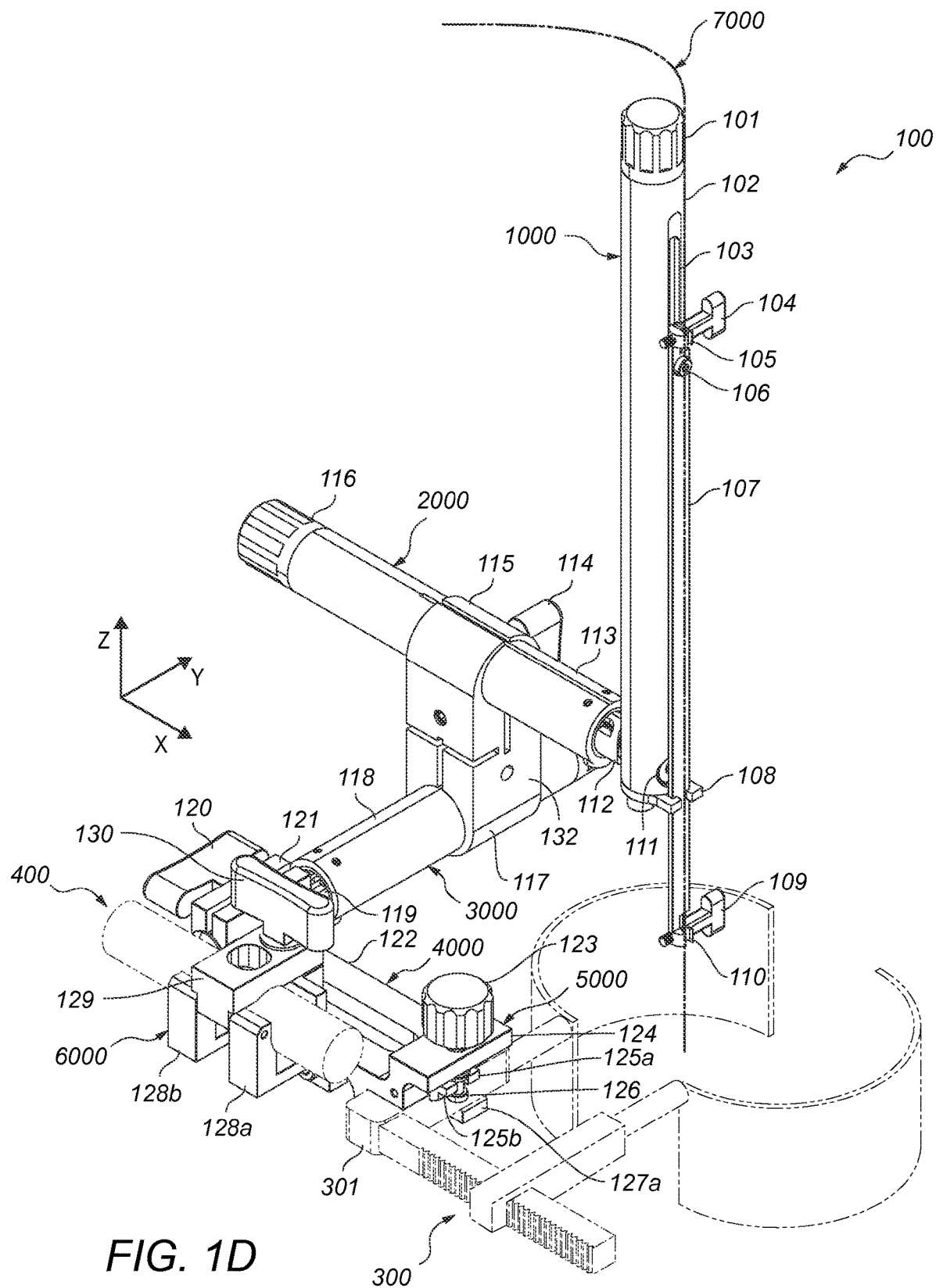
FIG. 1D depicts stereotactic apparatus 100 attached to cylindrical object 400 and tissue retractor 300. Instrument 7000 is shown attached to guiding arm 1000 of stereotactic apparatus 100, and extending downward along the z-axis between the arms of tissue retractor 300.
Figure 2A:
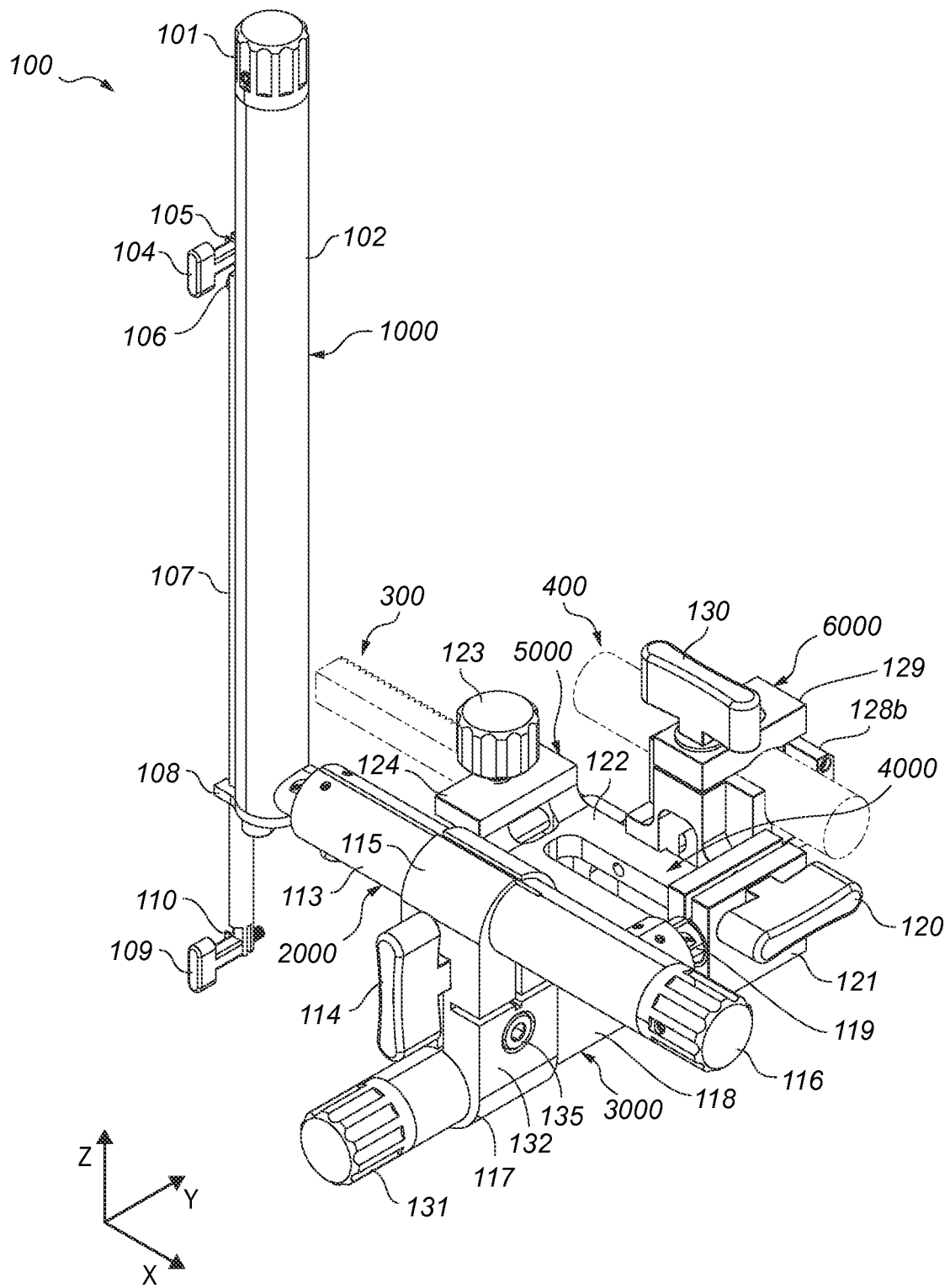
FIG. 2A depicts, in accordance with an embodiment of the invention, stereotactic apparatus 100. Tissue retractor 300 and cylindrical object 400 are shown.
Figure 2B:
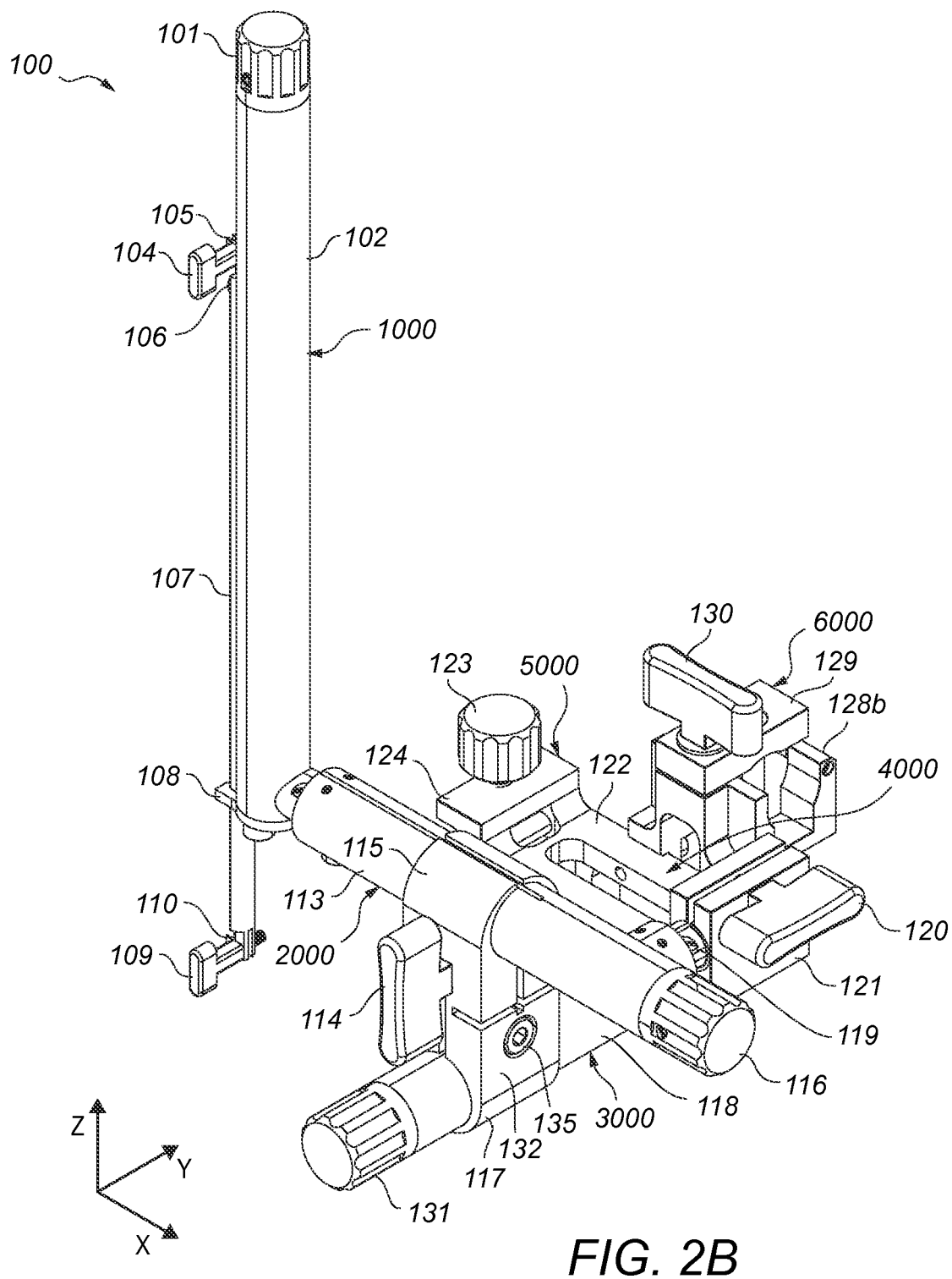
FIG. 2B depicts an alternate view of stereotactic apparatus 100.
Figure 2C:
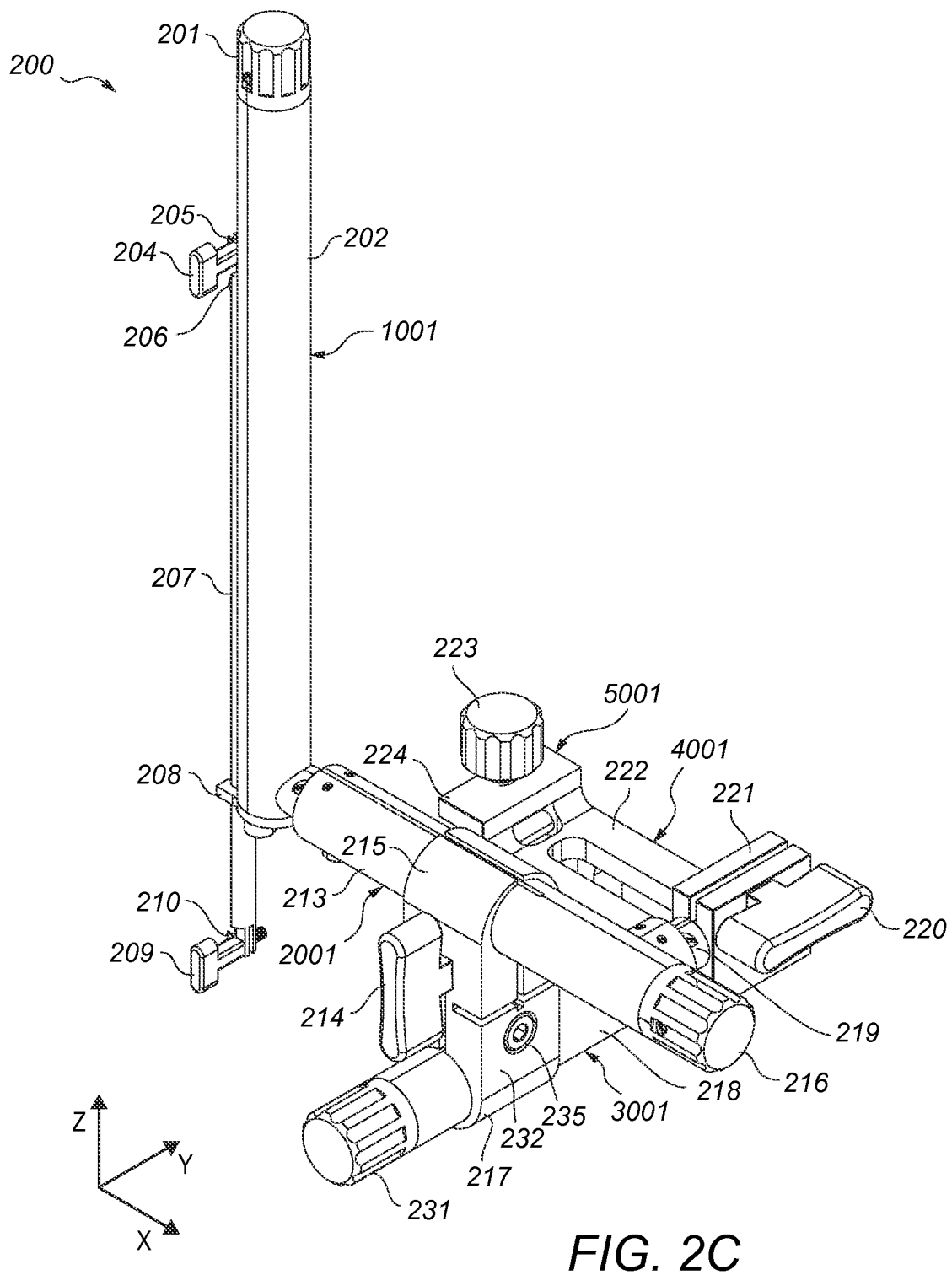
FIG. 2C depicts an alternate view of stereotactic apparatus 200.

FIGS. 1C and 2C depict stereotactic apparatus 200, which includes the same components as stereotactic apparatus 100, with the exception of the side clamp 128 depicted in stereotactic apparatus 100. Stereotactic apparatus 200 also functions in the same way as stereotactic apparatus 100, with the exception of the functions that relate to side clamp 128.

Example 3

Surgical Procedure

A single level laminectomy can be performed on the L4 vertebral segment. Standard anesthetic/preoperatory techniques are used and the patient is positioned prone. A 4 cm incision is made at the midline above the L4 spinous process. Cutting electrocautery is used to cut the fascia and extend the incision to the spinous process, as well as achieving hemostasis of any small hemorrhages from the incision site. At this point a Weitlaner retractor can be used to keep the incision open. A bilateral sub-periosteal dissection is performed carefully by elevating the muscles and periosteum off of the lamina. Cutting electrocautery is used to facilitate the dissection. The spinous process is then removed using a Leksell rongeur. A high-speed drill is used to thin the lamina. The lamina is then lifted and the ligamentous attachment is cut to release the lamina. Kerrison rongeurs are then be used to extend the laminectomy or clean up any left over bone fragments. In this case, the Medtronic Mast Quadrant refractor system is used. The Weitlaner retractor is removed, and the Mast Quadrant retractor blades are inserted into the incision and attached to the retractor system flex arms. The retractor is opened rostrocaudally to achieve maximum tissue spread. The mediolateral retractor is used in order to keep muscle out of the field. A ~2.5 cm dura incision is made using an #11 blade and a dural guide to prevent spinal cord injury. Using 4-0 Neurolon the dura is then tacked at the four corners of the opening to be able to visualize the nerve roots and facilitate injections. At this point, inventive device 100 is attached to the Mast Quadrant using clamp 5000. Coronal and saggital angles can be adjusted on the device depending on the spinal cord target using the adjustment mechanisms described above. In this case, the ventral horn is targeted, so a 90-degree (orthogonal) angle of the surgical instrument (needle, cannula, etc) to the spinal cord is established. The surgical instrument (needle, cannula) can now be attached to the device. Using the dials of the device, rostrocaudal and mediolateral movement can be achieved to find accurate placement to the target. The surgical instrument is then positioned into the spinal cord using the ventral rostral movement provided by dial 101 to the appropriate depth. Imaging (CT, MRI, Ultrasound, and the like) can be used to help position the device in all planes (coronal and saggital angle, rostrocaudal, mediolateral and dorsoventral positioning). When the surgical instrument (needle) is in position, the therapeutic agent (neural progenitor cells) can be infused into the spinal cord target. The surgical instrument is then returned to the starting position and can then be repositioned for subsequent injections. Once all of the injections/infusions are completed, the surgical instrument can be removed, followed by the device. The dura tacks can then be cut and the retractor system removed. The incision can then be closed in four layers. The dura is closed with a running stitch using a 4-0 neurolon. Once it's closed, a valsalva maneuver can be performed to ensure it's watertight and there's no cerebrospinal fluid leakage. The deep muscle layer is closed with a 0 Vycril suture as well as the Muscle fascia. The dermal layer is closed using a 3-0 vycril and finally the skin is closed using a locked running stitch with 2-0 nylon.

Example 4

Stereotactic Device with Cannula

Figure 23:
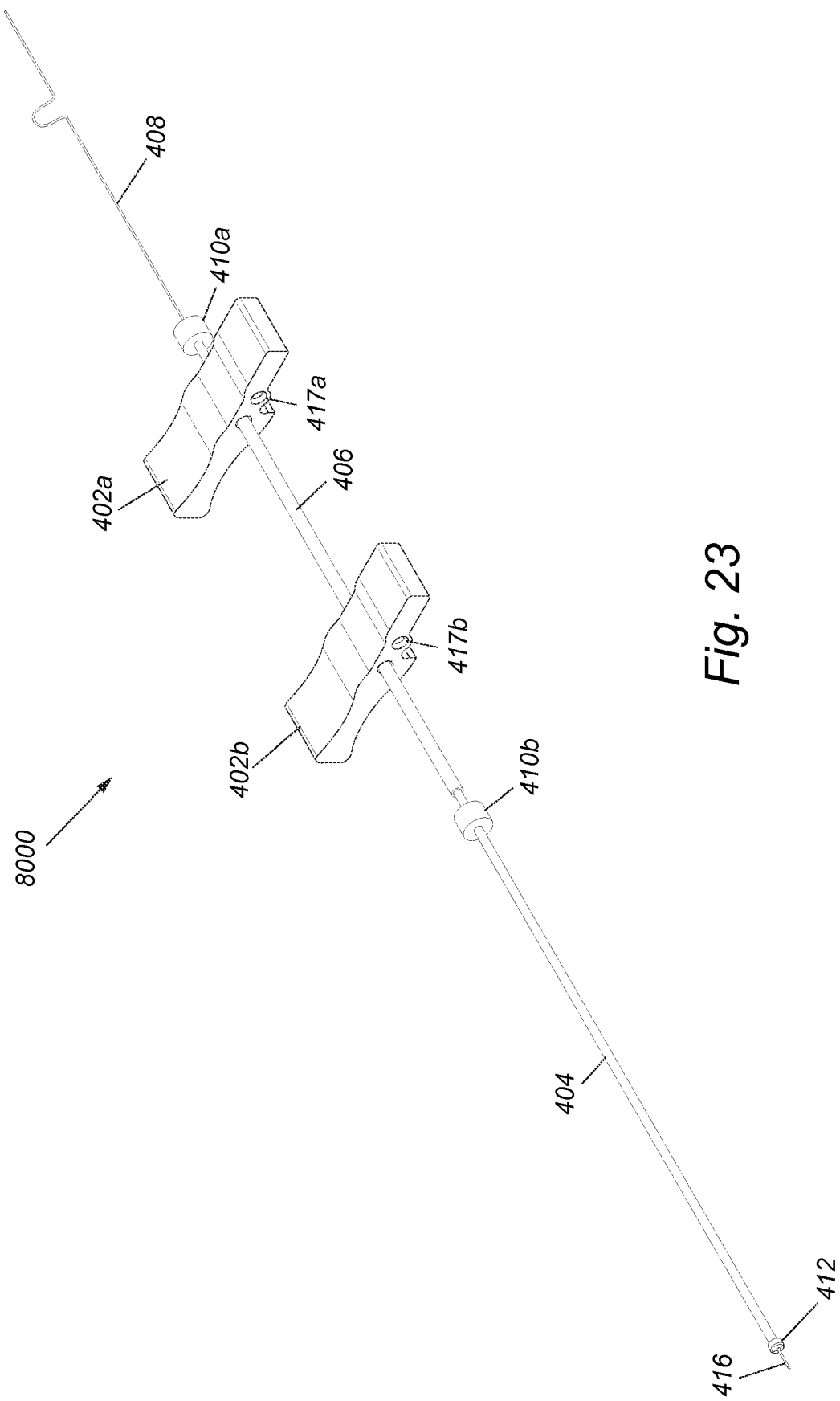
FIG. 23 depicts, in accordance with an embodiment of the invention, a perspective view of a floating cannula system 8000.
Figure 24:
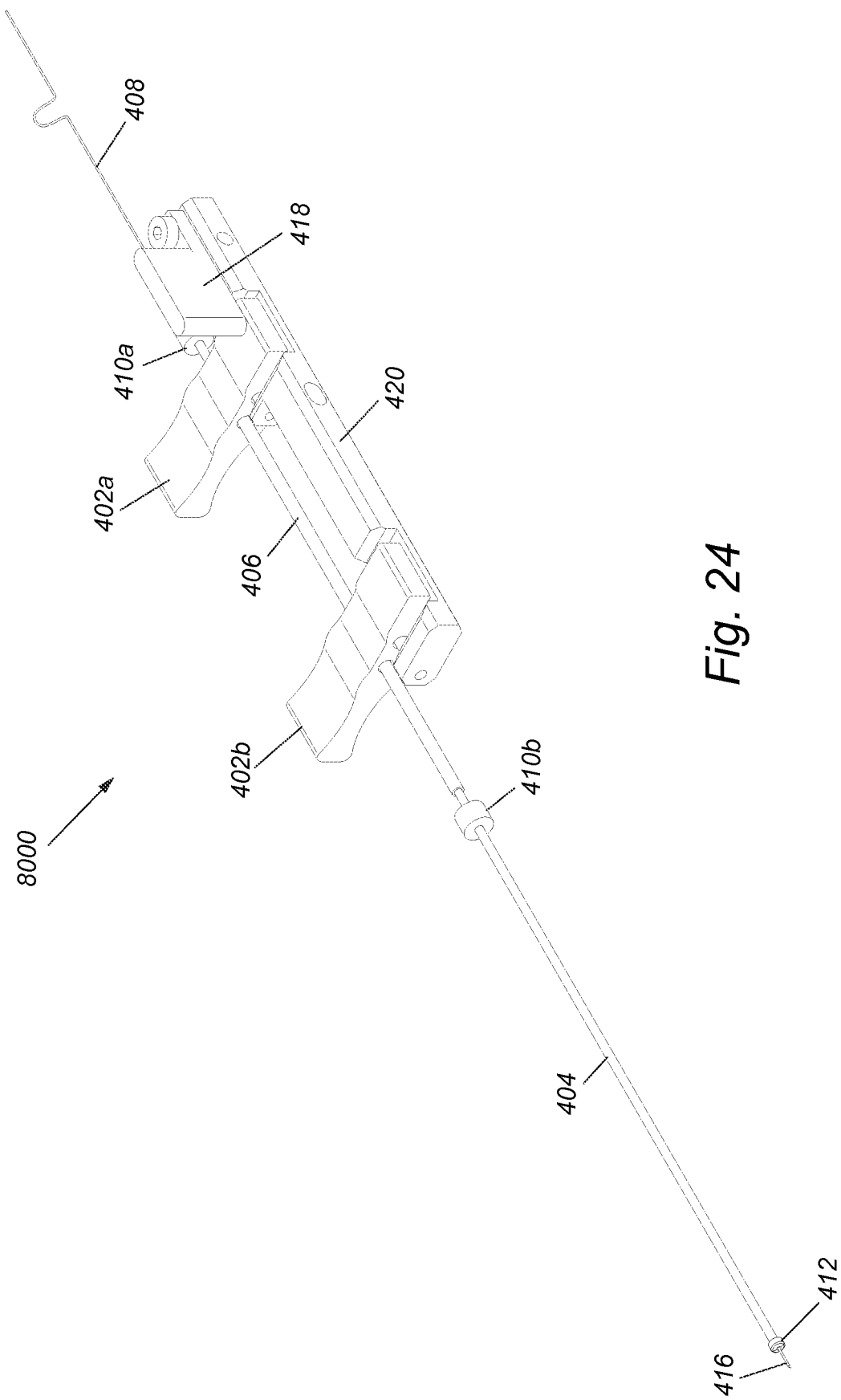
FIG. 24 depicts, in accordance with an embodiment of the invention, a perspective view of a floating cannula system 8000 attached to connector 420.

FIG. 23 depicts an example of a floating cannula system 8000 that may be attached to the guiding arm 1000 or other portion of a stereotactic apparatus 100 as disclosed herein. In some embodiments, the floating cannula system 8000 will include a base cannula 406 that has two support tabs 402a and 402b that are securely mounted to the base cannula 406. In some embodiments, the support tabs 402a and 402b may be utilized to connect the base cannula 406 to a stereotactic apparatus 100. In some embodiments, the support tabs 402a and 402b are spaced apart as shown in FIG. 23. In alternative embodiments, the support tabs may be closer together. In some embodiments, it may be advantageous to space the support tabs 402a and 402b so that they effectively stabilize the base cannula 406, in view of the length of the base cannula. In some embodiments, the base cannula 406 may only contain one or no support tabs and instead may be connected directly to a guiding arm 1000 of a stereotactic apparatus 100. In some embodiments, the support tabs 402a and 402b may contain attachment sockets 417a and 417b (FIG. 23) that are configured to receive pins from a connector or guiding arm 1000 of the stereotactic device.

The base cannula 406, in some embodiments, may have a proximal end and a distal end, wherein the proximal end is closer to the top portion of the cannula system 8000. The base cannula 406 may contain a floating cannula 404 inside the lumen of base cannula 406. The floating cannula 404, in some embodiments, is restrained from movement by its engagement with base cannula 406 except that it may slide in both directions along the longitudinal axis of base cannula 406.

In order to limit the distance the floating cannula 404 may travel in both directions along the longitudinal axis of the base cannula 406, the floating cannula 404 may include stoppers 410a and 410b. The stoppers 410a and 410b may be attached to the floating cannula 404 above and below the proximal and distal ends of the base cannula 406 respectively, when the floating cannula is engaged in the base cannula, as shown in FIG. 23. The proximal stopper 410a that is above the proximal end of the base cannula 406 will prevent the floating cannula 404 from falling out of the base cannula 406 (due to gravity) when positioned so that a portion of the floating cannula 404 extends beyond the distal end of the base cannula 406. The distal stopper 410b placed on the distal end of the floating cannula 404 restricts the floating cannula 404 from being pushed too far upward with respect to the base cannula 406, and may provide resistance for allowing a needle 416 to puncture a patient's tissue, once the distal stopper 410b contacts the distal end of the base cannula 406, as the base cannula is lowered toward an injection site on the patient.

In order to puncture tissue and deliver a substance to a patient, the floating cannula 404 may include a hollow needle 416 and a tissue stopper 412. The floating cannula system 8000 may be lowered down by the guiding arm 1000 of stereotactic device 100, until the needle 416 contacts the tissue of a patient. Then, once the needle contacts the patient's tissue, the floating cannula 404 will be pushed upwards with respect to the base cannula 406. As indicated above, the floating cannula 404 may include a distal stopper 410b that eventually contacts the distal edge/end of the base cannula 406 as the base cannula 406 is lowered towards the patient by the guiding arm 1000. Once the distal stopper 410b contacts the distal edge/end of the base cannula 406, the stopper will provide resistance and the floating cannula 404 will no longer move up with respect to the base cannula 406. Stoppers 410a and 410b may be any piece of material attached to the cannula 404 that prevents the base cannula 406 from sliding over or past the stoppers 410a and 410b (FIG. 23). Stoppers 410a and 410b thus could be configured as a bump, donut, cylinder, tab, square, wedge, or otherwise shaped obstruction large enough to prevent the floating cannula 404 from moving beyond a certain limit with respect to the base cannula 406. The stoppers 410a and 410b may be made of any suitable material, including plastics, rubbers, thermoplastics, glass, metal, wood or any others. In some embodiments, a rubber stopper may be utilized to prevent damaging the base cannula when it come into contact with the stopper.

Then, proceeding with the process of injection, if the guiding arm 1000 moves the base cannula 406 farther down towards the targeted tissue site, the needle 416 will puncture the targeted tissue site. The needle 416 will penetrate the tissue until the tissue stopper 412 contacts the tissue site. The tissue stopper 412 may be any suitable shape or size to prevent the needle 416 from entering further into the tissue. The tissue stopper 412 may be wedge shaped, disc shaped, or any other suitable shape. The tissue stopper 412 may be included on only part of the circumference of the needle 416 and other suitable arrangements. The tissue stopper 412 may be appropriately spaced/positioned with respect to the tip of the needle 416 to allow for the correct injection depth based on the particular procedure. In some embodiments, the tissue stopper may be movable with respect to the needle, in order to allow for different injection depths required for different procedures Once the needle 416 enters the body of the patient, and the tissue stopper 412 contacts the patient's tissue, the base cannula 406 may be pulled upwards. This may be accomplished by moving the guiding arm 1000 upwards, which would in turn move the attached base cannula 406 upwards. This would move the distal edge/end of the base cannula 406 away from and upwards with respect to the distal stopper 410b and provide a space or distance between the distal edge of the base cannula 406 and the distal stopper 410b. This will allow the floating cannula 404 a limited range of movement along the longitudinal axis of the cannulas. Accordingly, if the patient moves in a direction along that axis, the floating cannula 404 will move with respect to the base cannula 406, without causing damage to the patient. The travel of the floating cannula 404 along the longitudinal axis will be limited by the spacing of the distal 410b and proximal 410a stoppers relative to the length of the base cannula 406. This system 8000 will advantageously allow the needle 416 to be precision injected into the tissue site, and then allow some freedom of movement along the longitudinal axis, once the base cannula 406 is pulled back (further away from the tissue site).

In some embodiments, the substance to be injected into the patient will be delivered by a delivery tube 408 that may be connected to an external reservoir and pump. The reservoir will be connected to the delivery tube 408 which may then run along the length of the entire system 8000, within the lumens of the base cannula 406 and floating cannula 404, and connect to the needle 416 (or include a penetrating tip that serves as the needle 416). In some embodiments, the delivery tube 408 may only connect to the floating cannula 406 and deliver the substance to inside the lumen of the cannula 406.

Figure 25:
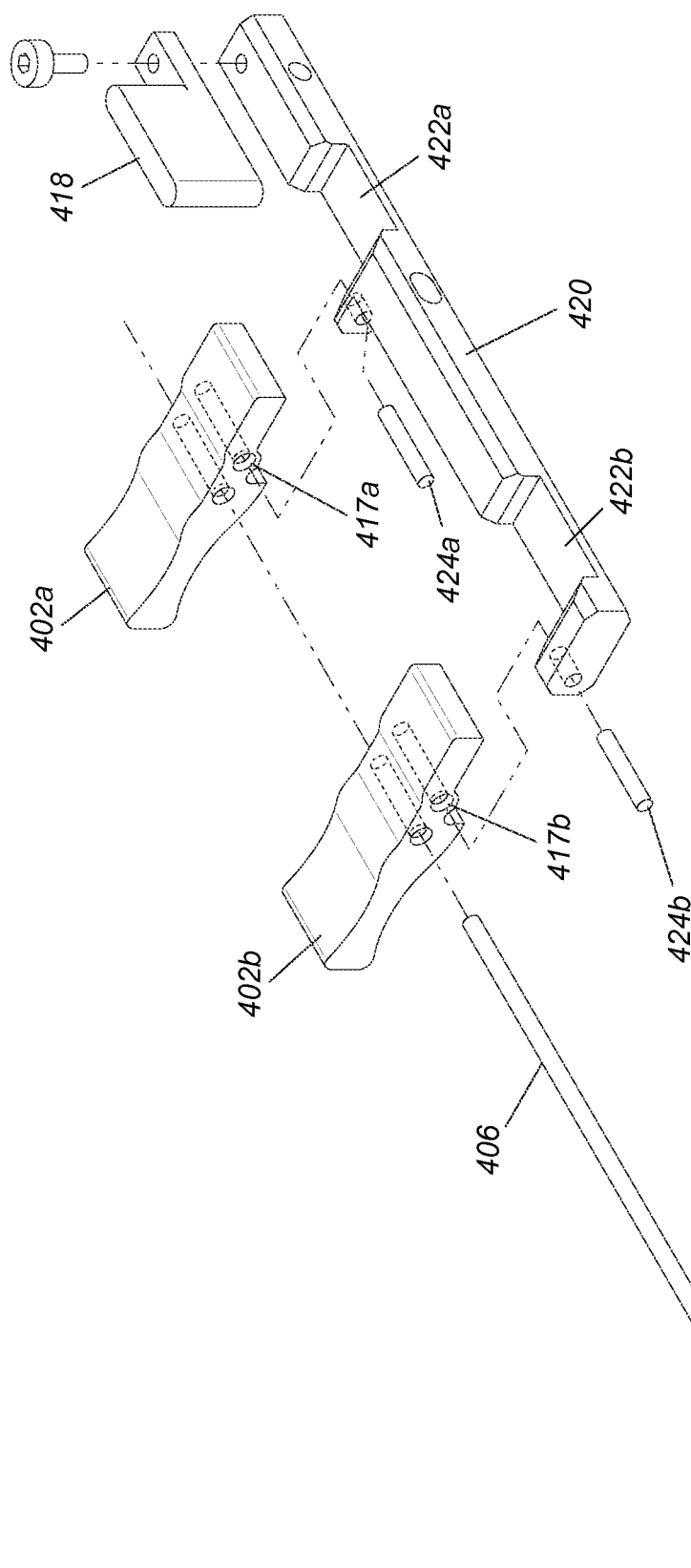
FIG. 25 depicts, in accordance with an embodiment of the invention, an exploded view of a floating cannula system 8000 and connector 420.

FIG. 24 illustrates the floating cannula system 8000 connected to a connector 420 configured to connect the system 8000 to a stereotactic device 100. The connector 420, in some embodiments, includes a tab lock 418 that mounts the support tabs 402a and 402b to the connector 420. In some embodiments, the tab lock 418 creates an interference fit. In the illustrated embodiments, the sockets 417a and 417b of the support tabs 402a and 402b are inserted onto pins 424a and 424b that are included in the connector 420 (FIG. 25). The pins 424a and 424b then provide translational restraint of the cannula system 8000 in a plane perpendicular to the longitudinal axis of the cannulas. Then, the support tabs 402a and 402b may be rotated into place inside a space or indentation 422a and 422b in the connector 420 by rotation around the pins 424a and 424b that are attached to the connector 420. Once the support tabs 402a and 402b have been rotated into place, a tab lock 418 may be rotated into place, (based on a rotation or sliding action or other suitable mechanical means) to block the tabs 402a and 402b from rotating back out of the spaces 422a and 422b in the connector 420 (FIGS. 24 and 25). In other embodiments, the tabs 402a and 402b may be attached to connector 420 through other suitable mechanical devices, including buckles or other mechanical connections.

FIG. 25 depicts an exploded view of the connector 420, along with the base cannula 406 and tabs 402a and 402b. As depicted, the tabs 402a and 402b include sockets 417a and 417b, in which pins 424a and 424b may fit. The pins 424a and 424b may be attached to the connector 420 and positioned so that when the tab sockets 417a and 417b are positioned onto the pins 424a and 424b the tabs 402a and 402b may be rotated into the spaces or indentations 422a and 422b in the connector 420. The spaces or indentations 422a and 422b in the connector may be configured to accommodate the support tab ends, so that the support tabs will be restricted in the direction parallel to the longitudinal axis of the cannulas. In this embodiment, the spaces or indentations 422a and 422b are illustrated to include a square shape, so that they may accommodate a square end of the tabs 402a and 402b that may be rotated into place about pins 424a and 424b and locked there with the tab lock 418.

Figure 26:
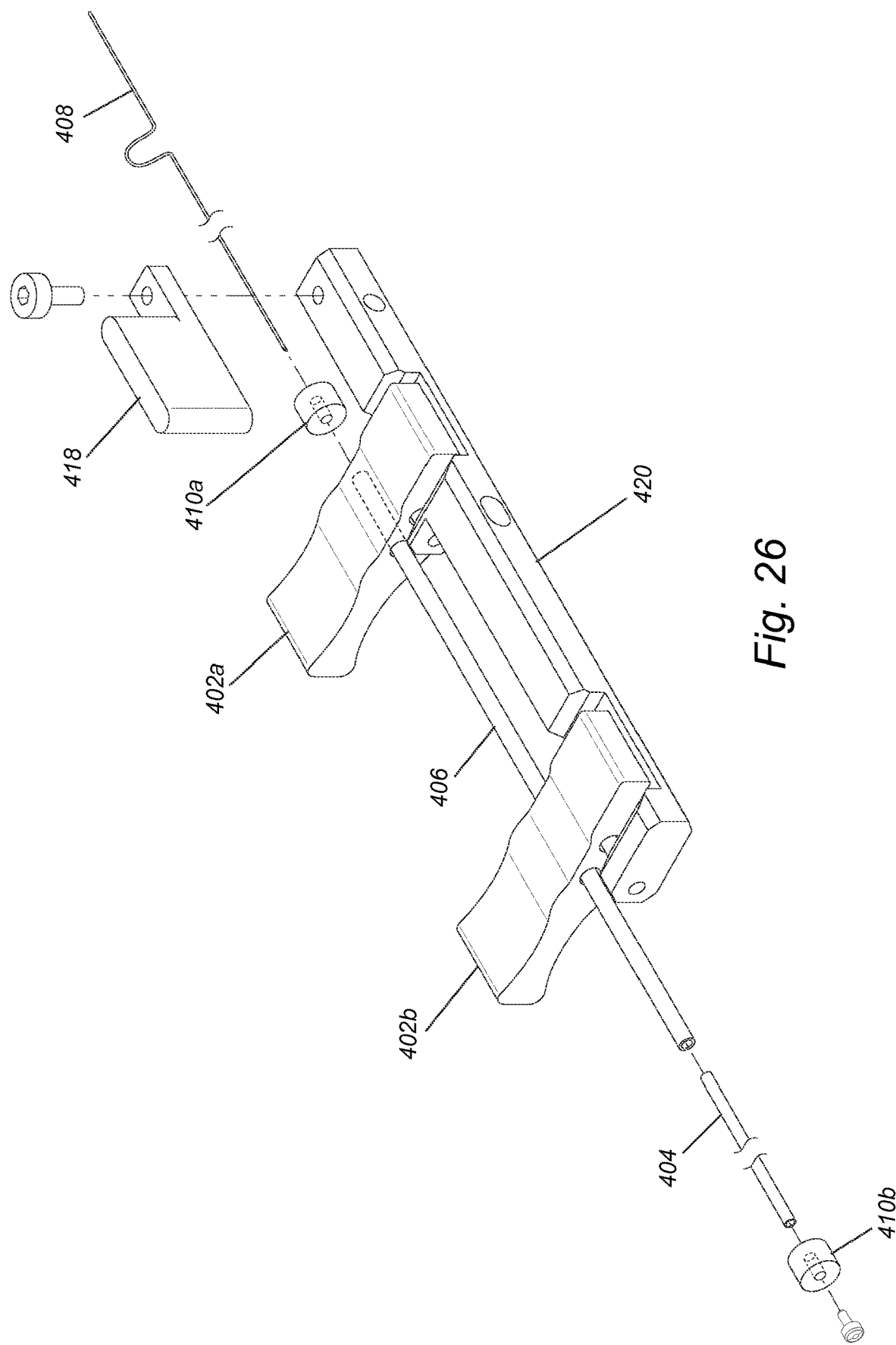
FIG. 26 depicts, in accordance with an embodiment of the invention, a perspective and exploded view of a floating cannula system 8000 attached to connector 420.
Figure 27:
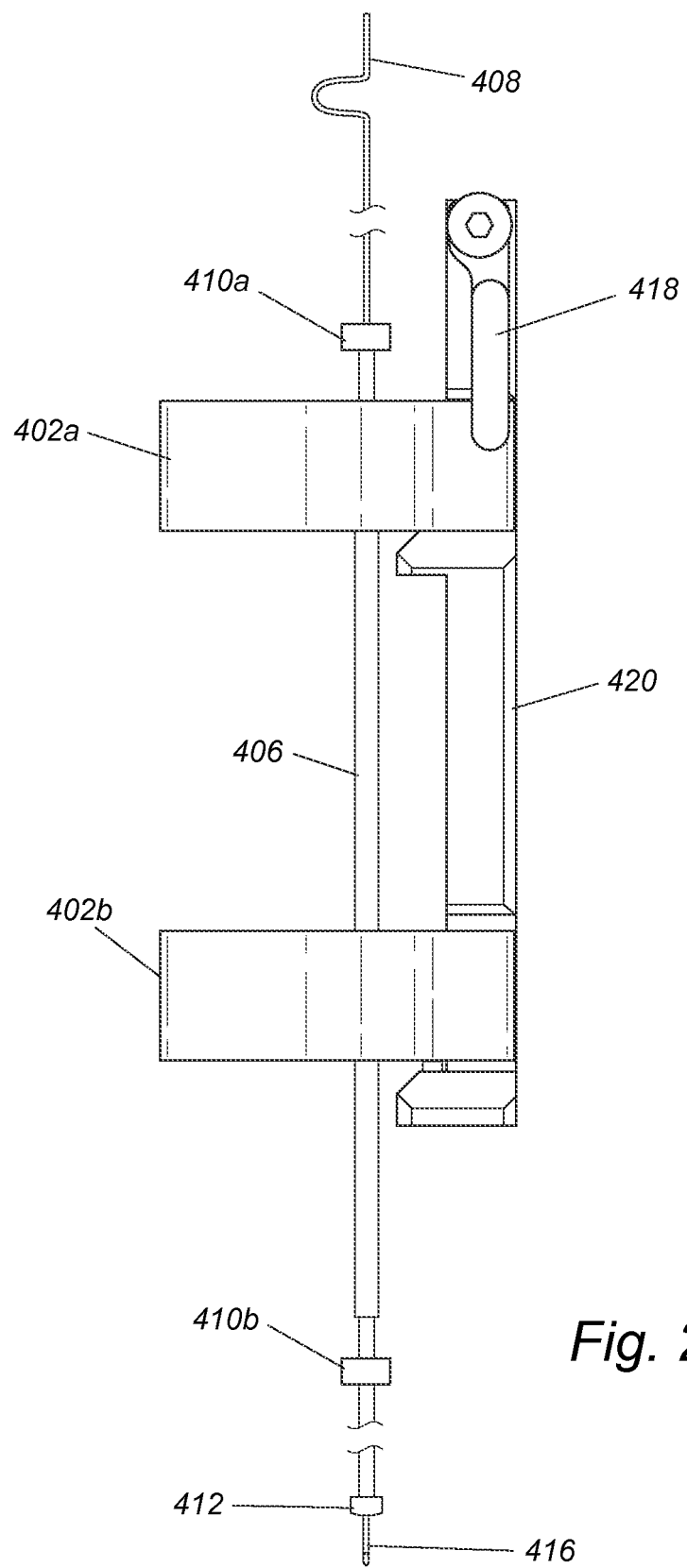
FIG. 27 depicts, in accordance with an embodiment of the invention, a side view of a floating cannula system 8000 attached to connector 420.

FIG. 26 illustrates an exploded view of the system 8000 with the base cannula 406 connected to the connector 420.

FIG. 27 illustrates a side view of the system 8000 with the base cannula 406 attached to the connector 420.

Figure 28:
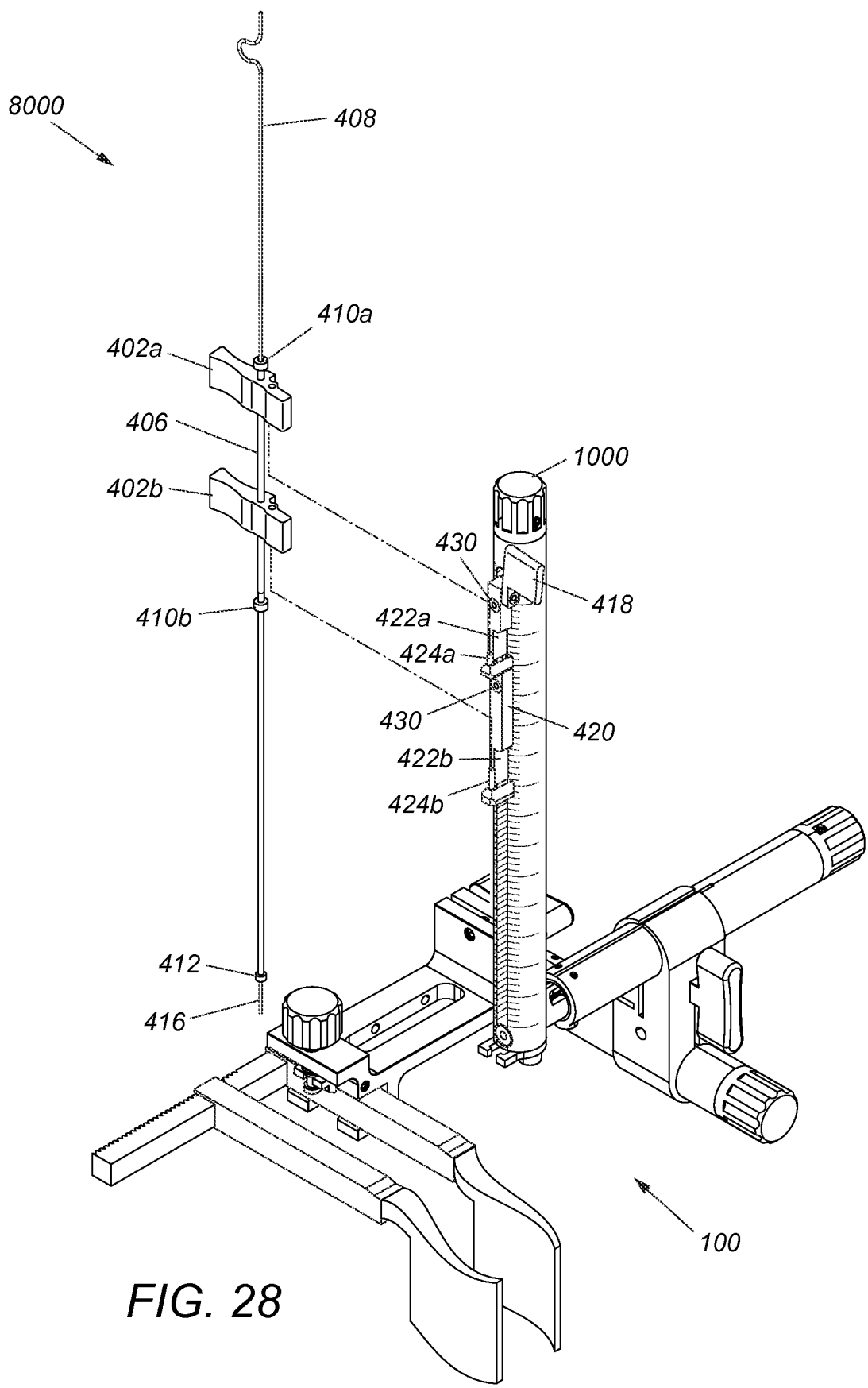
FIG. 28 depicts, in accordance with an embodiment of the invention, a perspective view of a floating cannula system 8000 prior to attachment to a connector 420 and stereotactic device 100.

FIG. 28 illustrates an embodiment in which the floating cannula system 8000 and connector 420 are connected to the guiding arm 1000 of the stereotactic device 100. The connector 420 may be attached to the guiding arm 1000 with screw 430 (alternative means of attachment, as described herein, may be separately or additionally used). FIG. 28 illustrates the connector 420 with the pins 424a and 424b inserted and the floating cannula system being moved towards the pins, so that the sockets 417a and 417b of the tabs 402a and 402b may be mounted on the pins 424a and 424b. However, in FIG. 28, the support tabs 402a and 402b have not yet been rotated inside spaces or indentations 422a and 422b of the connector 420. This allows the support tabs 402a and 402b to slide onto pins 424a and 424b when first placed on the pins 424a and 424b in an orientation that is rotated approximately 90 degrees from the orientation they assume once secured.

Figure 29:
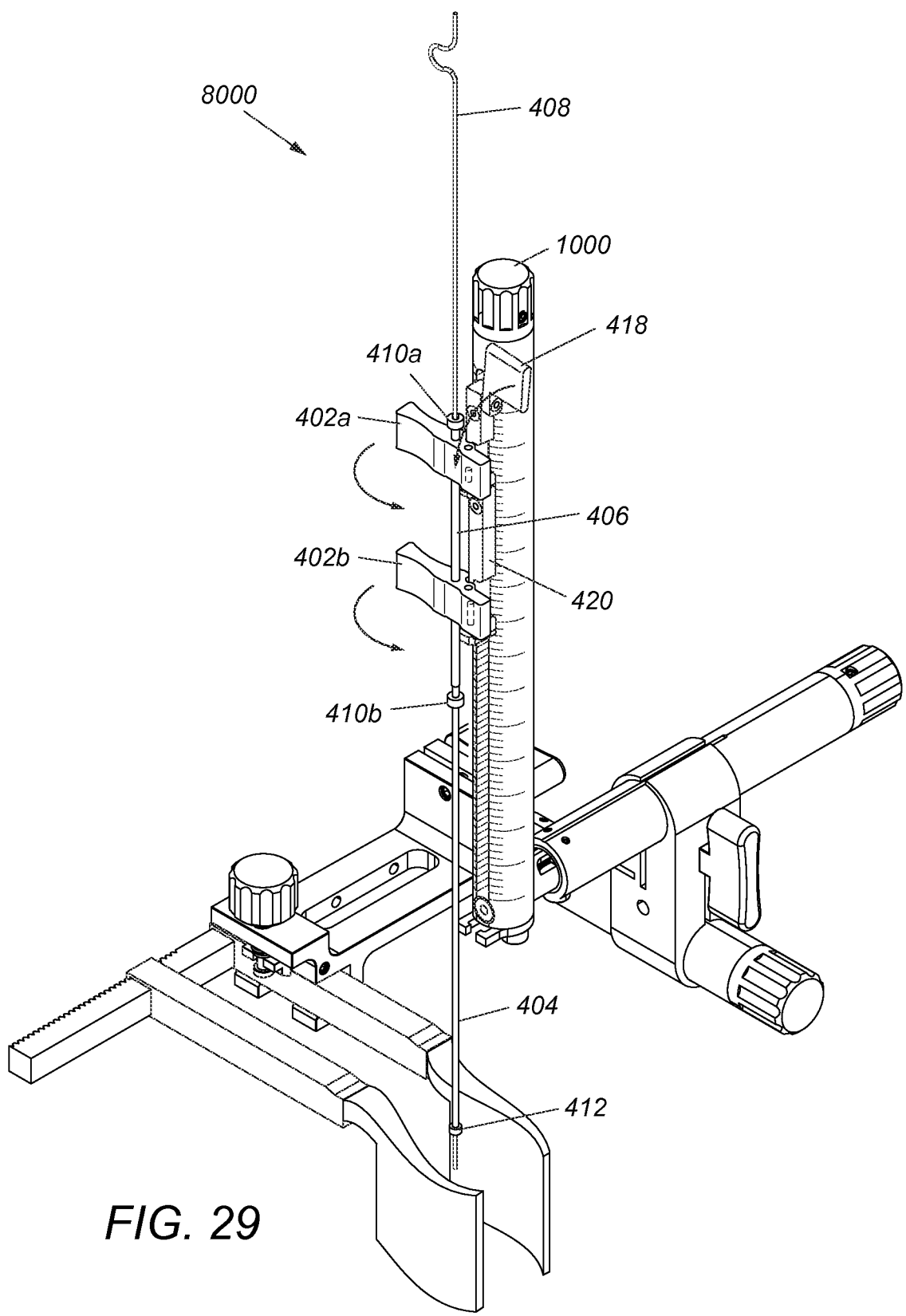
FIG. 29 depicts, in accordance with an embodiment of the invention, a perspective view of a floating cannula system 8000 and support tabs 402a and 402b that have been mounted on pins 424a and 424b (shown in FIG. 28) of connector 420 and stereotactic device 100.

FIG. 29 illustrates the tabs 402a and 402b mounted onto the pins 424a and 424b (shown in FIG. 28). In some embodiments, the user may grip the support tabs 402a and 402b and then move the bottom opening of each of the sockets 417a and 417b above the pins 424a and 424b, followed by sliding the support tabs 402a and 402b down the pins 424a and 424b. Accordingly, the pins 424a and 424b will hold the support tabs 402a and 402b in place and only allow them to slide up and down along pins 424a and 424b, or rotate about pins 424a and 424b.

Once the tabs 402a and 402b have been placed on the pins 424a and 424b in the orientation shown, the tabs may be rotated 90 degrees as shown in FIG. 29, so that the edges of the tabs reside in the spaces or indentations 422a and 422b (shown in FIG. 25).

Once the support tabs 402a and 402b have been rotated into place, the top and bottom of the spaces or indentations 422a and 422b will restrain the tabs 402a and 402b, and therefore floating cannula system 8000 from moving up or down or in a direction along the longitudinal axis of the cannulas. FIG. 29 illustrates with an arrow the direction that the support tabs 402 have been rotated.

Once the support tabs 402a and 402b are rotated into spaces or indentations 422a and 422b, the tab lock 418 may be rotated down to create an interference fit, which prevents the support tabs 402a and 402b from rotating back out. In this embodiment, because support tabs 402a and 402b are securely attached to the base cannula 406, only one tab lock 418 may be required to block rotation of one of the support tabs 402a and 402b. In other embodiments, both support tabs 402a and 402b may have tab locks 418 that block their rotation out of spaces or indentations 422a and 422b.

Figure 30:
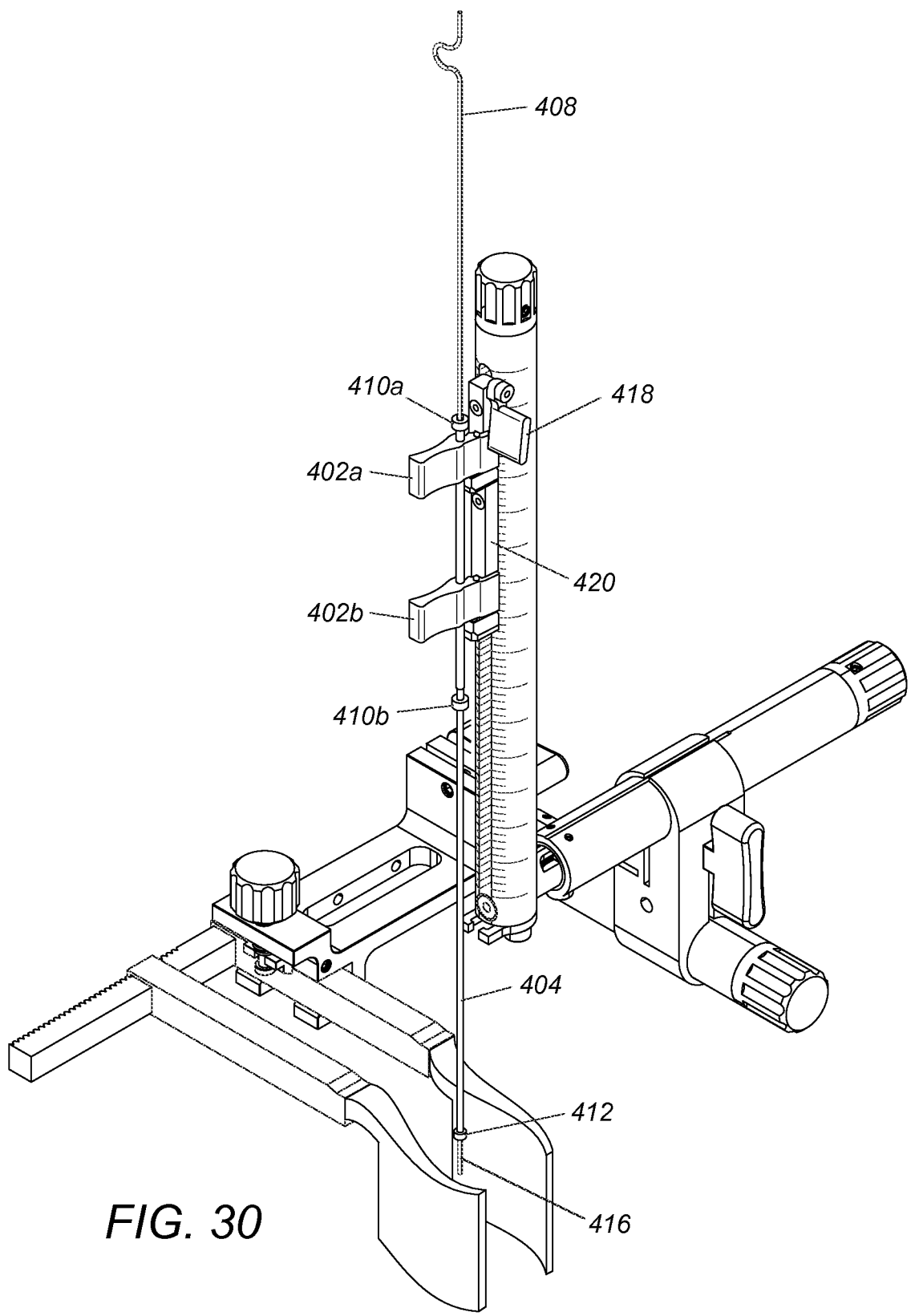
FIG. 30 depicts, in accordance with an embodiment of the invention, a perspective view of a floating cannula system 8000 attached to a connector 420 and stereotactic device 100 after the support tabs 402a and 402b have been rotated into spaces or indentations 422a and 422b.

FIG. 30 illustrates the support tabs 402a and 402b and floating cannula system 8000 rotated into place in the spaces or indentations 422a and 422b, and the tab lock 418 secured into place. In this configuration, the floating cannula system 8000 is securely attached to the connector 420 and guiding arm 1000 of the stereotactic device 100. As indicated above, the support tabs 402a and 402b are securely held to the connector 420 by the pins 424a and 424b, spaces 422a and 422b and the tab lock 418. As described herein, other methods of attaching the floating cannula system 8000 to the guiding arm 1000 may be utilized. As described herein, the floating cannula system 8000 may be advanced towards a tissue site to bring the needle 416 in closer proximity to the site by lowering the guiding arm 1000.

The floating cannula system described above may be utilized for a variety of procedures that require a precision injection. Merely by way of non-limiting examples, precision injections may be performed on a patient to introduce sustained release peptides, cells (including stem cells), vectors for gene therapy, or any other medically relevant substance described herein. The injections may be made to the spinal cord parenchyma, other neurological structures, and other parts of the body, as described herein. In some embodiments, the floating cannula system is used to inject neural progenitor cells into the spinal cord of a subject. In some embodiments, the neural progenitor cells express glial cell line derived neurotrophic factor. In some embodiments, the subject is a human who has been diagnosed with amyotrophic lateral sclerosis (ALS).

Example 5

Syringe Pump

Figure 32:
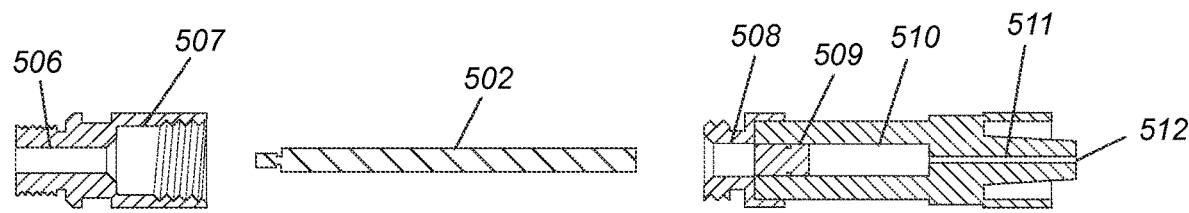
FIG. 32 depicts, in accordance with an embodiment of the invention, a cross-sectional and partially exploded view of a portion of syringe pump 9000.
Figure 33:
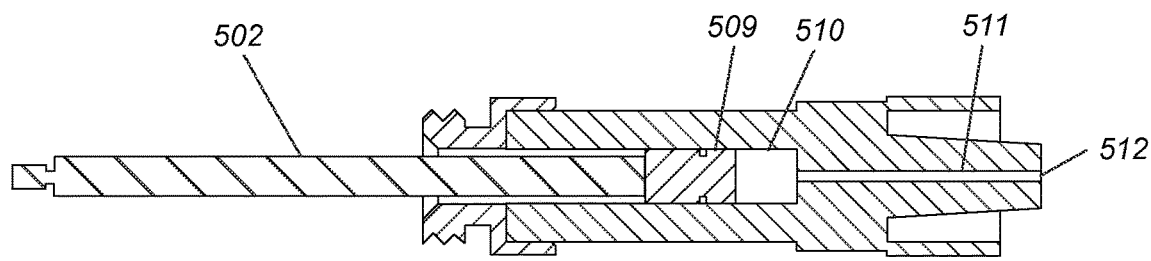
FIG. 33 depicts, in accordance with an embodiment of the invention, a cross-sectional view of a portion of syringe pump 9000.
Figure 34:
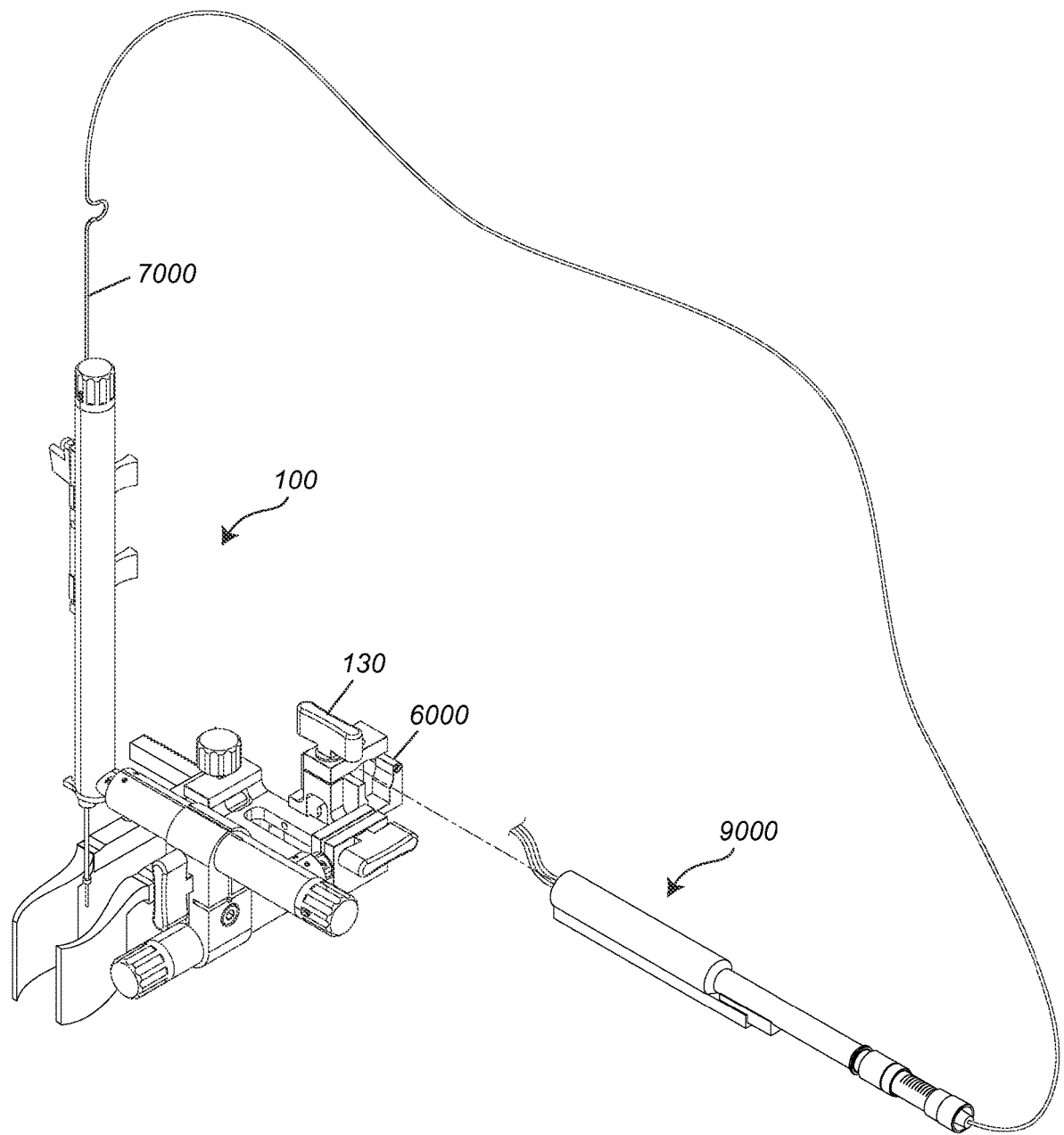
FIG. 34 depicts, in accordance with an embodiment of the invention, syringe pump 9000 can be positioned in side clamp 6000 of stereotactic device 100.

FIG. 31 depicts a partially exploded view of a syringe pump system 9000, in which a carpule assembly 501, a drive shaft 502, a coupling collar 503 and a motor assembly housing 504 can be seen. The motor 513 of syringe pump system 9000 is configured to cause rotatable drive shaft 502 to rotate. As shown in FIG. 32, the carpule assembly includes an elongated inlet port 508, an elongated outlet port 511, and a chamber 510 disposed between and in fluid communication with elongated inlet port 508 and elongated outlet port 511. FIG. 32 also shows an elongated plunger 509, which is configured to nest within elongated inlet port 508. As shown in FIG. 32, the pushing end of elongated plunger 509 is configured to form a substantially fluid-tight seal with chamber 510, and rotatable drive shaft 502 is configured to apply a drive force to the receiving end of plunger 509. With this configuration, plunger 509 can be pushed in the direction of outlet port 511 (FIG. 33), thereby expelling any fluid in chamber 510 through outlet port opening 512.

As shown in FIG. 31, coupling collar 503 is configured to connect on one end to motor housing assembly 504, and on the other end to carpule assembly 501.

Figure 36:
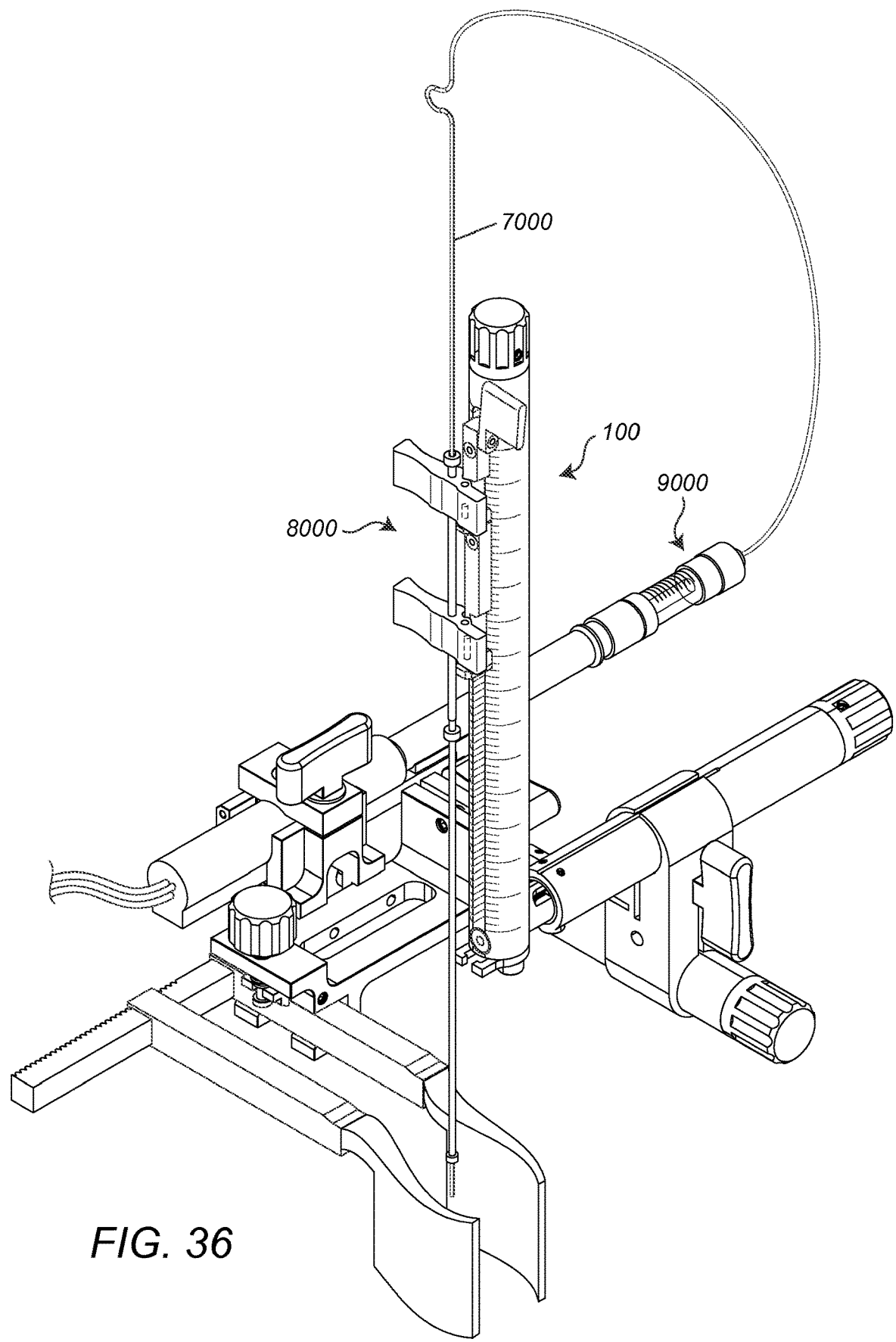
FIG. 36 depicts, in accordance with an embodiment of the invention, syringe pump 9000 connected to floating cannula 8000 through delivery tube 7000. The floating cannula 8000 is shown connected to the guiding arm of stereotactic device 100.

FIG. 36 depicts cannula delivery tube 7000 connected to syringe pump system 9000 and floating cannula system 8000.

As shown in FIG. 37 cannula delivery tube 7000 can be connected to carpule delivery tube 10000 through Leur lock fittings 10003 and 10002. FIG. 37 also shows carpule delivery tube 10000 can be connected to syringe pump system 9000 through coupling collar 10001. As described herein, cannula delivery tube 7000 may be directly connected to a hollow needle on the tip of the floating cannula, by running through the lumens of the base and floating cannulas of the cannula system.

An inventive syringe pump system described herein can be used in conjunction with a floating cannula system described herein and a stereotactic device described herein, in order to deliver neural progenitor cells expressing glial cell line derived neurotrophic factor into a patient's spinal cord. For example, using the configuration shown in FIG. 37, once a laminectomy is performed and a section of the spinal cord is accessible (by performing the surgical method described above), the guiding arm of the stereotactic device can be used to advance the hollow needle of the floating cannula into the patient's spinal cord. Once the hollow needle is inserted into the patient's spinal cord, the base cannula can be refracted by retracting the guiding arm upward from the injection site, thereby allowing for travel of the floating cannula within the base cannula, along the longitudinal axis of the base cannula. Next, the syringe pump can be used to pump saline, which was preloaded in the carpule, through carpule delivery tube 10000, which was preloaded with neural progenitor cells expressing glial cell line derived neurotrophic factor, thereby advancing the cells and saline through cannula delivery tube 7000, and ultimately through the hollow needle of the floating cannula and into the patient's spinal cord. If necessary, this procedure can be repeated at the same injection site, or at a different injection site, by replacing the used carpule and carpule delivery tube with a new carpule and carpule delivery tube that have been preloaded with saline and cells, respectively, as described above. After one or multiple injections are performed, the cannula can be retracted by completely retracting the guiding arm of the stereotactic device from the surgical site, and the incision in the patient can be closed according to the surgical procedure described above.

Although the delivery of therapeutic cells to the spinal cord is specifically described in the example above, any fluid therapeutic substance (or imaging substance) could be delivered into the spinal cord, or other anatomical targets, using the cannulas, stereotactic devices, and syringe pump systems described herein.

The various methods and techniques described above provide a number of ways to carry out the invention. Of course, it is to be understood that not necessarily all objectives or advantages described can be achieved in accordance with any particular embodiment described herein. Thus, for example, those skilled in the art will recognize that the methods can be performed in a manner that achieves or optimizes one advantage or group of advantages as taught herein without necessarily achieving other objectives or advantages as taught or suggested herein. A variety of alternatives are mentioned herein. It is to be understood that some embodiments specifically include one, another, or several features, while others specifically exclude one, another, or several features, while still others mitigate a particular feature by inclusion of one, another, or several advantageous features.

Furthermore, the skilled artisan will recognize the applicability of various features from different embodiments. Similarly, the various elements, features and steps discussed above, as well as other known equivalents for each such element, feature or step, can be employed in various combinations by one of ordinary skill in this art to perform methods in accordance with the principles described herein. Among the various elements, features, and steps some will be specifically included and others specifically excluded in diverse embodiments.

Although the application has been disclosed in the context of certain embodiments and examples, it will be understood by those skilled in the art that the embodiments of the application extend beyond the specifically disclosed embodiments to other alternative embodiments and/or uses and modifications and equivalents thereof.

In some embodiments, the terms "a" and "an" and "the" and similar references used in the context of describing a particular embodiment of the application (especially in the context of certain of the following claims) can be construed to cover both the singular and the plural. The recitation of ranges of values herein is merely intended to serve as a shorthand method of referring individually to each separate value falling within the range. Unless otherwise indicated herein, each individual value is incorporated into the specification as if it were individually recited herein. All methods described herein can be performed in any suitable order unless otherwise indicated herein or otherwise clearly contradicted by context. The use of any and all examples, or exemplary language (for example, "such as") provided with respect to certain embodiments herein is intended merely to better illuminate the application and does not pose a limitation on the scope of the application otherwise claimed. No language in the specification should be construed as indicating any non-claimed element essential to the practice of the application.

Certain embodiments of this application are described herein, including the best mode known to the inventors for carrying out the application. Variations on those embodiments will become apparent to those of ordinary skill in the art upon reading the foregoing description. It is contemplated that skilled artisans can employ such variations as appropriate, and the application can be practiced otherwise than specifically described herein. Accordingly, many embodiments of this application include all modifications and equivalents of the subject matter recited in the claims appended hereto as permitted by applicable law. Moreover, any combination of the above-described elements in all possible variations thereof is encompassed by the application unless otherwise indicated herein or otherwise clearly contradicted by context.

All patents, patent applications, publications of patent applications, and other material, such as articles, books, specifications, publications, documents, things, and/or the like, referenced herein are hereby incorporated herein by this reference in their entirety for all purposes, excepting any prosecution file history associated with same, any of same that is inconsistent with or in conflict with the present document, or any of same that may have a limiting affect as to the broadest scope of the claims now or later associated with the present document. By way of example, should there be any inconsistency or conflict between the description, definition, and/or the use of a term associated with any of the incorporated material and that associated with the present document, the description, definition, and/or the use of the term in the present document shall prevail.

In closing, it is to be understood that the embodiments of the application disclosed herein are illustrative of the principles of the embodiments of the application. Other modifications that can be employed can be within the scope of the application. Thus, by way of example, but not of limitation, alternative configurations of the embodiments of the application can be utilized in accordance with the teachings herein. Accordingly, embodiments of the present application are not limited to that precisely as shown and described.

What is claimed is:

1. A floating cannula system for injecting a substance into a subject, the system comprising:
  a base cannula comprising a proximal end, a distal end, and a lumen connecting the distal and proximal ends, and wherein the lumen is continuous from the proximal end to the distal end;
  a floating cannula comprising a lumen, wherein (1) the floating cannula is configured to be at least partially contained inside the lumen of the base cannula, (2) the floating cannula comprises a proximal end and a distal end that extend farther proximally and distally than the proximal end and the distal end of the base cannula when the floating cannula is engaging in the base cannula, and (3) the floating cannula is configured to slide along a longitudinal axis of the base cannula and with respect to the base cannula to accommodate movement of the subject without any force except for a longitudinal force being applied to the floating cannula when engaged in the base cannula;
  a distal stopper connected to the distal end of the floating cannula, wherein the distal stopper is configured and positioned to prevent movement of the distal stopper in a proximal direction past the distal end of the base cannula by direct contact of the distal stopper with the distal end of the base cannula, when the floating cannula is engaged in the base cannula;
a proximal stopper connected to the proximal end of the floating cannula, wherein the proximal stopper is configured and positioned to prevent movement of the proximal stopper in a distal direction past the proximal end of the base cannula by direct contact of the proximal stopper with the proximal end of the base cannula, and wherein a distance from the proximal stopper to the distal stopper is greater than a distance between the proximal and distal ends of the base cannula;
a hollow needle directly connected to the distal end of the floating cannula; and
a delivery tube connected to the hollow needle, wherein at least part of a length of the delivery tube is contained inside the lumen of the floating cannula and the lumen of the base cannula.

2. The floating cannula system of claim 1, wherein one or more support tabs are connected to the base cannula.

3. The floating cannula system of claim 2, further comprising a connector removably attached to the one or more support tabs.

4. The floating cannula system of claim 3, further comprising a stereotactic device comprising a guiding arm configured to be lowered into a surgical field, wherein the connector is removably attached to the guiding arm of the stereotactic device.

5. The floating cannula system of claim 2, wherein the one or more support tabs comprise finger grips.

6. The floating cannula system of claim 3, wherein the connector includes one or more indentations configured to closely fit an end of the one or more of the support tabs.

7. The floating cannula system of claim 6, wherein the connector includes a tab lock that locks the one or more of the support tabs in place in the one or more indentations.

8. The floating cannula system of claim 1, wherein the delivery tube is connected to an external pump and a reservoir, and wherein the reservoir contains the substance to inject into the subject.

9. The floating cannula system of claim 1, wherein the needle comprises a tissue stopper; and wherein the needle is configured to be inserted into a tissue of the subject due to pressure applied by direct contact of the base cannula with the distal stopper when a downward force is applied to the base cannula, the downward force along the longitudinal axis.

10. The floating cannula system of claim 1, wherein a position of the distal stopper or the proximal stopper on the floating cannula is able to be changed.

* * * * *